US011591416B2

(12) United States Patent
Biffi et al.

(10) Patent No.: US 11,591,416 B2
(45) Date of Patent: Feb. 28, 2023

(54) EXOPOLYSACCHARIDES AND USES THEREOF

(71) Applicant: SOFAR S.P.A., Trezzano Rosa (IT)

(72) Inventors: Andrea Biffi, Urgnano (IT); Ruggero Rossi, Milan (IT); Walter Fiore, Milan (IT); Simone Domenico Guglielmetti, Milan (IT); Silvia Balzaretti, Vercelli (IT)

(73) Assignee: SOFAR S.P.A., Trezzano Rosa (IT)

( * ) Notice: Subject to any disclaimer, the term of this patent is extended or adjusted under 35 U.S.C. 154(b) by 0 days.

(21) Appl. No.: 16/465,237

(22) PCT Filed: Dec. 1, 2017

(86) PCT No.: PCT/IB2017/057576
§ 371 (c)(1),
(2) Date: May 30, 2019

(87) PCT Pub. No.: WO2018/100549
PCT Pub. Date: Jun. 7, 2018

(65) Prior Publication Data
US 2019/0345268 A1    Nov. 14, 2019

(30) Foreign Application Priority Data

Dec. 2, 2016  (IT) ................... 102016000122724

(51) Int. Cl.
| C08B 37/00 | (2006.01) |
| A61K 31/715 | (2006.01) |
| A61K 35/744 | (2015.01) |
| A61K 35/745 | (2015.01) |
| C12N 1/20 | (2006.01) |
| C12R 1/225 | (2006.01) |

(52) U.S. Cl.
CPC ........ *C08B 37/0063* (2013.01); *A61K 31/715* (2013.01); *A61K 35/744* (2013.01); *A61K 35/745* (2013.01); *C12N 1/205* (2021.05); *C12R 2001/225* (2021.05)

(58) Field of Classification Search
None
See application file for complete search history.

(56) References Cited

U.S. PATENT DOCUMENTS

| 6,770,246 | B1 | 8/2004 | Husek |
| 7,510,734 | B2 | 3/2009 | Sullivan et al. |
| 11,400,124 | B2 | 8/2022 | Biffi |
| 2002/0090416 | A1 | 7/2002 | Connolly |
| 2003/0031659 | A1 | 2/2003 | Farmer |
| 2003/0092163 | A1 | 5/2003 | Collins et al. |
| 2003/0157146 | A1 | 8/2003 | Rautonen et al. |
| 2003/0190369 | A1 | 10/2003 | Lovett |
| 2004/0170617 | A1 | 9/2004 | Finegold |
| 2005/0196480 | A1 | 9/2005 | Sullivan et al. |
| 2006/0057704 | A1* | 3/2006 | Schlothauer ............. A61P 1/04 435/252.9 |
| 2008/0081035 | A1 | 4/2008 | Parmely et al. |
| 2008/0193603 | A1 | 8/2008 | Hayes et al. |
| 2009/0061446 | A1 | 3/2009 | Niimi et al. |
| 2009/0098088 | A1 | 4/2009 | Taylor et al. |
| 2009/0220481 | A1 | 9/2009 | Maes et al. |
| 2009/0312282 | A1 | 12/2009 | Yoshida et al. |
| 2010/0074994 | A1 | 3/2010 | Harel et al. |
| 2010/0112564 | A1 | 5/2010 | Zhao et al. |
| 2011/0014167 | A1 | 1/2011 | Bindels et al. |
| 2011/0038837 | A1 | 2/2011 | Nishida et al. |
| 2011/0052538 | A1 | 3/2011 | Brown et al. |
| 2011/0166100 | A1 | 7/2011 | Wu |
| 2011/0305744 | A1 | 12/2011 | Russo |
| 2012/0251512 | A1 | 10/2012 | Farmer et al. |
| 2012/0269865 | A1 | 10/2012 | Roughead et al. |
| 2012/0301451 | A1 | 11/2012 | Braenning et al. |
| 2012/0322773 | A1 | 12/2012 | Pravda |
| 2016/0296569 | A1 | 10/2016 | Guglielmetti et al. |
| 2016/0348155 | A1* | 12/2016 | Guglielmetti .......... C12Q 1/689 |
| 2017/0035816 | A1 | 2/2017 | Biffi |
| 2019/0192590 | A1 | 6/2019 | Biffi |
| 2019/0290706 | A1 | 9/2019 | Biffi et al. |
| 2021/0186075 | A1 | 6/2021 | Biffi et al. |
| 2021/0236565 | A1 | 8/2021 | Biffi |

FOREIGN PATENT DOCUMENTS

| CN | 1161795 | A | 10/1997 |
| CN | 1840206 | A | 10/2006 |
| CN | 101636173 | A | 1/2010 |
| CN | 102919922 | A | 2/2013 |
| CN | 108743851 | A | 11/2018 |

(Continued)

OTHER PUBLICATIONS

Zhang et al. Scientific Reports , pp. 1-13 Oct. 27, 2016 (Year: 2016).*
Balzaretti: "Exploring Lactobacillus paracasei probiosis and metabolic potential", University of Milan PhD thesis, 2015, pp. 1-132. (Year: 2015).*
Ausubel et al, Current Protocols in molecular biology, edited vols. 1 and 2. John Wiley & Sons, Inc., Media, PA,1994.
Ciucanu I. et al. "A simple and rapid method for the permethylation of carbohydrates"*Carbohydrate Research*,131(1984) pp. 209-217.
Collins M.N. and Birkinshaw C. "Hyaluronic acid based scaffolds for tissue engineering—A review", Carbohydrate Polymers 2013, 1262-1279.

(Continued)

*Primary Examiner* — Jana A Hines
*Assistant Examiner* — Khatol S Shahnan Shah
(74) *Attorney, Agent, or Firm* — Steinfl + Bruno LLP

(57) ABSTRACT

The present invention refers to exopolysaccharide molecules, conditioned media or compositions comprising said molecules or media. Moreover, the present invention refers to use of said exopolysaccharide molecules, conditioned media or compositions as prebiotic, preferably to boost immune system.

12 Claims, 8 Drawing Sheets
Specification includes a Sequence Listing.

(56) References Cited

FOREIGN PATENT DOCUMENTS

| | | | |
|---|---|---|---|
| EP | 1145643 A1 | 10/2001 | |
| EP | 2407532 A2 | 1/2012 | |
| JP | H0517363 A | 1/1993 | |
| JP | 2005508617 A | 4/2005 | |
| JP | 2005534315 A | 11/2005 | |
| JP | 2010512755 A | 4/2010 | |
| JP | 2010161944 A | 7/2010 | |
| JP | 2013515051 A | 5/2013 | |
| RU | 2182008 C1 | 5/2002 | |
| WO | 00/54788 A1 | 9/2000 | |
| WO | 2003/090763 A1 | 11/2003 | |
| WO | 2004/022727 A1 | 3/2004 | |
| WO | 2005/001109 A2 | 1/2005 | |
| WO | 2005/083122 A2 | 9/2005 | |
| WO | 2006/050479 A2 | 5/2006 | |
| WO | 2007/071815 A1 | 6/2007 | |
| WO | 2007/140621 A1 | 12/2007 | |
| WO | 2008/119012 A2 | 10/2008 | |
| WO | 2008/148798 A2 | 12/2008 | |
| WO | 2010/008272 A1 | 1/2010 | |
| WO | 2010/008278 A1 | 1/2010 | |
| WO | 2010/099824 A1 | 9/2010 | |
| WO | 2011/036539 A1 | 3/2011 | |
| WO | 2012/154738 A1 | 11/2012 | |
| WO | 2014/068338 A1 | 5/2014 | |
| WO | 2014/137211 A1 | 9/2014 | |
| WO | 2015/000972 A1 | 1/2015 | |
| WO | 2015/033304 A1 | 3/2015 | |
| WO | 2015/033305 A1 | 3/2015 | |
| WO | 2015/162570 A1 | 10/2015 | |
| WO | 2015/172191 A1 | 11/2015 | |
| WO | 2016/030320 A1 | 3/2016 | |
| WO | 2017/195182 A1 | 11/2017 | |
| WO | 2017/212433 A1 | 12/2017 | |
| WO | 2018/100549 A1 | 6/2018 | |
| WO | 2018/109520 A1 | 6/2018 | |
| WO | 2018/109730 A1 | 6/2018 | |
| WO | 2019/019961 A1 | 1/2019 | |
| WO | 2019/053604 A1 | 3/2019 | |
| WO | 2019/111189 A1 | 6/2019 | |
| WO | 2021/053636 A1 | 3/2021 | |
| WO | 2021/053639 A1 | 3/2021 | |
| WO | 2021/053641 A2 | 3/2021 | |
| WO | 2021/053642 A1 | 3/2021 | |
| WO | 2021/09022 8 A1 | 5/2021 | |
| WO | 2021/090228 A4 | 7/2021 | |

OTHER PUBLICATIONS

Communication pursuant to Article 94(3) EPC for EP Application No. 14790322.3 filed on Sep. 5, 2014 on behalf of SOFAR S.P.A. dated Jan. 31, 2020 8 pages.
De Souza M.M. et aJ. "Effects of budesonide and probiotics enemas on the systemic inflammatory response of rats with experimental coJitis", Acta Cirurgica Brasileira 2007, 22 (Supp 1. 1 ): 40-45.
Di Mario Francesco et al., "Use of mesalazine in diverticular disease." Journal of Clinical Gastroenterology. vol. 40, Suppl 3, Aug. 2006.
D'inca R. et al. Rectal administration of Lactobacillus Casei DG modifies flora composition and Toll-Like receptor expression in colonic mucosa of patients with mildulcerative colitis'\ Dig. Dis. Sci. 2011, 56: 1178-1187.
EFSA Journal, "Scientific Opinion on the maintenance of the list of QPS biological agents intentionally added to food and feed (2012 update)1" EFSA Journal2012; 10(12):3020. 84 pages.
European Food Safety Authority EFSA journal (2012) 10(6): 2723.
Evans S. "Clinical trial structures" *J Exp Stroke Transl Med*.Mar. 2011, pp. 1-16, 16 pages.
"Example Cross-Over Study Design (A Phase 11, Randomized, Double-Blind Crossover Study of Hypertena and Placebo in Participants with High Blookd Pressure)". ClinicalTrials.gov (2012).

Fakhari A. and Berkland C. "Applications and emerging trends of hyaluronic acid in tissue engineering, as a dermal filler and in osteoarthritis treatment", Acta Biomaterialia2013, 9, 7081-7092.
Fao and Who et al.; "Live microorganisms which, when administered in adequate amounts, confer a health benefit on the host", *World Health Organizations and Food Agriculture Organization.* 2001.
Farup et al., "Probiotics, Symptoms, and Gut Microbiota; What are the relations? A Randomized Controlled Trial in Subjects with Irritable Bowel Syndrome" Gastro Research and Practice, vol. 2012. 7 pages.
Ferrario et al. J. Nutrition (published online Sep. 3, 2014) 144: 1787-1796 (Year: 2014).
Final Office Action for U.S. Appl. No. 14/916,959, filed Mar. 4, 2016 on behalf of Sofar Spa. dated Jul. 23, 2019. 23 pages.
Final Office Action for U.S. Appl. No. 14/916,961, filed Mar. 4, 2016 on behalf of SOFAR S.P.Adated Jan. 2, 2020 16 pages.
Final Office Action for U.S. Appl. No. 14/916,961, filed Mar. 4, 2016 on behalf of SOFAR S.P.A. dated Mar. 13, 2018. 15 pages.
Final Office Action for U.S. Appl. No. 15/305,470, filed Oct. 20, 2016 on behalf of SOFAR SPA.dated Jan. 14, 2019. 10 pages.
Final Office Action for U.S. Appl. No. 14/916,959, filed Mar. 4, 2016 on behalf of SOFAR SPA.dated Apr. 20, 2018. 26 pages.
Fiorino et al., "P325 Efficacy and Safety of IBD98E, a Sodium Hyaluronate Topical Preparation, in the Induction of Clinical and Endoscopic Remission in Patients with Distal Ulcerative Colitis: An Open Label Study," United European Gastroenterology Journal: 1(1S) (A219).
Floch M.H. et al. "Recommendations for probiotic use—2011 Update", J. Clin.Gastroenterol.2011, 45: S168-S171.
Food and Agriculture Organization. Health and nutritional properties of probiotics in food including powder milk with live lactic acid bacteria.Oct. 2001: 34 pages.
Gerwig G. et al., "Determination of the absolute configuration of mono-saccharides in complex carbohydrates by capillary G.L.C." *Carbohydrate Research*,77(1979) pp. 1-7.
Gill et al., "Metagenomic Analysis of the Human Distal Gut Microbiome," Science 312: 1355-1359 (2006).
Guglielmetti S. et al., "TgaA, a VirB1-Like Component Belonging to a Putative Type IV Secretion System of Bifidobacterium bifidum MIMBb75" *Applied and Environmental Microbiology*,vol. 80, No. 17,Sep. 2014 pp. 5161-5169.
Gugliemetti et al., "Randomised clinical trial; Bifidobacterium bifidum MIMBb75 significatnly alleviates irritable bowel syndrome and improves quality of life, a double-blind, placebo-controlled study" Alimentary Pharmacology & Therapeutics, p. 1123-1132. 2011.
Havea P. "Protein interactions in milk protein concentrate powders" *International Dairy Journal*,vol. 16,2006, pp. 415-422.
International Search Report for International Application No. PCT/IB2014/064284 filed on Sep. 5, 2014 on behalf of SOFAR SPA. dated Jan. 26, 2015. 6 pages.
International Search Report for International Application No. PCT/IB2014/064285 filed on Sep. 5, 2014 on behalf of SOFAR SPA. dated Jan. 29, 2015. 4 pages.
International Search Report for International Application No. PCT/IB2017/052850 filed on May 15, 2017 on behalf of SOFAR SPA.dated Aug. 17, 2017. 4 pages.
International Search Report for International Application No. PCT/IB2017/053389 filed on Jun. 8, 2017 on behalf of SOFAR SPA. dated Oct. 6, 2017. 5 pages.
International Search Report for International Application No. PCT/IB2017/057576 filed on Dec. 1, 2017 on behalf of SOFAR SPA. dated Feb. 22, 2018. 5 pages.
International Search Report for International Application No. PCT/IB2017/057980 filed on Dec. 15, 2017 on behalf of SOFAR SPA.dated Mar. 19, 2018. 4 pages.
International Search report for International Application PCT/IB2015/052938 filed on Apr. 22, 2015 on behalf of SOFAR SPA.dated Jul. 31, 2015. 4 pages.
Italia II Ministero della Salute (*Linee Guida su Probiotici e Prebiotici rev.*May 2013).

(56) References Cited

OTHER PUBLICATIONS

Jacobsen et al., "Screening of Probiotic Activities of Forty-Seven Strains of Lactobacillus spp. By In Vitro techniques and Evaluation of the Colonization Ability of Five Selected Strains in Humans" Applied and Environmental Microbiology, Nov. 1999, p. 4949-4956. 8 pages.
Larsen et al., "Predominant genera of fecal microbiota in children with atopic dermatitis are not altered by intake of probiolic bacteria Lactobacillus acidophilus NCFM and Bifidobacterium animalis subsp. *lacis* Bi-07," FEMS Microbiol Ecol 75: 482-496 (2011).
LeBlanc et al., "Beneficial effects on host energy metabolism of shot-chain fatty acids and vitamins produced by commensal and probiotic bacteria," Microbial Cell Factories 16:79: 1-10 (2017).
Lombardo L; et al. "New insights into Lactobacillus and functional intestinal disorders", Minerva Gastroenterologica E Dietologica, Edizioni Minerva Medica, Torino, IT, vol. 54, No. 3. 2008.
Lombardo, Lucio et al., "Clinical Evaluation of Lactobacillus Paracasei Subsp. Paracasei F19 with Gluco-Oligosaccharides in the Short-term Treatment of Irritable Bowel Syndrome" Microbial Ecology in Health and Disease 21: 28-32 (2009).
Martin R. et al. "Role of commensal and probiotic bacteria in human health: a focus on inflammatory bowel disease", Microbial Cell Factories2013, 12: 71.
Matthes H. et al. "'Clinical trial: probiotic treatment of acute distal ulcerative colitis with rectally administered *Escherichia coli* Nissle I 917 (EcN)", BMC Complementaty and Alternative Medicine2010, 10: 13.
Mazzuoli S. et al. "Definition and evaluation of mucosal healing in clinical practice", Digestive and Liver Disease2013, 45, 969-977.
Michail et al., "Gut Microbiota is Not Modified by Randmized, Double-Blind, Placebo-Controlled Trial of VSL #3 in Diarrhea-Predominant Irritable Bowel Syndrome". (Probiotics & Antimicro Prot. (2011) 3:1-7).
Milani et al., Assessing the fecal microbiota: and optimized ion torrent 16S rRNA gene-based analysis protocol. PLoS One. 2013; 8(7); e68739, 12 pages. Published2013.
Montalto M. et al., "Clinical trial: the effects of a probiotic mixture on non-steroidal anti-inflammatory drug enteropathy—a randomized, double-blind, cross-over, placebo-controlled study" Aliment Pharmacol Ther,2010, pp. 209-214, 6 pages.
Muyzer et al., "Profiling of Complex Microbial Populations by Denaturing Gradient Gel Electrophoresis Analysis of Polymerase Chain Reaction-Amplified Genes Coding for 16S rRNA," Applied and Environmental Microbiology 59:595-700(1993).
Necas J. et al. "Hyaluronic acid (hyaluronan): a review", Veterinarni Medicina, 2008, 53(8): 397-411.
Non-Final Office Action for U.S. Appl. No. 14/916,961, filed Mar. 4, 2016 on behalf of SOFAR S.P.A.dated Jun. 30, 2017. 21 pages.
Non-Final Office Action for U.S. Appl. No. 14/916,961, filed Mar. 4, 2016 on behalf of SOFAR S.P.A.dated Jul. 25, 2019. 18 pages.
Non-Final Office Action for U.S. Appl. No. 15/305,470, filed Oct. 20, 2016 on behalf of SOFAR SPA.dated Aug. 22, 2019. 8 pages.
Non-Final Office Action for U.S. Appl. No. 16/301,361, filed Nov. 13, 2018 on behalf of SOFAR S.P.A.dated May 8, 2020 20 pages.
Non-Final Office Action for U.S. Appl. No. 14/916,959, filed Mar. 4, 2016 on behalf of SOFAR S.P.A.dated Mar. 13, 2020 25 pages.
Non-Final Office Action for U.S. Appl. No. 14/916,959, filed Mar. 4, 2016 on behalf of SOFAR SPA.dated Aug. 31, 2017. 27 pages.
Non-Final Office Action for U.S. Appl. No. 14/916,959, filed Mar. 4, 2016 on behalf of Sofar SPA. dated Nov. 19, 2018. 15 pages.
Non-Final Office Action for U.S. Appl. No. 15/305,470, filed Oct. 20, 2016 on behalf of SOFAR SPA.dated Mar. 26, 2018. 10 pages.
Office Action in corresponding Chinese Patent Application No. 201480049296.4, dated Aug. 27, 2019.
Office Action in Corresponding Japanese Patent Application No. 2016-564193, dated Apr. 2, 2019.
Okuda et al., "Virtual metagenome reconstruction from 16S rRNA gene sequences".*Nature Communications*,2012. 8 pages.

Oliva S. et al. "Randomised clinical trial: the effectiveness of Lactobacillus Reuteri ATCC 55730 rectal enema in children with active distal ulcerative colitis", Aliment. Pharmacol. Ther.2012, 35: 327-334.
Olveira et al.; "Lactobacillus paracasei Reduces Intestinal Inflammation in Adoptive Transfer Mouse Model of Experimental Colitis", Clinical and Developmenta Immunology, vol. 23, No. 5, Jan. 1, 2011, pp. 1077-13.
Orlando A. et al. "Clinical implications of mucosal healing in the management of patients with inflammatory bowel disease", Digestive and Liver Disease2013, 45, 986-991.
Plant et al., "Association of *Laclobacillus* spp. with Peyer's Patches in Mice", Clinical and Diagnostic Laboratory Immunology 8: 320-324 (2001).
Price R.D. et al. "Hyaluronic acid: the scientific and clinical evidence", Journal ofPlastic, Reconstructive & Aesthetic Surgery2007, 60: 1110-1119.
Restriction Requirement for U.S. Appl. No. 14/916,961, filed Mar. 4, 2016 on behalf of SOFAR S.P.A.dated May 10, 2019. 7 pages.
Sambrook et al. Molecular cloning: A Laboratory Manual. 3rd ed., vols. 1,2 and 3 cold Spring Harbor Laboratory Press,2001, 2100 pp.
Sasaki M. et al., "Transglucosidase improves the gut microbiota profile of type 2 diabetes mellitus patients: a randomized double-blind, placebo-controlled study" *BMC Gastroenterology*, 13:81,2013.
Saving et al., "Laclobacillus reuteri DSM 17938 in Infantile Colic: A Randomized, Double-Blind, Placebo-Controlled Trial", Pediatrics 126: e526-e533 (2010).
Scaldaferri F. et al. "Gut microbial flora, prebiotics and probiotics in IBD: their current usage and utility", BioMed Research International2013, 9 pages.
Siew Chien Ng et al., "Effect of probiotic bacteria on the intenstinal microbiota in irritable bowel syndrome" Journal of gastroenterology and hepatology.2013.
Spiller et al., "Randomized double blind placebo-controlled trial of *Saccharomyces cerevisiae* CNCM i-3856 in irritable bowel syndrome: improvement in abdominal pain and bloating in those with predominant constipation" United European Gastroenterology Journal. 2016.
Stuknyte M. et al., "Potential immunomodulatory activity of bovine casein hydrolysates produced after digestion with proteinases of lactic acid bacteria" *International Dairy Journal*, 21(2011) pp. 763-769.
Taverniti and Gugliemetti et al., "The immunomodulatory properties of probiotic microorganisms beyond their viability (ghost probiotics: proposal of paraprobiotic concept)" Department of Food Science and Microbiolgy (DiSTAM), , 6:261-274(2011).
Turnbaugh et al., "The Effect of Diel on the Human Gut Microbiome: A Metagenomic Analysis in Humanized gnolobiotic Mice," Sci Transl Med: (2009).
Tursi et al., "Balsalazide and/or high-potency probiotic mixture (VSL#3) in maintaining remission after attack of acute, uncomplicated diverticulitis of the colon", International Journal of Colorectal Disease; Clinical and Molecular Gastroenterology an Surgery, Sprinter, Berlin, DE. vol. 22, No. 9,Mar. 28, 2007. pp. 1103-1108.
Tursi et al., "Effect of Lactobacillus easel supplementation on the effectiveness and tolerability of a new second-line 10-day quadruple therapy after failure of a first attempt to cure Helicobacter pylori infection," Med Sci Monit 10: CR662-666 (2004).
Tursi et al., "Mesalazine and/or Lactobacillus Casei in maintaining Long-term Remission of Symptomatic Uncomplicated Diverticular Disease of the Colon" Original Paper. Hepato-Gastroenterology. 2008, 55; 916-920.
Tursi et al., "Mesalazine and/or Lactobacillus casei in preventing recurrence of symptomatic uncomplicated diverticular disease of the colon: A Prospective , randomized, open-label study", Journal of Clinical Gastroenterol, Raven Press Ltd, NY, New York. vol. 40, No. 2, Apr. 1, 2006. pp. 312-316.
Tursi et al., "Randomised clinical trial: mesalazine and/or probiotics in maintaining remission of symptomatic uncomplicated diverticula disease—double-blind, randomized, placebo-controlled study" Alimentary Pharmacology & Therapeutics. vol. 38, No. 7.Oct. 19, 2013. pp. 741-751.

(56) References Cited

OTHER PUBLICATIONS

U.S. National Library of Medicine, "Effect of Lactobacillus Casei DG (Enterolactis Plus) in Patient with irritable Bowel Syndrome: a Pilot Study", ClinicalTriaals.gov,Feb. 11, 2015.
U.S. National Library of Medicine Efficacy Evaluation of a Commercial Preparation Containing Lactobacillus Casei DG on the Reduction of the Painful Symptoms Related to the Irritable Bowel Syndrome (IBS).*A Pilot Clinical Study*.Feb. 28, 2014.
Valerio et al., "Effects of Probiotic Lactobacillus paracasei-enriched Artichokes on Constipated Patients", J Clin Gastroenterol,Sep. 10, 2010.
Vernia et al. Dig. Disease Sci. (1988) 33(11): 1353-135 (Year: 1988).
"Why VSL#3" (Obtained from https://vsl3.com/hcp/vsl-info on Aug. 22, 2017, 4 pages.
Worthley et al. "A human, double-blind, placebo-controlled, crossover trial of prebiotic, probiotic, and symbiotic supplementation: effects on luminal, inflammatory, epigenetic, and epithelial biomarkers of colorectal cancer" (Am J Clin Nutr 2009; 90; 578-86).
Written Opinion for International Application No. PCT/IB2014/064284 filed on Sep. 5, 2014 on behalf of SOFAR SPA.dated Jan. 26, 2015. 7 pages.
Written Opinion for International Application No. PCT/IB2014/064285 filed on Sep. 5, 2014 on behalf of SOFAR SPA. dated Jan. 29, 2015. 7 pages.
Written Opinion for International Application No. PCT/IB2017/052850 filed on May 15, 2017 on behalf of SOFAR SPA.dated Aug. 17, 2017. 6 pages.
Written Opinion for International Application No. PCT/IB2017/053389 filed on Jun. 8, 2017 on behalf of SOFAR SPA.dated Oct. 6, 2017. 7 pages.
Written Opinion for International Application No. PCT/IB2017/057576 filed on Dec. 1, 2017 on behalf of SOFAR SPA.dated Feb. 22, 2018. 8 pages.
Written Opinion for International Application No. PCT/IB2017/057980 filed on Dec. 15, 2017 on behalf of SOFAR SPA. dated Mar. 19, 2018. 8 pages.
Written Opinion for International Application PCT/IB2015/052938 filed on Apr. 22, 2015 on behalf of SOFAR SPA.dated Jul. 31, 2015. 5 pages.
Zheng, L. et al. "Regulation of colonic epithelial repair in mice by toll-like receptors and hyaluronic acid," Gastroenterology2009:137 2041-2051.
Australian Examination Report for AU Application No. 2017263294 filed on May 15, 2017 on behalf of SOFAR S.P.A. dated Oct. 30, 2020 5 pages.
Balzaretti S. et al., "A novel hetero-exopolysaccharide mediates the recognition of Lactobacillus paracasei DG by the immune system" Pharmabiotics Conference 2015, Paris, Oct. 29-30, 2015,1 page.
Bienenstock J et al., "New insights into probiotic mechanisms" *Gut Microbes*, vol. 4 Issue 2,Apr. 2013, 7 pages.
Canadian Examination Search Report for CA Application No. 2,923,390 filed on Sep. 5, 2014 on behalf of SOFAR S.P.A. dated Jan. 26, 2021 4 pages.
Chinese Decision of Rejection for CN Application No. 201480049296.4 filed on Sep. 5, 2014 on behalf of SOFAR S.P.A. dated Dec. 9, 2020 (English + Original) 12 pages.
Colombian Office Action for CO Application No. NC2018/0010954 filed on Nov. 1, 2018 on behalf of SOFAR S.P.A. dated Feb. 5, 2021 9 pages (Partial English + Original).
Colombian Office Action for CO Application No. NC2019/0007116 filed on Jul. 2, 2019 on behalf of SOFAR S.P.A. dated Jan. 15, 2021 19 pages (English + Original).
Communication pursuant to Article 94(3) EPC for EP Application No. 14790322.3 filed on Septembers, 2014 on behalf of SOFAR S.P.A. dated Jan. 11, 2021 3 pages.
Cui Y. et al., "Revolution of Chronic Diarrhoea" China Medicine, Science, and Technology Publishing House, 1st edition, Jan. 2013, pp. 19-23 (Original + Partial Google Translation) 14 pages.

Declaration for the self-archiving of the doctoral thesis for "Exploring Lactobacillius Paracasei Probiosis and Metabolic Potential" by Balzaretti, Silvia dated Nov. 20, 2015 4 pages (English + Original).
Israeli Office Action for IL Application No. 244391 filed on behalf of SOFAR S.P.A. dated Oct. 27, 2020 (English + Original) 4 pages.
Kay, RM., et al., "Dietary Fiber," J. of Lipid Research, v. 23, 1982. 221-242, 22 Pages.
Laws A. et al., "Determination of the structure and molecular weights of the exopolysaccharide produced by Lactobacillus acidophilus 5e2 when grown on different carbon feeds." *Carbohydr Res*.Feb. 4, 2008;343(2):301-7.
Non-Final Office Action for U.S. Appl. No. 14/916,961, filed Mar. 4, 2016, on behalf of SOFAR S.P.A. dated Jan. 7, 2021. 22 Pages.
Notice of Allowance for U.S. Appl. No. 16/301,361, filed Nov. 13, 2018 on behalf of SOFAR S.P.A. dated Feb. 1, 2021 8 pages.
Paoluzi O.A., et al. "Low efficacy of levofloxacin-doxycycline-based third-line tripletherapy for Helicobacter pylori eradication in Italy." *World Journal of Gastroenterology*21: 6698-705,Jun. 2015.
Rosania R. et al. "Effect of probiotic or prebiotic supplementation on antibiotic therapy in the small intestinal bacterial overgrowth: a comparative evaluation." Curr Clin Pharmacol. May 2013;8(2):169-72. 5 pages.
Screenshot from the web-archive of the Milano University, Nov. 23, 2015, 2 pages (English + Original).
Wang Y. et al., "Emerging Infectious Diseases" Science and Technology Documents Publishing House, 1st edition, Jan. 2006, pp. 310-312 (Original + Partial Google Translation) 12 pages.
Watanabe I. et al., "KT-11" *Food Style*21, vol. 17, No. 6, pp. 62-64,2013. 10 pages. (Machine Translation + Original).
Mexican Office Action for MX Application No. MX/a/2016/002766 filed on Sep. 5, 2014 on behalf of SOFAR S.P.A. dated Mar. 18, 2021 10 pages (English + Original).
Aden K. et al., "Metabolic Functions of Gut Microbes Associate with Efficacy of Tumor Necrosis Factor Antagonists in Patients with Inflammatory Bowel Diseases" Gastroenterology, 2019, pp. 1279-1292.
Allegretti J. et al., "Short Chain Fatty Acid Profiles Are Altered by Fecal Microbiota Transplantation for the Treatment of Inflammatory Bowel Disease and Recurrent Clostridioides difficile Infection" *Gastroenterology*,2019, 2 pages.
Balzaretti S. et al., "The vaginal isolate Lactobacillus paracasei LPC-S01 (DSM 26760) is suitable for oral administration" Frontiers in Microbiology, vol. 6, art. 952,Sep. 2015 , 13 pages.
Banasiewicz T. et al., "Determination of butyric acid dosage based on clinical and experimental studies—a literature review" *Gastroenterology Review*,2020, pp. 119-125.
Borren N. et al., "Alterations in Fecal Microbiomes and Serum Metabolomes of Fatigues Patients With Quiescent Inflammatory Bowel Diseases" *Clinical Gastroenterology and Hepatology*,Mar. 2020, 35 pages.
Canadian Office Action for CA Application No. 2,923,392 filed on Sep. 5, 2014 on behalf of SOFAR S.P.A. dated Jun. 1, 2020 4 pages.
Cassard L. et al., "Individual strains of Lactobacillus paracasei differentially inhibit human basophil and mouse mast cell activation," Immunity, Inflammation, and Disease vol. 4, Issue 3., 2016. 11 Pages.
Chassard C. et al., "Functional dysbiosis within the gut microbiota of patients with constipated-irritable bowel syndrome" *Alimentary Pharmacology and Therapeutics*,2012, pp. 828-838.
Chilean Office Action for CL Application No. 201803193 filed on Sep. 5, 2014 dated Apr. 16, 2020 16 pages (English + Original).
Chinese Office Action for CN Application No. 201480049288 filed on Sep. 5, 2014 on behalf of SOFAR S.P.A. dated Sep. 16, 2020 8 pages (English + Original).
Colombian Office Action for CO Application No. NC2018/0010950 filed on Sep. 5, 2014 on behalf of SOFAR S.P.A. dated Jul. 27, 2020 11 pages (Partial English + Original).
Compare D. et al., "Lactobacillus casel DG and its postbiotic reduce the inflammatory mucosal response: an ex-vivo organ culture model of post-infectious irritable bowel syndrome" *BMC Gastroenterology*,2017, 8 pages.
Costalos et al., "Enteral feeding of premature infants with *Saccharomyces boulardii*" *Early Human Development*, 74,(2003), 89-96.

(56) References Cited

OTHER PUBLICATIONS

Cremon C. et al., "Effect of Lactobacillus paracasei CNCM 1-1572 on symptoms, gut microbiota, short chain fatty acids, and immune activation in patients with irritable bowel syndrome: A pilot randomized clinical trial" UEG Journal, Sep. 2017, 10 pages.

Eurasian Notification of Grant for Application No. 201690464/28 filed on Sep. 5, 2014 on behalf of SOFAR S.P.A. dated Jun. 9, 2020 2 pages (English + Original).

Final Office Action for U.S. Appl. No. 14/916,959, filed Mar. 4, 2016 on behalf of SOFAR S.P.A. dated Aug. 21, 2020 48 pages.

Final Office Action for U.S. Appl. No. 15/305,470, filed Oct. 20, 2016 on behalf of SOFAR S.P.A. dated Jul. 10, 2020 21 pages.

Final Office Action for U.S. Appl. No. 16/301,361, filed Nov. 13, 2018 on behalf of SOFAR S.P.A. dated Sep. 21, 2020 11 pages.

Gargari G. et al., "Fecal Clostridiales distribution and short-chain fatty acids reflect bowel habits in irritable bowel syndrome" Environmental Microbiology, Sep. 2018, 31 pages.

Hustoft T. et al., "Effects of varying dietary content of fermentable short-chain carbohydrates on symptoms, fecal microenvironment, and cytokine profiles in patients with irritable bowel syndrome" Neurogastroenterology & Motility, Sep. 2016, 9 pages.

Irritable Bowel Syndrome—Wikipedia, dated Sep. 16, 2020. 33 pages, https://en.wikipedia.org/wiki/Irritable_bowel_syndrome.

Israeli Office Action for Application No. 244391 filed on Mar. 2, 2016 on behalf of SOFAR S.P.A. dated Jun. 24, 2020 4 pages (English + Original).

Israeli Office Action for Application No. 269107 filed on Sep. 3, 2019 on behalf of SOFAR S.P.A. dated May 17, 2020 5 pages (English + Original).

Japanese Office Action for JP Application No. 2016564193 filed on Apr. 22, 2015 on behalf of SOFAR S.P.A. dated Feb. 18, 2020 11 pages (English + Original).

Langhorst J. et al., "Distinct patterns of short-chain fatty acids during flare in patients with ulcerative colitis under treatment with mesalamine or a herbal combination of myrrh, chamomile flowers, and coffee charcoal: secondary analysis of a randomized controlled trial" European Journal of Gastroenterology & Hepatology, Feb. 2020, 6 pages.

Magnusson M. et al., "The Anti-inflammatory Immune Regulation Induced by Butyrate is Impaired in Inflamed Intestinal Mucosa from Patients with Ulcerative Colitis" Inflammation, Apr. 2020, 11 pages.

Mcfarland, et al., "Strain-Specificity and Disease-Specificity of Probiotic Efficacy: A Systematic Review and Meta-Analysis," Frontiers in Medicine, May 7, 2018. 14 Pages.

Mexican Office Action for MX Application No. MX/a/2016/002766 filed on Sep. 5, 2014 on behalf of SOFAR S.P.A. dated Aug. 13, 2020 10 pages (English + Original).

Pituch A. et al., "Butyric acid in functional constipation" Przeglad Gastroenterologiczny,2013, 4 pages.

Pozuelo M. et al., "Reduction of butyrate and methane producing microorganisms in patients with Irritable Bowel Syndrome" Nature Scientific Reports, Apr. 2015, 12 pages.

Ralf Jager et al., "Probiotic Administration Increases Amino Acid Absorption from Plant Protein: a Placebo-Controlled, Randomized, Double-Blind, Multicenter, Crossover Study," Probiotics and Antimicrobial Proteins, 2020. 10 Pages.

Ringel-Kulka T. et al., "Short Chain Fatty Acids and Intestinal Transit in Patients With Irritable Bowel Syndrome and Healthy Controls" AGA Abstracts,May 2012, 1 page.

Scarpellini E. et al., "Efficacy of butyrate in the treatment of diarrhea-predominant irritable bowel syndrome" Digestive and Liver Disease, 2007, 4 pages.

Shi Y. et al., "Function and clinical implications of short-chain fatty acids in patients with mixed refractory constipation" Association of Coloproctology of Great Britain and Ireland, Feb. 2016, 8 pages.

Smokvina T. et al. "Lactobacillus paracasei Comparative Genomics: Towards Species Pan-Genome Definition and Exploitation of Diversity," Plos One, Jul. 19, 2013. 16 Pages.

Sun Q. et al., "Alterations in fecal short-chain fatty acids in patients with irritable bowel syndrome" Systematic Review and Meta-Analysis,Jan. 2019, 12 pages.

Third Chinese Office Action for CN Application No. 201480049296.4 filed on Sep. 5, 2014 on behalf of SOFAR S.P.A. dated Mar. 18, 2020 13 pages (English + Original).

Turco F. et al., Bacterial stimuli activate nitric oxide colonic mucosal production in diverticular disease. Protective effects of L. casei DG (Lactobacillus paracasei CNCM I-1572) UEG Journal, Nov. 2016, 10 pages.

Turco F. et al., "Enteroglial-derived S100B protein integrates bacteria-induced Toll-like receptor signalling in human enteric glial cells" GUT Neurogastroenterology, vol. 63, Mar. 2014, Originally Published online Jan. 3, 2013, 12 pages.

Tursi A. et al., "Assessment of Fecal Microbiota and Fecal Metabolome in Symptomatic Uncomplicated Diverticular Disease of the Colon" J. Clin Gastroenterol,Oct. 2016, 4 pages.

Tursi A. et al., "Fecal Microbiota, Fecal and Urinary Metabolic Profiling and Symptomatic Uncomplicated Diverticular Disease of the Colon" Digestive and Liver Disease, 2017, 1 page.

Tursi A. et al., "Natural History of Symptomatic Uncomplicated Diverticular Disease: A 13-Year Prospective Study" AGA Abstracts, Apr. 2017, 1 page.

Zhuang M. et al., "Abundance of probiotics and butyrate-production microbiome manages constipation via short-chain fatty acids production and hormones secretion" Molecular Nutrition & Food Research, Jul. 2019, 41 pages.

Zhuang M. et al., "Systematic Review and Meta-analysis: Short-Chain Fatty Acid Characterization in Patients With Inflammatory Bowel Disease" Inflammatory Bowel Disease, Nov. 2019, 13 pages.

Brussow H. "Problems with the concept of gut microbiota dysbiosis" Microbial Biotechnology, vol. 13(2), 2020, pp. 423-434.

Koebnick C. et al., "Probiotic beverage containing Lactobacillus casei Shirota improves gastrointestinal symptoms in patients with chronic constipation" Can J Gastroenterol, vol. 17 No. 11, Nov. 2003, pp. 655-658.

Non-Final Office Action for U.S. Appl. No. 14/916,959, filed Mar. 4, 2016 on behalf of SOFAR S.P.A. dated Apr. 13, 2021 33 pages.

Non-Final OfficeAction for U.S. Appl. No. 16/308,330, filed Dec. 7, 2018 on behalf ofSOFAR S.P.A. dated Apr. 30, 2021.38 Pages .

Notice of Allowance for U.S. Appl. No. 16/301,361, filed Nov. 13, 2018 on behalf of SOFAR S.P.A. dated May 3, 2021 9 pages.

Tuohy K.M. et al., "Survivability of a probiotic Lactobacillus casei in the gastrointestinal tract of healthy human volunteers and its impact on the faecal microflora" Journal of Applied Mircrobiology, 2007, pp. 1026-1032.

Balzaretti et al., "A novel rhamnose-rich hetero-exopolysaccharide isolated from Lactobacillus paracasei DG activates THP-1 human monocytic cells," Applied and Environmental Microbiology 83:1-28 (2017).

Balzarettyi, "Exploring Lactobacillus paracasei probiosis and metabolic," PhD Thesis; PhD Programme in Food Science, Technology and Biotechnology; Graduate School in Molecular Science and Plant, Food and Environmental Biotechnology; Universita Degli Studi Di Milano (2014-2015).

Laws et al., "Biosynthesis, characterisation, and design of bacterial exopolysaccharides from lactic and acid bacteria," Biotechnology Advances 19: 597-625 (2001).

Neiwert et al., "Structural investigation of rhamnose-rich polysaccharides from Streptococcus dysgalactiae bovine mastitis isolate," Carbohydrate Research 389: 192-195 (2014).

Polak-Berecka et al., "Physicochemical characterization of exopolysaccharides produced by Lactobacillus rhamnosus on various carbon sources," Carbohydrate Polymers 117: 501-509 (2015).

Sanilbaba et al., "Exopolysaccharides Production by Lactic Acid Bacteria," Applied Microbiology: Open Access 2:1-5(2016).

Vinogradov et al., "Structural studies of the rhamnose-rich cell wall polysaccharide of Lactobacillus casei BL23," Carbohydrate Research 435: 156-161 (2016).

Zhang et al.,"Isolated exopolysaccharides from Lactobacillus rhamnosus GG alleviated adipogenesis mediated by TLR2 in mice," Scientific Reports 6: 1-14 (2016).

(56) References Cited

OTHER PUBLICATIONS

Allowance of the Brazilian patent application BR 11 2016 005059 2 published in the Official Bulletin n° 2651 dated Oct. 26, 2021 (Portuguese Only).
Australian Examination Report for AU Application No. 2017367302 filed on Dec. 1, 2017 on behalf of SOFAR S.P.A. dated Jul. 23, 2021 4 pages.
Bacteriotherapy—Merriam-Webster Medical Dictionary, Archive Date: Apr. 26, 2016, 6 pages.
Bassi R. "Mesalazine + Lactobacillus paracasei CNCMI1572 vs Mesalazine alone in preventing recurrence of symptom of diverticular disease: a prospective, randomize, open-label study." *Colorectal Disease*, 2019 1 pages.
Bassi R. "Preventing recurrence of symptomatic diverticular disease of the colon: mesalazine with or without Lactobacillus case DG: a prospective randomized, open label study." European Society of Coloproctology, 2015, 1 page.
Canadian Office Action for CA Application No. 2,923,392 filed on Sep. 5, 2014 on behalf of SOFAR S.P.A. dated Apr. 1, 2021 4 pages.
Canani R. B. et al., "Potential beneficial effects of butyrate in intestinal and extraintestinal diseases" World Journal of Gastroenterology, vol. 17 No. 12, Mar. 2011, 10 pages.
Capsule (Pharmacy)—Wikipedia, the free encyclopedia, Archive Date: Apr. 10, 2016, 4 pages.
Chilean Office Action for CL Application No. 201901493 filed on Dec. 1, 2017 on behalf of SOFAR S.P.A. dated May 6, 2021 24 pages (English + Original).
Chinese Office Action for CN Application No. 201480049288X filed on Sep. 5, 2014 on behalf of SOFAR S.P.A. dated Aug. 12, 2021 (English + Original) 15 pages.
Chooi E. et al., "Chronic atrophic gastritis is a progressive disease: analysis of medical reports from Shanghai (1985-2009)" Singapore Med J, 2012, 53 (5), pp. 318-324.
Colledge H. "Atrophic Gastritis: Causes. Symptoms, & Treatment" *Healthline*, Sep. 2018, 5 pages.
Colombian Office Action for CO Application No. NC2018/0010950 filed on May 15, 2017 on behalf of SOFAR S.P.A. dated May 3, 2021 9 pages (English + Original).
Colombian Office Action for CO Application No. NC2018/0010954 filed on Jun. 2, 2019 on behalf of SOFAR S.P.A. dated Jun. 30, 2021 8 pages (Partial English + Original).
Colombian Office Action for CO Application No. NC2019/0007116 filed on Jul. 2, 2019 on behalf of SOFAR S.P.A. dated Sep. 29, 2021 12 pages (English + Original).
Colombian Office Action for Colombian Application No. NC2019/0006257 filed on Dec. 15, 2017 on behalf of SOFAR S.P.A. dated May 13, 2021 3 pages (English + Original).
Communication pursuant to Article 94(3) EPC for EP Application No. 17817173.2 filed on Dec. 1, 2017 on behalf of SOFAR S.P.A. dated Sep. 29, 2021 6 pages.
De Backer A. I. et al., "Intestinal stenosis from mesenteric injury after blunt abdominal trauma" Eur. Radiol., 1999, pp. 1429-1431.
Dore J. et al., "The Human Intestinal Microbiota; From Phylogenetics to Functional Metagenomics" *Old Herborn University*, 2010, pp. 15-26.
Dysbiosis—Wikipedia, the free encyclopedia, Dated: Mar. 31, 2014 https://web.archive.org/web/20140331225522/http://en.wikipedia.org/wiki/Dysbiosis , 4 pages.
Eurasian Office Action for EA Application No. 202090097/28 filed on Sep. 5, 2014 on behalf of SOFAR S.P.A. dated Aug. 16, 2021 (English + Original) 10 pages.
Ferrario, et al., "Modulation of Fecal Clostridiales Bacteria and Butyrate by Probiotic Intervention with Lactobacillus paracasei DG Varies among Healthy Adults1-3" J. Nutritional Epidemiology, 144. Sep. 3, 2014. pp. 1787-1796. 10 Pages.
Final Office Action for U.S. Appl. No. 14/916,959, filed Mar. 4, 2016 on behalf of SOFAR S.P.A. dated Dec. 29, 2021. 29 Pages.
Final Office Action for U.S. Appl. No. 14/916,961, filed Mar. 4, 2016, on behalf of SOFAR S.P.A. dated Oct. 14, 2021. 26 Pages.

Gould M. et al., "Diabetic diarrhea" Current Gastroenterology Report, 2009, pp. 354-359 (Abstract only).
Gould, M., et al., "Diabetic Diarrhea," Current Gastroenterology Reports, 11: 354-359. Full paper. 2009. 7 Pages.
Haenel H. "Human Normal and Abnormal Gastrointestinal Flora" *American Journal of Clinical Nutrition*, vol. 23 No. 11, Nov. 1970, pp. 1433-1439.
Iebba V. et al., "Eubiosis and Dysbiosis: the two sides of the microbiota" *New Microbiologica*, vol. 39, 2016, pp. 1-12.
Jarbrink-Sehgal M. E. et al., "Symptomatic Diverticulosis is Characterized by Loose Stools" *Clinical Gastroenterology and Hepatology*, 14: 1763-1770, Dec. 2016, 9 pages.
John Hopkins Medicine—Fecal Transplantation (Bacteriotherapy), John Hopkins Division of Gastroenterology and Hepatology, Archive Date: Apr. 2016, 2 pages.
Laval G. et al., "The use of steroids in the management of inoperable intestinal obstruction in terminal cancer patients: do they remove the obstruction?" Palliative Medicine, 2000, pp. 3-10.
Leonel, A.J., et al. "Butyrate: implications for intestinal function," Current Opinion in Clinical Nutrition and Metabolic Care 15(5): 474-479. 2012. 6 Pages.
Mangili G. et al., "Palliative care for intestinal obstruction in recurrent ovarian cancer: a multivariate analysis" *BMJ Journals*, 2005, 5 pages (Abstract Only).
Miceli E. et al., "Common Features of Patients with Autoimmune Atrophic Gastritis" *Clinical Gastroenterology and Hepatology*, 2012, pp. 812-814.
Non-Final Office Action for U.S. Appl. No. 16/467,797, filed Jun. 6, 2019 on behalf of SOFAR S.P.A. dated Dec. 14, 2021 35 pages.
Notice of Allowance for U.S. Appl. No. 15/305,470, filed Oct. 20, 2016 on behalf of SOFAR S.P.A. dated Jun. 1, 2021 15 pages.
Notice of Allowance for U.S. Appl. No. 15/305,470, filed Oct. 20, 2016, on behalf of SOFAR SPA. dated Nov. 3, 2021. 8 Pages.
Notice of Allowance for U.S. Appl. No. 15/305,470, filed Oct. 20, 2016, on behalf of SOFAR SPA. dated Sep. 8, 2021. 8 Pages.
Notice of Allowance for U.S. Appl. No. 16/301,361, filed Nov. 13, 2018, on behalf of SOFAR S.P.A. dated Aug. 4, 2021. 11 Pages.
Restriction Requirement for U.S. Appl. No. 16/467,797, filed Jun. 7, 2019 on behalf of SOFAR S.P.A. dated Jun. 15, 2021 6 pages.
Restriction Requirement for U.S. Appl. No. 17/090,669 filed on Nov. 5, 2020, on behalf of SOFAR S.P.A. dated Sep. 3, 2021. 7 Pages.
Rodriguez-Castro K. I. et al., "Clinical manifestations of chronic atrophic gastritis" Acta Biomed, vol. 89, 2018, pp. 88-92.
Salvetti E. et al., "The Genus *Lactobacillus*: A Taxonomic Update" *Probiotics & Antimicro. Prot.*, Nov. 2012, vol. 4, pp. 217-226.
Scarpignato C. et al., "Management of colonic diverticular disease in the third millennium: Highlights from a symposium held during the United European Gastroenterology Week 2017" Therapeutic Advances in Gastroenterology, vol. 11, Mar. 2018, pp. 1-21.
Tsimmerman Y. S. "Eubiosis and Dysbiosis of Gastrointestinal Tract: Myths and Reality" *Perm State Medical Academy*, 2013, 27 pages.
Wells D. "Gastritis Diet: What to Eat and What to Avoid" Healthline, Jul. 2020, 11 pages.
World Gastroenterology Organisation Global Guidelines "Probiotics and prebiotics" Feb. 2017, 35 pages.
Canadian Office Action for CA Application No. 2,923,390 filed on Sep. 5, 2014 on behalf of SOFAR S.P.A. dated Nov. 29, 2021 5 pages.
Chinese Office Action for CN Application No. 201780029401.1 filed on May 15, 2017 on behalf of SOFAR S.P.A. dated Dec. 15, 2021 (English + Original) 24 pages.
Colombian Office Action for CO Application No. NC2018/0010950 filed on May 15, 2017 on behalf of SOFAR S.P.A. dated Oct. 14, 2021 (Partial English + Original) 9 pages.
Corrected Notice of Allowability for U.S. Appl. No. 15/305,470, filed Oct. 20, 2016 on behalf of SOFAR S.P.A. dated Jan. 10, 2022 4 pages.
Final Office Action for U.S. Appl. No. 16/308,330, filed Dec. 7, 2018, on behalf of SOFAR S.P.A. dated Feb. 9, 2022. 22 Pages.

(56) References Cited

OTHER PUBLICATIONS

Mexican Office Action for MX Application No. MX/a/2016/022766 filed on Sep. 5, 2014 on behalf of SOFAR S.P.A. dated Oct. 26, 2021 (Partial English + Original) 12 pages.
Patel, R., et a., "New Approaches for Bacteriotherapy: Prebiotics, New-Generation Probiotics, and Synbiotics," Clinical Infectious Diseases, vol. 60, Issue supplement 2, May 15, 2015. pp. S108-S121. 15 Pages, https://doi.org/10.1093/cid/civ177.
Yuanning S. et al., "Analysis of Lactic Acid Bacteria Protein Dissolution and Aroma Production Ability" Chinese Brew, vol. 33 No. 3, Dec. 31, 2014 (English Abstract + Original) 4 pages.
Azad M.D.A.K et al., "Immunomodulatory Effects of Probiotics on Cytokine Profiles" Biomed Research International, vol. 2018, Oct. 2018, pp. 1-10.
Balzaretti S. et al., "The vaginal isolate Lactobacillus paracasei LPC-S01 (DSM 26760) is suitable for oral administration" Frontiers in Microbiology, Sep. 2015, 13 pages.
Bedford A. et al., "Implications of butyrate and its derivatives for gut health and animal production" *Animal Nutrition*, vol. 4, 2018, pp. 151-159.
Borycka-Kiciak K. et al., "Butyric acid—a well-known molecule revisited" *Gastroenterology Rev*, vol. 12 No. 2, 2017, pp. 83-89.
Cheng A. et al., "Polyphenols from blueberries modulate inflammation cytokines in LPS-induced RAW264.7 macrophages", *Acta. Paediatrica. Supplement, Elsevier*, vol. 69, Jun. 2014, pp. 382-387.
Connors J. et al., "The Role of Succinate in the Regulation of Intestinal Inflammation" *Nutrients*, vol. 11 No. 25, 2019, 12 pages.
Corrected Notice of Allowability for U.S. Appl. No. 15/305,470, filed Oct. 20, 2016, on behalf of SOFAR SPA. dated Feb. 25, 2022. 3 Pages.
Cremon C. et al., "Effect of Lactobacillus paracasei CNCM I-1572 on symptoms, gut microbiota, short chain fatty acids, and immune activation in patients with irritable bowel syndrome: A pilot randomized clinical trial" UEG Journal, Sep. 2017, 10 pages.
Cui J. et al., "NMR-based metabonomics and correlation analysis reveal potential biomarkers associated with chronic atrophic gastritis" *Journal of Pharmaceutical and Biomedical Analysis*, vol. 132, 2017, pp. 77-86.
Feng W. et al., "Sodium Butyrate Attenuates Diarrhea in Weaned Piglets and Promotes Tight Junction Protein Expression in Colon in a GPR109A-Dependent Manner" *Cellular Physiology and Biochemistry*, vol. 47, 2018, pp. 1617-1629.
Franco V. "Effectiveness of an association of a cranberry dry extract, D-mannose, and the two microorganisms Lactobacillus plantarum LP01 and Lactobacillus paracasei LPC09 in women affected by cystitis: a pilot study." *US National Library of Medicine*, Nov. 2014, 6 pages.
Gwiazdowska D. et al., "The impact of polyphenols on Bifidobacterium growth", Acta Biochimica Polonica, vol. 62 No. 4, Jan. 2015, 8 pages.
Hajjar R. et al., "The role of butyrate in surgical and oncological outcomes in colorectal cancer" *American Journal of Physiology*, vol. 320, Jan. 2021, pp. G601-G608.
Hakansson A. et al., "Blueberry husks, rye bran and multi-strain probiotics affect the severity of colitis induced by dextran sulphate sodium" *Scandinavian Journal of Gastroenterology*, vol. 44 No. 10, Jan. 2009, pp. 1213-1225.
Hurst N.R. et al., "The Short Chain Fatty Acids, butyrate and Propionate, have Differential Effects on the Motility of the Guinea Pig Colon" *Neurogastroenterol Motil.*, vol. 26 No. 11, Nov. 2014, pp. 1586-1596.
International Preliminary Report on Patentability for International Application No. PCT/IB2020/058774 filed on Sep. 21, 2020 on behalf of SOFAR S.P.A. dated Mar. 15, 2022 6 pages.
International Preliminary Report on Patentability for International Application No. PCT/IB2020/058769 filed on Sep. 21, 2020 on behalf of SOFAR S.P.A. dated Mar. 15, 2022 6 pages.
International Preliminary Report on Patentability for International Application No. PCT/IB2020/058777 filed on Sep. 21, 2020 on behalf of SOFAR S.P.A. dated Mar. 15, 2022 6 pages.
International Preliminary Report on Patentability for International Application No. PCT/IB2020/058778 filed on Sep. 21, 2020 on behalf of SOFAR S.P.A. dated Mar. 15, 2022 6 pages.
International Preliminary Report on Patentability for International Application No. PCT/IB2020/060412 filed on Nov. 5, 2020 on behalf of SOFAR S.P.A. dated May 10, 2022 7 pages.
International Search Report and Written Opinion for International Application No. PCT/IB2020/058778 filed on Sep. 21, 2020 on behalf of SOFAR S.P.A. dated Feb. 18, 2021 8 pages.
International Search Report and Written Opinion for International Application No. PCT/IB2020/058769 filed on Sep. 21, 2020 on behalf of SOFAR S.P.A. dated Feb. 18, 2021 8 pages.
International Search Report and Written Opinion for International Application No. PCT/IB2020/058774 filed on Sep. 21, 2020 on behalf of SOFAR S.P.A. dated Dec. 8, 2020 8 pages.
International Search Report and Written Opinion for International Application No. PCT/IB2020/058777 filed on Sep. 21, 2020 on behalf of SOFAR S.P.A. dated Apr. 20, 2021 26 pages.
International Search Report and Written Opinion for International Application No. PCT/IB2020/060412 filed on Nov. 5, 2020 on behalf of SOFAR S.P.A. dated Mar. 4. 2021 10 pages.
Koradia P. et al., "Probiotic and cranberry supplementation for preventing recurrent uncomplicated urinary tract infections in pre-menopausal women: a controlled pilot study" *Expert Review of Anti-Infective Therapy*, vol. 17 No. 9, Sep. 2019, pp. 733-740.
Krokowicz L. et al., "Sodium butyrate and short chain fatty acids in prevention of travellers, diarrhoea—a randomized prospective study" *Travel Medicine and Infectious Disease*, Aug. 2013, 17 pages.
Lacombe A. et al., "The potential of berries to serve as selective inhibitors of pathogens and promoters of beneficial microorganisms" *Food Quality and Safety*, vol. 1 No. 1, Mar. 2017, pp. 3-12.
Le Noci V. et al., "Modulation of Pulmonary Microbiota by Antibiotic or Probiotic Aerosol Therapy: A Strategy to Promote Immunosurveillance against Lung Metastases" *Cell Reports*, vol. 24 No. 13, Sep. 2018, pp. 3528-3538.
Mileo A.M. et al., "Polyphenols: Immunomodulatory and Therapeutic Implication in Colorectal Cancer" *Frontiers in Immunology*, vol. 10 Apr. 2019, 10 pages.
Milko R. et al., "Survival of L. casei DG (CNCMI1572) in the gastrointestinal tract of a healthy paediatric population", *European Journal of Nutrition, Steinkopff Verlag*, vol. 58 No. 8, Nov. 2018, 10 pages.
Nanau R.M. et al., "Nutritional and Probiotic Supplementation in Colitis Models" *Digestive Diseases and Sciences, Kluwer Academic Publishers-Plenum Publishers*, vol. 57 No. 11, Jun. 2012, pp. 2786-2810.
Non-Final Office Action for U.S. Appl. No. 17/090,669, filed Nov. 5, 2020, on behalf of SOFAR S.P.A. dated Feb. 17, 2022. 45 Pages.
Notice of Allowance for U.S. Appl. No. 15/305,470, filed Oct. 20, 2016 on behalf of SOFAR S.P.A. dated Feb. 15, 2022 6 pages.
Notice of Allowance for U.S. Appl. No. 16/301,361, filed Nov. 13, 2018, on behalf of SOFAR S.P.A. dated Mar. 30, 2022. 11 Pages.
Rajendran V.M. et al., "Na—H Exchanger Isoform-2 (NHE2) Mediates Butyrate-dependent Na+ Absorption in Dextran Sulfate Sodium (DSS)-induced Colitis" *Journal of Biological Chemistry*, vol. 290 No. 42, Oct. 2015, 10 pages.
Saez-Lara M.J. et al., "The Role of Probiotic Lactic Acid Bacteria and Bifidobacteria in the Prevention and Treatment of Inflammatory Bowel Disease and Other Related Diseases: A systematic review of randomized human clinical trials" *Biomed Research International*, vol. 2015, Jan. 2015, pp. 1-15.
Xu J. et al., "Intake of blueberry fermented by lactobacillus plantarum affects the guy microbiota of L-name treated rats" *Evidence-Based Complementary and Alternative Medicine*, vol. 2013, Jan. 2013, pp. 1-9.
Xue H. Lactose-Induced Chronic Diarrhea Results from Abnormal Luminal Microbial Fermentation and Disorder of Ion Transport in the Colon *Frontiers in Physiology*, vol. 11, Jul. 2020, pp. 1-14.
Yehua Y. "Mixed fermentation of blueberry pomace with L. rhamnosus GG and ingredient, antioxidant activity and health-promoting benefits", *Food and Chemical Toxicology*, vol. 131, 2019, 8 pages.
Yoshida Y. et al., "Oral administration of Lactobacillus plantarum Lq80 and Megasphaera elsdenii INP-001 induces efficient recovery

(56) References Cited

OTHER PUBLICATIONS from mucosal atrophy in the small and the large intestines of weaning piglets" *Animal Science Journal,* vol. 80, 2009, pp. 709-715.
Brunkwall L. et al., "Self-reported bowel symptoms are associated with differences in overall gut microbiota composition and enrichment of Blautia in a population-based cohort" *Journal of Gastroenterology and Hepatology,* vol. 36, (2021), pp. 174-180.
Cicenia, A. et al., "Postbiotic Activities of Lactobacilli-derived Factors", J Clin Gastroenterol, vol. 48, Supp. 1, Nov./Dec. 2014, S18-S22 (5 pages).
De Almada C. N. et al., "Paraprobiotics: Evidences on their ability to modify biological responses, inactivation methods and perspectives on their application in foods" *Trends in Food Science & Technology,* vol. 58, 2016, pp. 96-114.
Lee Y. K. et al., "Handbook of Probiotics and Prebiotics" Wiley, 2009, Excerpt: 3 pages.
Metagenomics—Wikipedia, the free encyclopedia, Dated: May 16, 2013 https://web.archive.org/web/20130516095714/https://en.wikipedia.org/wiki/Metagenomics, 16 pages.
Non-Final Office Action for U.S. Appl. No. 14/916,961, filed Mar. 4, 2016 on behalf of SOFAR S.P.A. dated Aug. 29, 2022. 25 Pages.
Notice of Allowance for U.S. Appl. No. 15/305,470, filed Oct. 20, 2016, on behalf of SOFAR S.P.A. dated Jun. 9, 2022. 11 Pages.
Notice of Allowance for U.S. Appl. No. 16/467,797, filed Jun. 7, 2019 on behalf of SOFAR S.P.A. dated Jul. 15, 2022 13 pages.
Patel R. M. et al., "Therapeutic Use of Prebiotics, Probiotics, and Postbiotics to Prevent Necrotizing Enterocolitis: What is the Current Evidence?" *Clin Perinatol,* vol. 40, Mar. 2013, pp. 1-20.
Poortmans J. R. et al., "Protein metabolism and physical training: any need for amino acid supplementation?" *Nutrire,* vol. 41 No. 21, 2016, pp. 1-17.
Qin J. et al., "A human gut microbial gene catalogue established by metagenomic sequencing" *Nature,* vol. 46, Mar. 2010, pp. 59-67.
Santigosa E. et al., "Modifications of intestinal nutrient absorption in response to dietary fish meal replacement by plant protein sources in sea bream (*Sparus aurata*) and rainbow trout (*Onchorynchus mykiss*)" *Fish Nutrition Research Laboratory,* 2011, 38 pages.
Tomar S. K. et al., "Role of probiotics, prebiotics, synbiotics, and postbiotics in inhibition of pathogens" *The Battle Against Microbial Pathogens: Basic Science, Technological Advances and Educational Programs,* 2015, pp. 717-732.
Tsilingiri K. et al., "Postbiotics: what else?" *Beneficial Microbes,* vol. 4 No. 1, Mar. 2013, pp. 101-107 (Abstract Only).
Tsilingiri, K. et al., "Probiotic and postbiotic activity in health and disease: activity comparison on a novel polarised ex-vivo organ culture method", Gut 2012; 61:1007-1015 (9 pages).
WHO Technical Report Series 935—Protein And Amino Acid Requirements in Human Nutrition, 2007, 284 pages.
Zhernakova A. et al., "Population-based metagenomics analysis reveals markers for gut microbiome composition and diversity" Science, vol. 352, Apr. 2016, 15 pages.
Final Office Action for U.S. Appl. No. 17/090,669, filed Nov. 5, 2020 on behalf of SOFAR S.P.A., dated Nov. 9, 2022. (15 pages).
Non-Final OA Office Action for U.S. Appl. No. 16/308,330, filed Dec. 7, 2018, on behalf of SOFAR S.P.A. dated Sep. 1, 2022. 26 Pages.
Non-Final Office Action for U.S. Appl. No. 14/916,959, filed Mar. 4, 2016, on behalf of SOFAR S.P.A. dated Sep. 30, 2022. 34 Pages.
Non-Final Office Action for U.S. Appl. No. 16/467,797, filed Jun. 7, 2019, on behalf of SOFAR S.P.A. dated Sep. 14, 2022. 5 Pages.

* cited by examiner

EXOPOLYSACCHARIDES AND USES THEREOF

CROSS-REFERENCE TO RELATED APPLICATIONS

This application is a 371 national-stage application of International PCT Application No. PCT/IB2017/057576, filed Dec. 1, 2017, which claims priority to Italian Patent Application No. 102016000122724, filed Dec. 2, 2016, all of which are incorporated herein by reference in their entirety.

The present invention refers to exopolysaccharide molecules and their use to boost immune system.

BACKGROUND

The consumption of food products and supplements named probiotics, i.e. containing live microbial cells, to potentially prevent or treat specific diseases, is constantly gaining popularity.

A number of *Lactobacillus* species, but also some other have been proposed as, and are used as, probiotic strains—live microorganisms as food supplement in order to benefit health.

Strains of *Lactobacillus paracasei* are Gram-positive, non-spore-forming bacteria that are common inhabitants of the human intestinal tract. Specific strains of *L. paracasei* are found naturally in a number of fermented food products, and they have traditionally been used in the production of fermented milks and cheeses.

More recently, specific strains of *L. paracasei* have been used in probiotic dietary supplements, including the strain *L. paracasei* DG (commercially known as *L. casei* DG®, Enterolactis®). A range of health-promoting properties has been assigned to *L. paracasei* DG including the improvement of ulcerative colitis and treatment of small intestinal bacterial overgrowth and a number of mechanisms have been proposed for the probiotic effect.

One of the most studied mechanisms relates to the ability of probiotic bacteria to antagonize pathogenic organisms by either excretion of antimicrobial agents or the displacement of pathogenic organisms through the competitive occupancy of adhesion sites. In addition, there are a number of reports referring to the health benefits result from stimulation of the immune system by components presented at the surface of probiotic strains.

Several studies have demonstrated that the polysaccharides present at the surface of the bacteria, referred to as either capsule or as exopolysaccharides (EPSs), can play a role in both the displacement of pathogenic organisms and the stimulation of the immune system.

In this context, the present invention refers to exopolysaccharide molecules and their use as prebiotics and/or probiotics, in particular to boost immune system.

BRIEF DESCRIPTION OF THE DRAWINGS

FIG. 2 shows selected regions of the 1H-NMR of the DG-EPS recorded at 70° C. in D20 and using acetone as an internal standard, anomeric (H-1) resonances are labelled A-F in order of decreasing chemical shift.

FIG. 3 shows selected regions of overlaid COSY (black contours) and TOCSY (grey contours) spectra for the DG-EPS recorded at 70° C.; symbols A-F identify individual sugars and numbers (1-6) identify the C/H ring position.

FIG. 4 shows selected regions of the HSQC spectrum of DG-EPS; the location of the individual ring and H6-protons and carbons are identified on the top frame, and the location of the anomeric protons and carbons are identified on the bottom frame. The spectrum was recorded in D20 at 70° C.

FIG. 5 shows the anomeric region of a ROESY spectrum recorded for the DG-EPS; inter- and intra-residue NOEs from the anomeric hydrogens to ring protons are individually labelled.

DEFINITION

Figure 1:
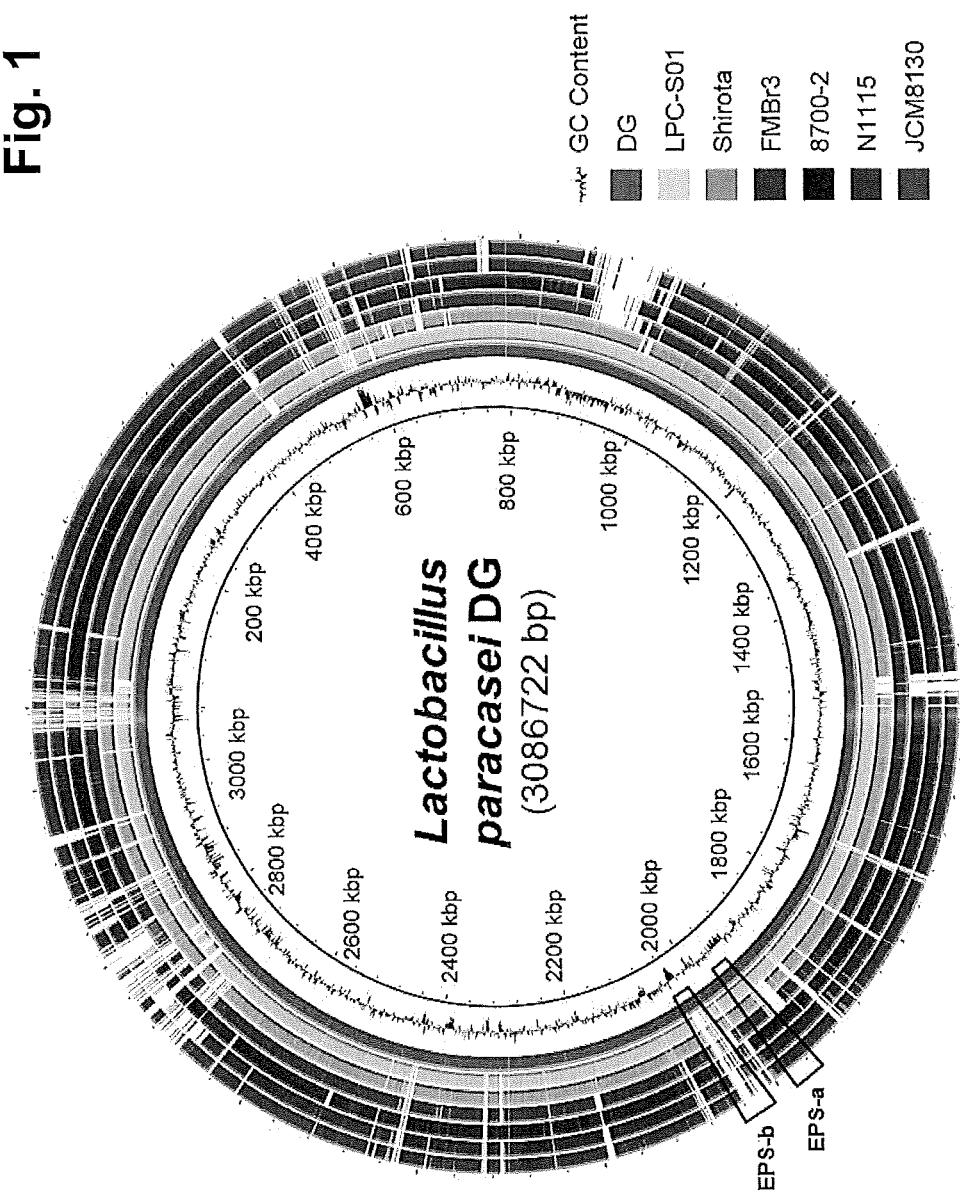
FIG. 1 shows a comparative genomic analysis of *Lactobacillus paracasei* DG with other complete genome sequences of *L. paracasei* strains. (A) Circular genome atlas of *L. paracasei* (reference genome) and six other publicly available *L. paracasei* genomes; highlighted in the atlas are the two putative exopolysaccharide (EPS) regions of strain DG.

In the context of the present invention, "exopolysaccharide" means extracellular polymeric substances (EPSs) mainly composed of carbohydrates, i.e. natural polymers of high molecular weight secreted by microorganisms into their environment.

In the context of the present invention, "prebiotic" means substances that induce the growth or activity of microorganisms (e.g., bacteria and fungi) that contribute to the well-being of their host.

In the context of the present invention, "boost immune system" means mainly activate immune system cells toward any potentially detrimental elements.

DETAILED DESCRIPTION

In a first aspect, the present invention refers to an exopolysaccharide comprising at least one repeating unit of rhamnose, galactose and N-acetygalactosamine in a ratio of respectively 4:1:1. The exopolysaccharide can be also defined a heteropolysaccharide.

According to a preferred embodiment of the invention, the rhamnitol is 1,2,3,4,5-penta-O-acetyl-L-rhamnitol.

According to a further preferred embodiment of the invention, the galactose is 1,2,3,4,5,6-hexa-O-acetyl-D-galactitol.

According to a further preferred embodiment of the invention, the N-acetygalactosamine is 2-acetamido-1,3,4,5,6-penta-O-acetyl-2-deoxy-D-galactitol.

According to a further preferred embodiment of the invention, the rhamnitol is 1,2,3,4,5-penta-O-acetyl-L-rhamnitol, the galactose is 1,2,3,4,5,6-hexa-O-acetyl-D-galactitol, and the N-acetygalactosamine is 2-acetamido-1,3,4,5,6-penta-O-acetyl-2-deoxy-D-galactitol.

According to a preferred embodiment, the rhamnose residues have L-configuration and/or the galactose and/or the N-acetylgalactosamine has (have) D-configuration.

According to a preferred embodiment of the invention the exopolysaccharide comprises the repeating unit having Formula I:

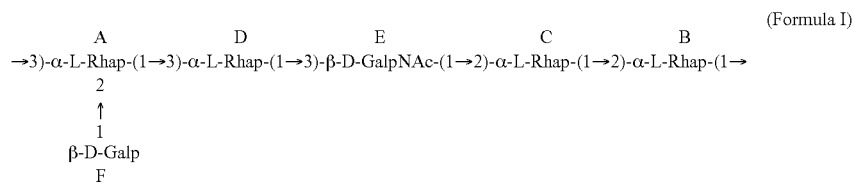

(Formula I)

Preferably A as a 2,3-linked rhamnose, preferably B as 2-linked rhamnose, preferably C as a 2-linked rhamnose, preferably D as a 3-linked rhamnose; preferably E (N-acetylgalactosamine) is 1,3-linked; and preferably F are terminal galactose monomer.

According to a preferred embodiment A is preferably linked to the 3-position of D, C is preferably linked to the 2-position of B, D is preferably linked to the 3-position of E; F is preferably linked to the 2-position of A.

According to a further embodiment of the invention, the exopolysaccharide is produced or can be obtained from *L. paracasei* DG strain or mutant strain thereof.

In other words, when these bacteria are grown in an appropriate medium/broth at the appropriate temperature and for predetermined time, the exopolysaccharide molecules are secreted into the medium/broth. This broth/medium is defined conditioned medium meaning that it contains the metabolites derived from bacteria. The exopolysaccharide is one of the metabolites.

In some embodiments, the exopolysaccharide remains anchored or is part of the cell membrane and/or cell wall.

Therefore, in some embodiments it is possible to isolate the membrane/wall from the bacteria wherein said membrane/wall comprises the exopolysaccharide of the invention.

Therefore, as alternative or in combination of using the conditioned medium it is possible to use the membrane/wall fraction of the bacteria comprising the exopolysaccharide or fragments thereof.

The *Lactobacillus paracasei* strain DG has been deposited on May 5, 1995 at the National Collection of Microorganisms Cultures of the Pasteur Institute at the address of 25-28 rue du Docteur Roux, 75724 Paris Cedex 15 under the code CNCM I-1572.

A further aspect of the present invention refers to the cluster of genes codifying the proteins involved in the synthesis/expression of the exopolysaccharide of the invention.

This cluster comprises SEQ ID NO: 1 or fragments thereof or any sequence having 80-99% of identity.

| Sequence | SEQ ID NO | Name |
|---|---|---|
| ccatctttag attattaaat aatattatcc tagattgcaa taataaagtt<br>accacctagaaagaggcttg ctcactgctt gaactgggggt ttgccaacgg agacattttc<br>taggtttgttattgataaac gctgtggctc gttgaatatt ggcctctgaa acctgatcaa<br>actgtgttccccttcgggaaa tagtagcgaa gttctcgatt gaaccgttcg ttcgtgcccc<br>gttcattcgggtgataggca ctggcaaaagt aaatcggtat ccgatagcgc tttgtaagcg<br>cctgatcgcaggaaaactct ttaccgtgat caaccgtcac tgatcgaacc ggacccggaa<br>agtctaccatcagtcttgca aatcctttga gaacagcatt ttgtgataag ttttcaagct<br>tagttgtcgccattaaacgt gtcacccgat cgacaatggt caaaacagca gcctttgacc<br>cgcgaccaccgcgaactgta tccatctcta aatgtccttt ttcggttcgc cgattagctg<br>actcactgcgaatctcaatt gaggtgccta ctgcttggtt atagcgcgac cgaaggtctt<br>gtcttcttttatgacgttta ccgtgatcaa agagttggct tggctgaaaa tcgacttgtc<br>tttgataaatccagtggtaa atcgtgtgtg gcgcacagtg aacgacataa ccgaccattt<br>caggggaccaacctaggttt agcttctcag ttaccatccg cttcaactta ggcgttaaaa<br>tcgagtgccgaccacaacga tgccgacaag tatccggcatg atcctgagct ataatggcgc<br>agtaatccccttcagggcaa cggtgaagct catgcctaat agaaatacga gagcggccta<br>aggtcgcggcgatgtattga atcgtgtggt gttgcatcag ttctatctga gatcgttcaa<br>ttaaggttataatggccatg ggacctgtcc ttctctctag atggtatgtt atgcaaacac<br>catttttagcaagaacggaca ggtctttttt cacattttct gggtggtaac tttaattatg<br>caatctaggttataaaatct tttgatagcc cggcgtttca tctaatgtta aagcataacg<br>ccgcacattaaaggtgggggg aaaccatgtt agacaatatc gggaaatttgg tgcaccaaca<br>gcgccgcagtttgaacttga cgattgagaa gttgcggag cgatccggcg tctcgatcag<br>tctgattcgcgaatggagc gtggagacgt caacaatatc agcataaaaa aattgaccga<br>cattgcgcgggctttaaata tgcaggtagg cgacttcttt attgctccgg aaatgagcga<br>tattagcacattagcggtgg tgaaatactt aacccactta ccagagaaag aacgggcgcg<br>tgtttccgaggtactcatgc aggtgattaa cctgtaagta ccacctttttt agaacagtct<br>gtcacttgaggctgttcttt tttgatatca aaaatgtcag aatgaccttta aaaggatggc<br>gcaaaccgttgtcagtcagc tggtaaaacg cgtatactaa atgcactgat tttagacaat<br>gaacgcgaacttgcacggtt agcttggttt gacaaagtgg cactgaatag ttgatcaagt<br>atttgttcggctaacaggct ttcttcacaa taaccaaccg ccatgtggag aacgcattt<br>aaaagaaggagaatgatcga catgacattt gaagcaattt taccgtcctt taaagccggc<br>aagaaggccgttcgcaccgc tgggaaggt actgagttgt atgtgcaact agttccggaa<br>ggcaaattcgaaggcgacac tttgaatccg tattttttga tcaaaactgc cgacgaagct<br>ttcagtctctggtcaccgac tgactgtgac attttggctg aagactggca gcttgtgaac<br>gcatgacgcatttcgacttc accgacaaga ccgtcatcat caccggcgcg gcttctggca<br>tcggtgcggctcaggcggcg gcttttcagg cagctggtgc cactgtggta ggaattgacc<br>tccaaccaattagcaaactc acagacgcca ttcaggccga tgtgagcgat cctgccacgg<br>cagcagcgattgcggctcaa taccagccag atattgtctg caatacggcg ggcgtgttgg<br>atggttatcaaactgtgacc gatacggcgc tctcggcatg cagcacatt ctcgatgtcg<br>atcctaccagtcagttctta atgatcaagg cgctgctgcc ggggatgctg ctcgcggtc<br>acggtattttcatcaatatg agttccatcg ctggtttagt cggtggtggt ggcggcttgg<br>cgtatactgctgctaagcac gccgtcatcg tcctccacaa gcaattagac cttgattacg<br>ccgccaagggcattcgcgcc aacgcgctcg caccaggcgc tatcaacacg<br>cccatgaacg ccgctgattttgccggcgac gggaaaatgg ctgcgtgggt agcgcgcgaa<br>accccagcca aacgctgggc caagcccgag gaagtcgcac aattatcctt gttctctggcc<br>agcgatgctg ctgattatattcatgaacc gtgattccca ttgacggcgg ctggctcgaa<br>aagtaaactt aatgcattgcaacaccaaaa ctgaaaacgg aaggcaatcc ttccacgacg<br>atacttactt tccctttgatcgtcgttacta ctggcatagc cacaaaggag aacaaacatg<br>caaacaactt caaccaccccatcgttcaatc gtcagtctcg ccaaaaccgc catgatcacg<br>tccatttacg tcgtgatgaccctcatgctc agtccactca gcttcggggt cgtacaagtt<br>cggttctccg agatgctcaactacacggca ctcttcaacc gccgttatgt ctgggcgtc<br>acgctgggtg tttttttggccaatttaacc tcgtcaaccg cactcctcga tgtcccaatc<br>ggcaccctcg gcacgctcgtcttcatcatc atcagccgct ggttagccaa actcgtccaa<br>ccaaaatggg ctaaattcaccatcatgggt atccttttcg cctttatccat gttcaccatt<br>gccggcgaac tgaccatcctcacaaaagtc ccattctgcc caacctacgc taccatcgcg<br>cttggcgaag ccatctcgatggccgtcgt ggcgttgtga tgatgatttt gacgcgattt<br>gtggatttgg ataagtaggcgataaggcta ttgaaagagg ctccctataga aaaagctta<br>ctggcaggaa aggtttcgctgaagcttttc gatctggcag aagggcaagc aggtctgatt<br>gctgtgttca aaagttgtcgcaggggttag gcttccgatg cacctgattt tggttaaata<br>ttggttaaat acaaaaaagcatcaagacaa ttgtctcgat gcttttttta atggaaggga<br>tacgccctaa atctttttttaagcaagatgc taatcctagg taatgatggc cttttcattg<br>ttactttttc aatgtctgcatgacatcctt agcaatcaac gtgtagtaat gcggccggcc<br>agcgtcgttc ggatggacaccgtcatcagc aaaccagtcg tcattgccac ctgccagata<br>ataccaatcc accacatgcagattggcatg ggttttagct gccgcatgaa tcagcttgtt<br>aaccggatca atccacgctttcccggagc atacgcgtc acccagaaga cctgacgctc<br>agtcccaagc tgatccagaatcccgttaat gtcggcctct gtcataggtc cgttcgtccc<br>caaactgatc acaaccgttagccaactt acactcgtac ttcagctgac taataatcgc<br>aggtgctgcc tgcacctgccgaccaacctc agcatcaatc gacatctccg gaaaaagcac<br>cttcaaaatat gccgaactccccagcataat cgaatcgcca atcgccgaca ccggcaatgt<br>tttggccgca ttaatctgctgtcagttaa gccataaagc cgatactgat tcagaaccctt<br>ttccttcttc accttcgccttagaatcctt ctgaatgcgc tgccgcgtcg attggttaac<br>cgcaatcgcc tgctcagactgataatgctt gacgtagaag aaccccgcga caccagcagt<br>tgccaatccc aacgcgatacttaatagcca gtccgtaga cgtagcttgt ttttttttcat<br>gatttagtga accccccaaaatttgcattgc ttatatttta aactaaaaat caggttagtc<br>tgattacaag ttagggtcattctgacgggt ttataagaa ctgtaaatag actgtaataa<br>aatgaaattt gaagttaccaaccttagtaa aaggcgtgta tatcggattc aaactaatct<br>gatagtacaa ccaaaaaacatgacattcatt caaaacaggt agacttcgtc acacatgcta<br>ggttattatg gtttggagtagagttttaaa agtctttttt agaaatgcgg gctgcgctgc<br>ttgtggtccg catttttgagtgttggatata aattatggga ttaggtgggg aaagagttaa<br>tgaacaagca aatcgaccttttcgcagttgt ggaatgtatt taaacgcagc tttgttgcaa | SEQ ID NO: 1 | *Lactobacillus paracasei* strain DG Exopolysaccharide-b EPS-b region |

-continued

| Sequence | SEQ ID NO Name |
|---|---|
| tgattattct cggaattctt gggatggcgg ctgcttattt cggtgctaaa acgtttattt | |
| cgccaaaata tgagtctgat acgtcattgc tggtcaatcg caagcaggat aacgatccaa | |
| acatgcaatt gaatgctcag caggctgata ttcagatcat taatacatac aaggacatta | |
| tcacacgtcc agtcgtttta caggctgttg cgagtgaact aacaagtccc cagcgtgtat | |
| tgataaaaaa agctacaaag gcggtttatg gtacgcgtta caatgcaaca acaggtgttc | |
| gagaagaata tgttactcaa aaagctcaac ggcgcaata taagttaaag | |
| ccagctcaat actccaatct ttcatctacc gatcttgcta aggtcgtaac agtatccaca | |
| cagcaaaatt ctcaagtgtt taccgttaac gttaaagata cagatcctgt tcgggcaaga | |
| gatattgcaa atgaagttgc taaggttttt gaaaagaaaa ttgctaaaat catgagcatt | |
| tccaatgttt ccgttgtttc aagggcaacg gctgatccga taccagtatt gcctcggttg | |
| aatctaatgg cattaattgg cctagtttta ggagtgcttg tcgctttcgt ttggggattg | |
| attcgagaac tgacagatca gaccattaag gatattgact ttatcacgga cgaccttgga | |
| ttggttaatt tgggaatagt caattatgtt caacatatgc gtgacatgag tgaagcgatc | |
| gatgccacaa agtcaataga agctgaggat actgaagatt acgatgcgtc ggactttccg | |
| caacgtagcc gtcgccgaat ctaaggagga agaaaacatg aagtggtctt | |
| tcaaacaact tttccaccgg caacaagaag atcaagaaac tcaaaagaac | |
| ggggtcattt tagtcacttt cgctgaacca aaacatgttg tttcagaaca gtttcgcaca | |
| gtgcgaacta atattgagtt tgctggagca gctcttgata agtgtcaagt tgttatgttt | |
| acgtcttcag tgatgtccaa gggcaagtcg actgtttcgg caaacgttgc ggtaacttgg | |
| gctcaggcgg ggaaaaaggt tttactgatt gattgtgacc ttcgacgacg gactgtacat | |
| gcaactttc gaacgcttaa tctagaggga gtcacaacag tattaacggg gaaaagttct | |
| gctcacaata tagttgagca aacatttgtg agtaatttag atattcttac ctccgggccg | |
| ctacctccca ctccgtctga acttttaaat tcacaacgta tggctaacct cgtggattgg | |
| gcacgcgaca attatgatat tgttgttcta gatgcaccgc cagtttttggc agtatctgat | |
| gtacaggtct tagtcccaa aacagatggc gtagtggttg tcgcaaagat ggggaagact | |
| ttaaagggag acttaagacg aactattgaa gttctgaagc ttgcaaaagc taaacttctt | |
| ggatgtgtag agcgtgtgaa tgttaaacgt ggcgatcgcg gctatggcta cggttatggc | |
| tacggttatg ggaatgaagg gactaaataa tccgatatta tcaacctaaa | |
| gaaaaaggc atagctcaaa tatttataaa ttgatgctta acgcattgtt gtctgttttt | |
| gatgtttggg tggttatctg attatttatg tgatttaata gtggcaagaa aagtttataa | |
| atttaatata cttgcacaaa gattttttaag aatgcaagtt tttattcttg caaagttgaa | |
| aaagtgattt cgactttagc acggggaacg cgacatacta aagtcacttc acgtagtacg | |
| tttgggggag gaaggatcat gtatcaacac ttcattaaaa gaattttaga tattttggga | |
| gcaataatag cattgctaat cttggcaatc ccgttttatca ttattgcaat acttattagg | |
| atggattcaa cgggtccagc cttttttcgt cagcaaagaa tggggaagga tgggaagccc | |
| tttagaattt acaagtttcg tacaatggac caagaggccc cacacgatct tgcaactgct | |
| aaactagata atgctaataa gcagattaca cgggtcggtc gattgctccg aaagacaagt | |
| attgatgagt tacctcagtt cattaatgtg ttaaagggcg acatgagcat ggtcggacca | |
| cgtccggttg tcttgacaga aactgagcta attgaaatgc gtcacaaaaa tggcgctgaa | |
| agtgctttac cggggataac aggattagcg caggtaaacg gaagagatcg gttatccaat | |
| ttaagtaaat ctaattacga tggtatttat gtttcttcaa tttcattttt tatagattca | |
| aagataatgg tcaaaactttt ctggtatgta gctcttcgat taggtattag agaaggtcgt | |
| ccaaattcta aaaagttaa tgctgctaat atcggagaaa aaatattag gccgaacgaa | |
| cagcaactat ttttaaaaag gaaagcttag atttaatgaa tgataatact aaagaaatta | |
| gcttttgtac cgttacttat aacagcgcaa aagaagtgac ccagttaata gaaaatatag | |
| agtctctaaa aagcgatttg ttttcctcac gagttttcat tgttgataat gggtcccaag | |
| atgcacagt gaatatagtt ttaaagcttt ctcaggaaca ctctaatctt gttttaatta | |
| ggcctgatgt gaataggga tttggagcag gcaacaatca ggtgttaaat atgattacct | |
| cggattacca tattctgatt aatccagatg tgcgtatacc gtcctccaga acgattgaaa | |
| agatgatcgg gtatatggat actcattctg atgttggact gttatccccc aaaattctta | |
| atgttgacgg ctcagttcaa aaattattta gacataatcc tactgtactt gatatggcgt | |
| tacgttcat ctcacctaat cttatgaaaa aaaggcaaga ttggttcgtc catgaagaga | |
| ccgggtatac tcagagcgga gtgatcgatc aagctagtg agcattttatg tttttccgtt | |
| catctgtatt taaaggtata gcgggttttg atgagagata ctttatgtat ttggaggatg | |
| cagacattac tcgtaaggtc aatgctgtta gcaaagcaat ttttttatcct gaagtaagca | |
| tcatgcataa gtgaatcga caaaatcatt caaagttgaa attcattggc tatacaatta | |
| agagcatggt tcaatatttt aacaaatggg gatgaagtt attctaacca tctggggagat | |
| tgattgaatg atttggctgg gaattgtctg tattagcttt atatctagtt gtttccaaaa | |
| attagagaag tcagcgggtt tgatatcttt tttgggttta ggtattatgg cgggcacacc | |
| aaatatgttg tacgatcccg atgcttttgt ctatttacaa aattataatt cgggcactga | |
| ttatttcgag acaggatata attgggtgac aaagctattt gagcctagtg tagattatca | |
| aacatttaga ttatacagta gttttatttat tttttcctg atgttttag cagtactttt | |
| gatgacaaag cacgtatcaa gtattgcgtt ggtttatgca atcgcaatgt ttccggttga | |
| taaagcacag actagaaatg tcatggcagc cgtcttttgt tcctttttgg agttcstgtt | |
| gttttgctgt aagcttggga aaagaggaat tcttccctca ttactggtca ttttttattag | |
| gatctttttt tcatagtctt gcactctact ttcttttact accattattta tggttgttta aaggctttat | |
| tgaaaagcat ttttctgcaa ttactacatg tctaattgtt gttgcgttta tttttgaaat | |
| cttaggttca acaagcatag cgccactatt agtacaactt ttgggaaagt ttgcaaatcg | |
| tgcgaacgtt gcagaaaatg tgtcaacttt atatgctgga ggtcagccat ttagtcagtg | |
| gtttgtttct ttcgcagtta ctatgatgat aattttaaca gttcaatttc ttagaaggca | |
| atacccaaac aatatgagat cctattacca aatgattta tgttcttcga tattatggtc | |
| agcacgtta atattgatga ctcttttcaat tgactacata agaattctga gaattgttaa | |
| gtacttctat tttatctata tcgtgaatgt tacttcaaat cagaagagca cggatcgcct | |
| tataggggtg acaatcagta ttggatcgc agtcgttttg atgtttgtcg ggttatgggt | |
| ctacggattt agtggtgacc aaaattcgagc aattttgggg tttatttaag gggactgaag | |
| aatgttgaaa gttggagtaa ttgttgttac ttacaatccg gatttaatga ttctacagaa | |
| taatctgacg acactaaaaa ggcaaaatgg catcaactgt ctgattgttg ataacggctc | |

| Sequence | SEQ ID NO | Name |
|---|---|---|

```
taagaattca aacgatttaa aaaaagtaag tgaaaactta aaagtcaaca ttatttcact
tgatagtaat cgtgggattg cttatgcaca aaatcgaggt tttgaatttt ttcaaagaga
agggttaaag tgggcgctta cttttagacca agacagcata gttcctgata acttactaga
agtgtatgta aagcaaaaag aattgaactc ttccgacaca gcaattttaa cttgtagcta
cgttgatgag gactggactg gaaagcaaaa agaagctatg cttcagcgtg
aaaagattgt gcaaaagcaa tatgtcattt cttcaggtaa tcttgtaaga atttcctctt
ggcaaaaagt gggtggattt gacgaattcc tctttattga catggttgac ttcgacttty
acgctaaact attttagct ggctttaaaa tctggcagac gaatgaagtc gtactaaaac
attctgttgg acaatccttaa aagaagccca tcgtgaaaaa aatacttctg attccagaaa
ctgctatttt ggccgatcat tcaccaattc gtcagtatta catttataga aatagtatta
ttttcgagaa aagatacacg atgattaccc aacgaaagtt tgttgttctc catactttcg
ttgcaacaag gagaatgttt gcgtatagca ataagttacg caagatgttt gcagcttggc
gcggagttat tgatggtgcc agatacaatg tagacaagga caaacaattt aaaaaaacac
tggcaaaact gaaacgatag ttatttgggg tgaataatg agaagtgaaa acgtaagtgt
cgcaatttgt ttagccacgt ataacgggga gaagtattta gaaaaacaga ttgactcaat
agtttcccaa tctgtctcta gttggacatt gtttattaga gatgatggtt ccaccgatgg
aacgcaaaaa atcattaaaa agtttgcaaa gaagtatccg caaaaagttt tcaacttatc
aggtcttcat ggaggcggaa attctaaaga aaatttttttt actattctgc aatgggtgag
cgaacacaaa acttttgatt attttatgtt ttctgatcaa gatgacattt ggttacctga
taaaattgca ttaagtgtca aggctattga ttctgatgat tctccatgtt tagttcatac
tgatctaaaa gttgtcgata aaacttggaa tacaataaca gaatctttca ttcggtacag
taacttaaat tctcaagtaa aggattttttc gcatatcctt gtacagaaca atgtaactgg
ctgcacaatg ttgtggaata agagtttaaa cgatttaatc gattttcatc cagattctag
aatccttatg catgattggt ggattgcttt aattgcatca gcgttttggaa atgtcgtctt
tgtaaaaact ccaaccatcc tctatcgaca acatgatgaa aatgtagtgg gggcagaagc
ggctggttct gtggcatata ttatttcaaa attgcgtaat tataagttga ttaaaaaagg
attgcaacgt acctttgggc aagcaaatat ttttaaagag atttattatc atcggttaga
tgccagttct aaaagtatac tagatgagta tttgcagctt cctgccaagt ccaaacttag
aaaaatatat cttctctcca agtatggatt tacaaaacaa agcaccatac aaattattgg
gcagtttctt tttgtctagt ctgttgaggc tgattaattg cgagtttaa aaaattattt
atatagtgtt gggtatcaag ttctaaacat gatattgcca ctcataacag gaccgtatgt
tgcacgagtt cttggaccga agggtgttgg gattaatact tatacaggtg cagtaacaca
atactttgtt ttattcgctg gcctagggat agcgctttat ggaaatcgac agattgctta
tgttaagggt gacccacatc agttaagcat taccttttgg gaaatacagt ttattaaaac
gattacaaca gtttgcgcct ttgtcgcttt ttcaatatat ttaattttcg tcaaagaata
taagttttat ttactgttac aatccgcgta tattttagct acaggatttg atatttcatg
gcttatgag ggcgttgagg attttaaaaa gaccttact agaaacacgt tagttcgaat
agtctcccct gttctaatcc tcacgctggt acacaaacaa agtgacgttt gggtatacat
agtcattctc gcagcttcta acctcggtgg gtatgttgcg ttgtgccaa ctctaaggcg
gctgctcgta cccattaaac tgtctgaatt acatcctagg aaacatttga agggcacact
gatttttattt gtgccataca tgacgctgaa catttatcct atcattaata aaacattact
caaacatttt cttgggggttg atgcttccgg ttatttttgaa aaaagtgatg tgatgatacg
tatggcgttg acagtagtga cgtcggtaag cgcagtatta ctgccacata catccaaggc
ttttgctgat ggcaaggttt cgttaattaa gaaattgcta aaaacctctt ttggatatgt
gtccatgatg gcattcccaa tcgcattagg aatggcggca atagcaccaa aatttggtgt
ttttcttttat ggtgaagggt ttgcaccggt tgggccagca atgatgatag aatctagtgc
cattattttc atgggggtggt cgagcatcac aggtaatcag tatttaattc cgacgatgca
gtcaaagcat tacacgcact cagttcttct aggctcggtt ttgaatattg ttcttgacgt
tcctcttatc attattttttg ggcttaatgg tgcagctttt gctactttga ttgctgaagc
gtttattgct atatatcagt taataatgat cagtggtcag gttgattatt ccacttggct
gatggacatc attaaatatt gtgtagctgc tataatcatg ttctgctttg ttttttttcgc
aagtagcatg ttgacgatga ccatcttgac cttagtgctt gaaatcatgc ttggtgccat
catttactta gtatgtctgt ttcttatgaa acccgcaact aataagcaac tcaaacggcg
agcattctca attattaacc gagttcggtc atgattattt ttggggggaat aatgacaata
agacgaaagg tttcttggtt gattcgttca cctgcacgat tacatgttgt gtatcggatt
gacgatttta caaataattt gaaggttcga agactgttac atatactatt gatcccagtc
ggcatgttaa acttaattag gctaaaactg atgactagat caccctgaaaa gtttatgtat
caattatcaa ttgttactac agtcaaaaat gaggctccat acttaagaga gtggctgaga
tatcacattt cggttggagt acagcacttt tatctttatg ataatgatag tcaagataac
ttagatgaag tgttaaaaga ttttttccgac tacgttactt taacaaagat acacggacga
gttagacaat ttgatgcata caatgacgcg ataaatcgat tcaggtatga aacaaagtat
atggcggtga tagacgcgga tgagtttatt tttagacgga gtaaagacaa gctgttacta
cctcttattg attatttact ttcaaataag tcatttggag gattggcggt gaattgggca
atatttggtt cttcggttt aaaaaagaaa cctttaggat tggttaccga caactttgta
tatcgggcca acgataactt taggaaaaac aggctggtta aaactatctg caatccgaga
aaagtctttt acttttcagt tagccatgct gcaaattact tgccaggtat ttatgcagtt
aatgagaatc aggaaaagt tgattggaca acaacgcaag ttcccagtat cagtaagatt
agaattaatc actattattc aaaatcacaa gaagagtttt tacgaaagcg agctcgaggc
gctggggatg ttgttggcct tagagactta ggagaattcg cagaacatga tcgaaatgat
gttttttacg actcgcttag agtttataat gaatcaagag gtttaaacaa agactgaggg
ggatattgaa agatgaaggg gattatatta gctgggggat ccggaactcg actctatcca
attacgaagg caacaagtaa acagttagtt acaaagccat gatttattac
ccattctctg cgctaatgtt gtctgggatc aaagagtttc tgattatttc tacgccagaa
tttctgccac agtttgaaga attatttggt gatggacata ctctgggact aaatattcat
tacaaggttc aaacagagcc aaatggattg gctgaggcat ttatccttgg tgcggattttt
atcggtaatg attccgttgc tttagtgctg ggagataatg ttttttttatgg tgctgggtta
tcaaagctat tacaagatgg ggccgcaaag gaatctggcg ccacaatttt tgggtatcag
```

| Sequence | SEQ ID NO | Name |
|---|---|---|
| gtaactgatc ctgaacgttt tggtgtagta gaatttgata gccatcaaca cgctgtatcg<br>attgttgaaa agccaaccca tccacgcagt aattatgcag taactggttt gtatttttat<br>gataatgatg tggttaatat tgcaaaaaat gtaaagccat ctgcgcgtgg cgaacttgaa<br>attaccgatg tgaatgagga atatcttcgt cgcgggcagc tagatgtaaa agttatgggc<br>agaggttatg cttggttaga tactggaacg catgactcat tgcttgctgc ttcaagtttt<br>gttgcaacta ttgagaatca acaaaatctt aaagtggcgt gtcttgagga aattgcttat<br>cgtatggggt atattaatct tgaacgttg gaagaacttg cccagccgct caaaaaaat<br>gattatggtc agtatttgtt gcgtttggtc aaggaggaga gtaagtaatg gctttaaaag<br>taatcccgac aaagttaact gatgtcaagt tggttgagac agatgttttt ggtgataatc<br>gcggtttctt cacagaaacg tatactcgac ctaagtttcaagaggcgggc atcacgaatg<br>atttcaatca agataatcag tcattgtctg ctgaagcagg tgtgttaaga ggcatgcact<br>accagatggc tccacatgca caaacaaaat tagttcgtgt ggtaactggt gttgttgaag<br>atgtttggt tgacatccga aaggggttcac caacttatgg tcagtgggaa ggatatattt<br>taagcgaatt caaccatcgc caattacttg tgccaaaggg gtttgctcat gggtttatta<br>cattaactcc aaatgttaat tttgcttata aggttgaagg gtattatgct cctgaagctg<br>atcgtggaat tgcctttgat gatcctgaca ttggcattaa ttggccaatg tcaacagcac<br>accttattat gtctgagaag gatcaacacc atccacagct gagggatgct gaaaataact<br>ttgtatacgg ggagatttga taatgaaact tatgatcact ggcggggctg ggtttatcgg<br>ttcaaatttt gttcattttg tttataataa ccatccagat gttcagatta tggttttgga<br>caagctaaca tatgccggca ataaggccaa tattgaagat atcttgggcg atcgtgtcaa<br>attagaagtc ggggatattg ccgacaagaa tttggtcgat aaattgatga gtgaagtcga<br>tacagttgtc aactttgcgg cagaaagtca caatgacaat tcgttgatta atccggatcc<br>gttcctgcac agcaatgtta ttggcaccta tactttactt gaagcagcaa gaaagtacga<br>tgttcgattc caccatattt ccacagatga ggtgtacgga gatctaccat tacgtcgtga<br>tcttccagga cacggggaag gccctgcgca gaagttcacc gttaacagtc gttataatcc<br>ttccagccca tattcttcaa ctaaagctgc cagtgacatg ttggtacatg catgggcacg<br>ttcatttggc gtacgcgcaa caatttctaa ttgctcgaat aactatgtc cataccaaca<br>cattgagaaa ttcattcctc ggcaaatcac aaacatttta agcggaatca aaccgaagct<br>ttatggcact ggcaaaaatg ttcgtgattg gattcacaca aacgatcatt caagtgctat<br>ctgggatatt ttgactaacg ggaaaattgg tgagacttac ttgatcggcg ccaatggcga<br>aaaagacaat aagacggtac tcgaacttat cttaaaattg atgggcaaac cagctgatta<br>ctatgaacag gttaaggatc gtccggggca tgatatgcga tatgccattg atgcttccaa<br>aacccgtgaa gaacttggtt gggaacctca gtatacgaat tttgaagaag gtttagcaga<br>taccatcaaa tggtacacag atcatcacag ctggtggcaa ggtgaaaaga<br>ctgcggtaga agaaaagtac caagaaacg gtcaatgact ttagctcata gtaatggtcg<br>tcactaatta tgaacctgtt attttctgga atgtcgagga agatacat gaagactttg<br>attactggtg cgcaaggtca gcttggtaca gaattgcgcc gcctattaga tgcgcaggge<br>gttgcttatc gagcaacaga tgcccatgat ttagacatta ctgatgagac tgcggttaat<br>cagtatttta aagattatca acccgagtta gtttatcact gtgctgccta acggctgtc<br>gataaggctg aaggtgaagc taaggcaatt aatcaaaaag ttaatgttga cggaacacgt<br>aatttggcaa aagcggccgc tgaagtagat gcgacacttg tttacatcag tacagattat<br>gtatttgatg gtgacagcaa agaaatttat accgtcgatg atcaacctgc tccacgtaat<br>gagtatggcc gggcaaaata tgaaggtgag caacaagtcc aaaaatatct taagaagttc<br>tatattatta gaacctcatg ggtattcggt gaatttggtc ataactttgt ttatacaatg<br>ttggacttag ccaagacaca caaagaactc agcgttgtca agatcaata cggtcgtccg<br>tcatggacca agacactcgc agaattcatg acgttcgcag tgaatcaaca tttgattat<br>ggcatttacc acttgtctaa tgataacagt tgtaactggt acgaatttgc tagcgctatt<br>ttggctgaca aagatgttga tgttaagcca gtatcgtcat cagagtatcc gcagaaggca<br>tggcgtccgc gacattcgat tttggactta gtaagacga aggttacagg cttttaagata<br>gacacttggc aagaagcttt gacaaacttt ttacaagtta tcgataaata agtgaaacta<br>gatcaagtgt atcaaaaaga acgtaaaaac caatctggcg attggtttcg cgcccctttt<br>gatacacgta acaataacgg gtctacactt tctggtgttg agaaataatc agcactgaac<br>gtgtaggccc tttttggata acgcaaaaag acacctattc agtgaccatg ctatgcttgt<br>tagcgtcgaa accaaaagca agcgaggtta tgagtaaatg tcccaatacg attctacact<br>gtccgtcctt ggaataccag accataatat caaagtagcc tttgttcgtc atgaatatcg<br>cggcaacggg gtacgtcgcc gccagtatca tgtgattgat gctgagctga cttaccggtt<br>acactgtgtg gctttgaggc cttgcaccct aacggttttt acacggccca tgtcgcgtc<br>ctcaacgggg ttgaaatgcc gacagtcatt gacttgcaca agcaacgatg gcgctgtcat<br>aactgttacc acacagtcag tgccaagacg ccactcgtgc aacccaacca<br>cacgatcgcc gctcacatga cagagcgaat catgaagtta gcgcatgaac ggttgccagt<br>caaaaccatc gcccgtatta tcggaatctc agcctcctcg gttcaacgga tcattgacca<br>aaatctcaaa ctccgaccgg ctcgccggct acccacggca tctgctttg atgagttccg<br>ttccactcat ggcatgatgt cgtttatctg tcttgatgcc gattcacatc atctgattgc<br>cttgcttggt gatcgatgca accgcacgat taaaaacttc ttcctcgctc attattcact<br>cgctgaacgc actcgggtcc agacggtcac catggacatg aatgcagctt atcagacgat<br>tattcatgag gtttttcccca aggcccaagt cgtcattgat cggttccata tcattcaact<br>tgcggctcgt gccctttgatc aggtacgcgt ccaagcgctc aaacagcttg atgacaaaca<br>cagccgtcct tataagatca tgaagacaaa ctggcggctt tttcatcaaa ctgcgcctga<br>cgctaaacac aaacagttcc tgtttggttt gaatgaagac gtcacgcaac aggaggccat<br>cgatattgca cttgatactg agcccaagct caagcaaacc tacgagacct acttagcgct<br>tcatgatgct ttgatggtga agaaacatcc cgcggaactg gcaaacctgt tagctactta<br>cgagccaaac ggtacgcgca tggacatgac gatcgcgacg cttaagcgac<br>acaaagtcgc tgttctcgcc gctgtcacca gccttattc caacggtccg atcgaagggt<br>taaccgcctc atcaagtcac tcaaacgatc ctgtttggc ttcaagaatc agctgaactt<br>cttcaaacga atcataccaa atcacggcat aacatgacaa agacggcggc<br>atgatcctga agctataata ggcgcagtaa tcaccttcag ggcaacgtga agctcatgcc<br>taatagaaat acgagagcgg cctaaggtcg cggcgatgta ttgaatcgtg tggtgttgca | | |

| Sequence | SEQ ID NO | Name |
|---|---|---|
| tcagttctat ctgagatcgt tcaattaagg ttataatggc catgggacct gtccttctct ctagatggta tgttatgcaa acaccatttt agcaagaacg gacaggtctt ttttcacatt ttctgggtgg taactttaat tatgcaatct aggcattaag ggtcaaatta ccagatgata atatgcctga ttcattaata atcgcgtgtg aaaaaggaac attaatctta ggagaattga tgatcg | | |

Figure 8:
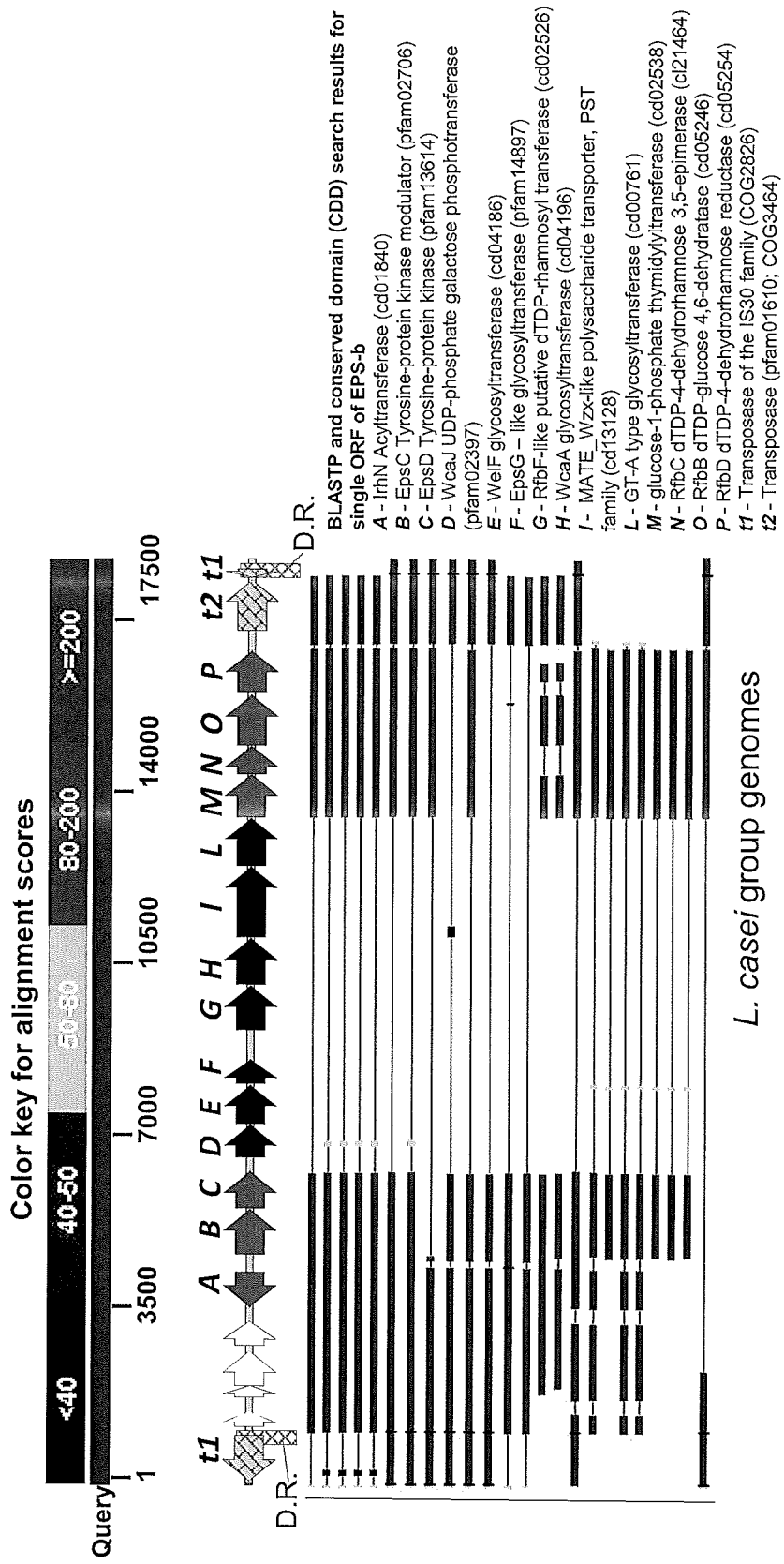
FIG. 8 shows the in silico predicted functional organization of the EPS-b region of *L. paracasei* DG; the figure shows the BLASTN search results for the region EPS-b and has been obtained by adding a picture of the putative EPS gene cluster over the graphic representation of the BLASTN output. In white are indicated open reading frames (ORFs) outside the putative EPS operon; in black are ORFs that do not share significant homology with other sequences in GenBank. D.R., direct repeat sequences.

As shown in FIG. 8 the regions codifying for the proteins A-P are fundamental for the synthesis/expression/secretion of the exopolysaccharide.

SEQ ID NO: 1 comprises T1 and/or T2 sequences corresponding to transposon sequences. These sequences can be used for insertional mutagenesis.

According to a preferred embodiment of the invention, SEQ ID NO: 1 or fragments thereof is introduced, eventually by using a vector, into a cell, preferably a bacterium.

This allows obtaining an engineered cell, preferably an engineered bacterium or yeast comprising SEQ ID NO: 1 or fragments thereof.

The engineered cell produces the exopolysaccharide of the invention.

A further aspect of the invention refers to a medium comprising the exopolysaccharide of the invention, preferably said medium being the conditioned medium where cells producing said exopolysaccharide have been grown. These cells are preferably bacteria or yeast, preferably genetically engineered. Alternatively, the cells producing the exopolysaccharide of the invention is L. paracasei DG strain, that is the bacterium that naturally produces the exopolysaccharide of the invention.

Preferably, the genetically engineered cells comprise the nucleic acid SEQ ID NO: 1 or any fragments thereof.

A further aspect of the present invention refers to a composition comprising the exopolysaccharide as disclosed above or the conditioned medium as disclosed above and further ingredients, preferably excipients.

A further aspect of the present invention refers to the exopolysaccharide of the invention or the conditioned medium of the invention or the composition comprising the exopolysaccharide or the conditioned medium of the invention in combination with any further probiotic bacteria or yeast. Preferably, the bacteria belong to the genus Lactobacillus and/or Bifidobacterium.

Preferably said Lactobacillus belongs to a specie selected from: Lactobacillus paracasei, Lactobacillus acidophilus, Lactobacillus rhamnosus, Lactobacillus amylolyticus, Lactobacillus amylovorus, Lactobacillus alimentarius, Lactobacillus aviaries, Lactobacillus brevis, Lactobacillus buchneri, Lactobacillus casei, Lactobacillus cellobiosus, Lactobacillus coryniformis, Lactobacillus crispatus, Lactobacillus curvatus, Lactobacillus delbrueckii, Lactobacillus farciminis, Lactobacillus fermentum, Lactobacillus gallinarum, Lactobacillus gasseri, Lactobacillus helveticus, Lactobacillus hilgardii, Lactobacillus johnsonii, Lactobacillus kefiranofaciens, Lactobacillus kefiri, Lactobacillus mucosae, Lactobacillus panis, Lactobacillus collinoides, Lactobacillus paraplantarum, Lactobacillus pentosus, Lactobacillus plantarum, Lactobacillus pontis, Lactobacillus reuteri, Lactobacillus sakei, Lactobacillus salivarius and Lactobacillus sanfranciscensis, more preferably is the strain Lactobacillus paracasei DG®.

Preferably said Bifidobacterium belongs to a specie selected from: B. animalis, B. B. angulatum, B. asteroides, B. boum, B. choerinum, B. coryneforme, B. cuniculi, B. denticolens, B. dentium, B. gallicum, B. gallinarum, B. indicum, B. inopinatum, B. lactis, B. magnum, B. merycicum, B. minimum, B. pseudocatenulatum, B. pseudolongum, B. pullorum, B. ruminantium, B. saeculare, B. subtile, B. thermacidophilum, B. thermophilum e B. tsurumiense.

Preferably said yeast is preferably Saccharomyces, more preferably Saccharomyces cerevisiae or Saccharomyces boulardii.

A further aspect of the present invention refers to the exopolysaccharide of the invention or the conditioned medium of the invention or the composition comprising the exopolysaccharide or the conditioned medium of the invention for use as a medicament.

Preferably, the exopolysaccharide of the invention or the conditioned medium of the invention or the composition comprising the exopolysaccharide or the conditioned medium of the invention is used in this context to boost immune system response in an individual in need thereof.

Therefore the exopolysaccharide of the invention or the conditioned medium of the invention or the composition comprising the exopolysaccharide or the conditioned medium of the invention is(are) useful as functional food and/or prebiotic.

In other words, the exopolysaccharide of the invention or the conditioned medium of the invention or the composition comprising the exopolysaccharide or the conditioned medium of the invention can be added to any food, such as milk, yogurt, cheese or juice to boost immune response.

Therefore, the exopolysaccharide of the invention or the conditioned medium of the invention or the composition comprising the exopolysaccharide or the conditioned medium of the invention can be useful as adjuvant for treating any disease or deficit or condition caused by impaired or compromised immune response.

Preferably, the disease or deficit or condition of the invention involves a downregulation of at least one cytokine, preferably selected from: IL6, IL8, TNF-α and CCL20.

Indeed, the examples herewith provided show clearly that the exopolysaccharide of the invention is able to increase the expression of cytokines, with particular reference to IL6, IL8, TNF-α and CCL20. Therefore, the boosting of immune system or its response is mainly due to its capability of activating cytokines, preferably pro-inflammatory cytokine expression.

The disease or deficit or condition preferably used to treat intestinal diseases, preferably selected from: autoimmune diseases, preferably rheumatoid arthritis, lupus erythematosus or myasthenia gravis, immunodeficiencies, allergy or hypersensitivity reactions and infections, preferably bacterial and/or viral.

Moreover, the exopolysaccharide of the invention or the conditioned medium of the invention or the composition comprising the exopolysaccharide or the conditioned medium of the invention can be useful as adjuvant for curing/treating non pathological conditions associated to stress, seasons change, vitamins deficiencies, preferably B112 and/or B119, age, pregnancy, alcohol abuse, drugs use and heavy metals poisoning, preferably lead and/or mercury.

EXAMPLE

Identification of the Putative EPS Gene Cluster

In light of the potential importance of EPS molecules in the cross-talk between probiotic bacteria and host, we performed in silico analyses to identify putative EPS operons in the draft genome of the probiotic strain L. paracasei DG.

The draft genome sequence of L. paracasei DG was obtained through Ion Torrent PGM (Life Technologies, Germany) as previously described (Guglielmetti et al, 2014). The raw sequence data were assembled using MIRA v.3.9 (http://www.chevreux.org/projects_mira.html), applying default parameters recommended for Ion Torrent data processing. Initial automated annotation of the genome was performed using RAST, combined with BLASTX. Results of the gene-finder program were combined manually with data from BLASTP analysis against a non-redundant protein database provided by the National Center for Biotechnology Information (NCBI). The L. paracasei DG draft genome sequence was compared with other L. paracasei genome sequences by means of BLAST Ring Image Generator (BRIG). The functional annotation of the EPS-b region was carried out by combining the results of BLASTN, BLASTP and the "CD-search" of the Conserved Domain Database (CDD) available at the NCBI website (http://www.ncbi.nlm.nih.gov/Structure/cdd/wrpsb.cgi).

The DNA sequence of the EPS-b region has been deposited in the EMBL database under the accession number LT629195.

Specifically, comparative analysis with other genomes of the same species led to the identification in the genome of strain L. paracasei DG of two different regions encoding open reading frames (ORFs) putatively involved in the biosynthesis of EPS molecules (regions EPS-a and EPS-b in FIG. 1). Notably, whereas EPS-a region is common to all L. paracasei genomes investigated, EPS-b is a 13 kb region coding for several putative glycosyltransferases that includes a region of about 7 kb in the center of the cluster that did not find any match with other sequences in GenBank according to BLASTN search. The % GC of the 7 kb region is much lower (36%) than the average GC content of L. paracasei DG's whole genome (approximately 46%) supporting the idea of the acquisition of these genes by horizontal gene transfer from a phylogenetically unrelated host.

EPS Isolation and Purification

Lactobacillus paracasei strain DG (deposited at the National Collection of Microorganisms Cultures of the Pasteur Institute under the code CNCM I-1572) was grown at 37° C. in de Man-Rogosa-Sharpe (MRS) broth (Difco Laboratories Inc., Detroit, Mich.) for 24 h. This culture was used to inoculate the chemically defined medium (CDM, Table 1).

TABLE I

| Component | Concentration (g l$^{-1}$) |
|---|---|
| Sol. 1 | |
| (NH$_4$)$_2$SO$_4$ | 2 |
| MgSO$_4$ × 7H$_2$O | 0.15 |
| MnSO$_4$ × 4H$_2$O | 0.02 |
| Sol. 2 | |
| Adenine | 0.005 |
| Pyridoxal | 0.002 |

TABLE I-continued

| Component | Concentration (g l$^{-1}$) |
|---|---|
| Nicotinic acid | 0.001 |
| Ca$^{2+}$-D-pantothenate | 0.001 |
| Riboflavin | 0.001 |
| Thiamine | 0.001 |
| Vitamin B12 | 0.000001 |
| Biotin | 0.00001 |
| p-aminobenzoic acid | 0.000005 |
| Folic acid | 0.00001 |
| Sol. 4* | |
| Guanine | 0.005 |
| Xanthine | 0.005 |
| Uracil | 0.005 |
| Sol. 5 | |
| K$_2$HPO$_4$ | 4.56 |
| Sol. 6 | |
| Sodium acetate | 0.05 |
| Sodium citrate | 0.02 |
| KH$_2$PO$_4$ | 0.01 |
| NaCl | 0.002 |
| CaCl$_2$ | 0.002 |
| Sol. 7 | |
| Tween 80 | 1 |
| Tween 20 | 1 |
| Glycerol | 1 |
| Glucose | 20 |
| Casaminoacids | 10 |

The multistep extraction and purification of EPS was performed from about 1 L of CDM supplemented with 2% glucose. After growth at 37° C. for 48 h, cells were collected by centrifugation at 12,000×g for 15 min at 4° C. (Avant J-26 XPI, Beckman Coulter Ltd, High Wycombe, UK) and separated from the exhausted medium. The two fractions were then treated separately. The exhausted medium was added with an equal volume of absolute ethanol and stored at 4° C. for 48 h. After storage, it was centrifuged at 25,000×g for 35 min at 4° C. The obtained pellet (fraction S1) was dissolved in deionized water (about 20-50 ml), whereas the supernatant was added to a second volume of ethanol and stored again at 4° C. for 48 h. Subsequently, the centrifugation step was repeated, and the pellet (fraction S2) was dissolved in deionized water as above. Concerning cell fractions, the pellet was washed with phosphate-buffered saline (PBS) to remove polysaccharide impurities and then treated with 1 M sodium hydroxide and stirred overnight at 4° C. Afterwards, it was centrifuged again at 12,000×g 4° C. for 15 min in order to remove sodium hydroxide. Crude EPS was precipitated by the addition of an equal volume of chilled absolute ethanol; this was stored 48 h at 4° C. and then centrifuged at 25,000×g 4° C. for 35 min. The recovered pellet (fraction C1) was re-dissolved in deionized water (about 20 ml). The resulting supernatant was then added to a second volume of absolute ethanol and again incubated 48 h at 4° C. Another centrifugation, as described above, a second precipitated fraction (C2) was recovered, which was dissolved in deionized water. Small neutral sugars and proteins were then removed by dialysis (with 100 kDa cut-off cellulose acetate membranes) of the extracted fractions for 72 h at 4° C., against three changes of deionized water per day. After three days, the contents of the dialysis membrane were collected and lyophilized in a freeze-dryer (Northern Scientific, York, UK). The dry mass of EPS was then determined. The presence of contaminating bacterial DNA in the EPS preparations was tested through real-time quantitative PCR (qPCR) with two primer pairs: universal primers targeting 16S rRNA gene (EUB), and DG strain specific primers targeting welF gene. This analysis revealed the presence of 10-63 ng ml-1 in the 1 mg ml-1 stock solutions of EPS, corresponding to an overall maximum concentration of 0.6 ng ml-1 of DNA incubated with THP-1 cells when the highest concentration of EPS (10 μg ml-1) was used in immunological experiments.

The results show that, although growth was slower than that observed in more conventional media such as MRS broth, CDM was chosen as it does not contain contaminating polysaccharides which interfere with the characterization of bacterial polysaccharides by NMR. In order to isolate a sample of polysaccharide suitable for characterization, L. paracasei DG was grown for three days, at which point the cell biomass was separated from the fermentation liquors by centrifugation. High purity EPS was isolated from the supernatant by fractional precipitation of material. Adding one volume of ethanol released small amounts of an EPS material contaminated with proteins (typically 20-25 mg from a 500 ml batch fermentation). The addition of a second volume of ethanol also precipitated a relatively small amount of EPS (20-25 mg) but with much greater purity and of a purity that was suitable for characterization by NMR. As the yields of EPS were low, and in order to determine if additional material was being retained with the biomass, various different methods were attempted in order to recover capsular material bound to the cells. Stirring a suspension of the cells overnight in an aqueous solution of sodium hydroxide (1 M) and then precipitating crude polysaccharide by adding two volumes of ethanol yielded a significant amount of material which included both polysaccharide and protein. The same approach was adopted for the isolation of extracellular polysaccharide molecules from strain L. paracasei LPC-S01.

Figure 2:
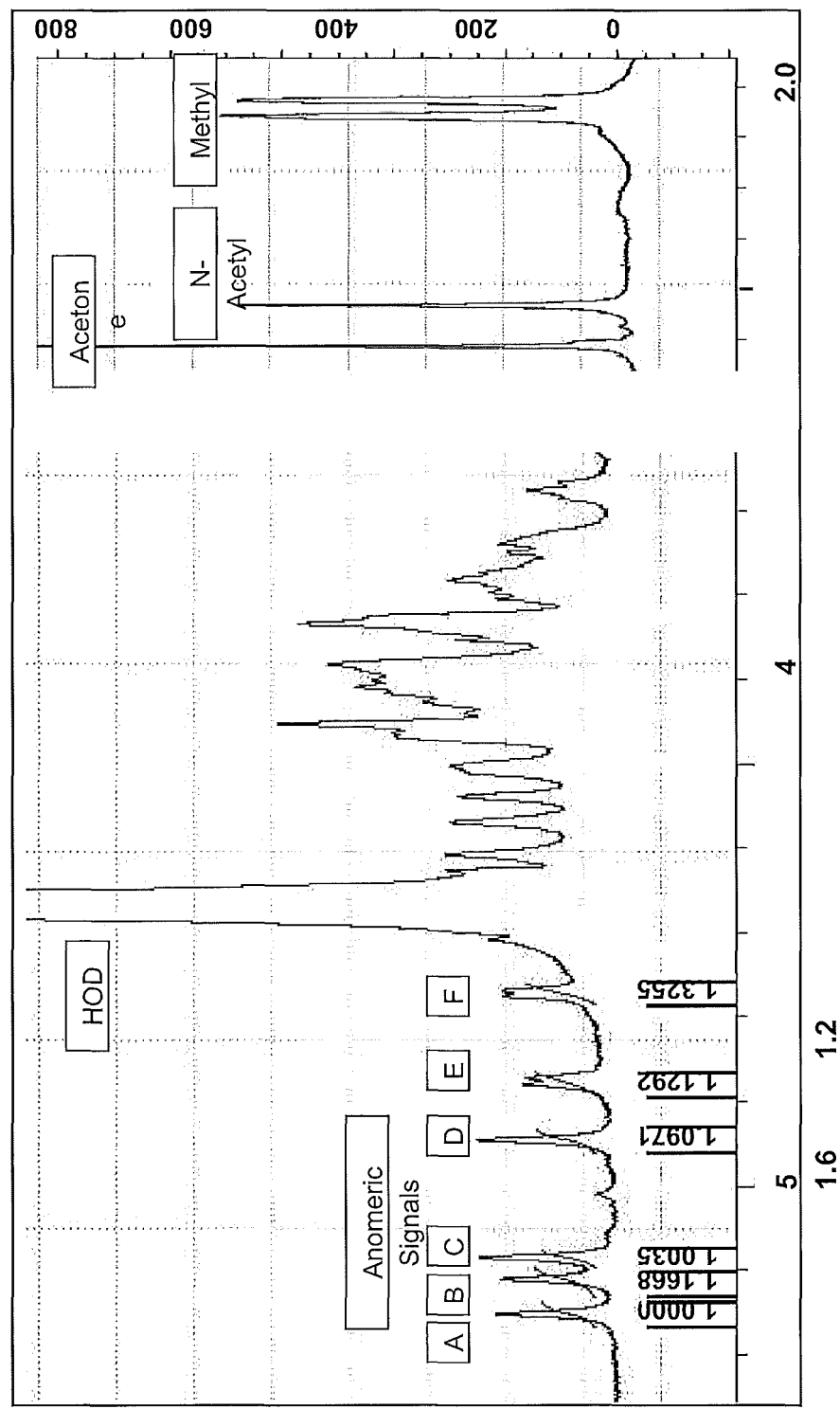
FIG. 2 shows the NMR analysis of the exopolysaccharide (EPS) isolated from *Lactobacillus paracasei* DG. In particular.

The purity of the EPSs released into the supernatant was established by examination of a 1H-NMR spectrum of the sample (FIG. 2). The low-field region of the spectrum contained six anomeric signals. Within the error of the experiments, the peak area integrals for each of the anomeric signals were the same, implying that a single EPS having a repeating unit containing six monosaccharides had been isolated. In addition to the anomeric signals, a single resonance with an integral height of three was visible at a chemical shift of 2.05 ppm which is indicative of the presence of an N-acetylhexosamine and a further two sets of overlapping doublets, each integrating to six protons, were present at 1.25 &1.32 ppm; these signals indicated that the repeat unit contained four 6-deoxyhexoses.

Determination of Monomer Composition and Linkage Analysis

To determine the monomer composition of the polysaccharide, the EPS (3 mg) was hydrolyzed by treatment with 2 M trifluoroacetic acid (TFA, 120° C. for 2 h); the released monosaccharides were subsequently derivatized to form alditol acetates, which were analyzed by gas chromatography-mass spectrometry (GC-MS). To derivatize the monomers, the mix resuspended in 1 ml Milli-Q water was added with 10 mg NaBH4 and incubated at 40° C. for 2 h. After evaporation of the solution, 1 ml glacial acetic acid was added to the residue, and again evaporated to dryness. Subsequently, 3 ml methanol were added and then evaporated in order to remove the borate complex and to give the methylated sugar alditols. They were then added with 2 ml pyridine and 2 ml acetic anhydride; acetylation reaction ran at 100° C. for 2 h. At the end of the reaction, the solution was evaporated and the acetylated monomers resuspended in water. Extraction with chloroform was performed to collect the organic phase, containing the alditol acetate sugars. Any trace of water was removed by adding anhydrous sodium sulphate and storing the sample 30 min at 4° C. Sodium sulphate was removed by filtration on filter paper and chloroform by evaporation. The resulting residue was resuspended in acetone. The GC-MS analysis was performed on an Agilent 7890A GC system (Santa Clara, Calif., USA) coupled to an Agilent 5675c quadrupole MS. The samples were eluted from a HP-5 column (30 m×0.25 mm id, 0.25 μm film) using helium as carrier (9 psi, flow rate 1 ml min-1) and using a temperature program (start temperature 150° C., hold time 4 min, and a final column temperature of 250° C. reached via a rising gradient of 4° C. min-1). The ratios of the different sugars were determined by examination of the relative responses of the different alditol acetates with reference to the relative responses determined for a standard mixture of alditol acetates. The integral area for amino sugars was low, and this is a result of their having undergone thermal decomposition during analysis. The final monomer ratio, for the amino sugar, was taken from integration of the nuclear magnetic resonance (NMR) peak integrals for the respective anomeric and H2 protons. The absolute configurations of monosaccharides were determined by conversion to their 2-butyl glycosides using the procedure described by Gerwig et al. 1979. To determine the linkage pattern of the EPS, the sample was permethylated using the procedures described by Ciucanu and Kerek, 1984. The permethylated polysaccharide was then hydrolyzed (2 M TFA, 120° C. for 2 h) and the methylated monosaccharides converted to methylated alditol acetates. The identity of the methylated alditol acetates was determined by analysis of their individual mass spectrum fragmentation patterns generated during GC-MS analysis. The GC-MS analyses were performed on the same instrumentation as the monomer analysis but using the following temperature program: start temperature 155° C., hold time 1 min, and a final column temperature of 195° C. reached via a rising gradient of 0.75° C. min1.

GC-MS analysis of the alditol acetates generated during monomer analysis of the EPS identified the presence of 1,2,3,4,5-penta-O-acetyl-L-rhamnitol, 1,2,3,4,5,6-hexa-O-acetyl-D-galactitol, and 2-acetamido-1,3,4,5,6-penta-O-acetyl-2-deoxy-D-galactitol in a ratio of 4:1:1. The results of the monomer analysis identified the presence of rhamnose, galactose, and N-acetylgalactosamine in the repeating unit.

The methylated alditol acetates generated during linkage analysis included: a 1,5-di-O-acetyl-2,3,4,6-tetra-O-methylhexitol which confirms that the galactose is present in its pyranose form as a terminal sugar; a 1,3,5-tri-O-acetyl-2-(acetylmethylamino)-2-deoxy-4,6-di-O-methylgalacitol, which confirms that the N-acetylgalactosamine is present in its pyranose form as a 1,3-linked monosaccharide; two 1,2,5-tri-O-acetyl-3,4-di-O-methyl-6-deoxyhexitols, which indicates that two of the rhamnose monomers are 1,2-linked; a 1,3,5-tri-O-acetyl-6-deoxy-2,4-di-O-methylhexitol, which indicates that one of the rhamnose monomers is 1,3-linked; and finally a 1,2,3,5-tetra-O-acetyl-6-deoxy-4-O-methylhexitol suggesting that the final rhamnose is a 1,2,3-linked rhamnose present as a bridging point in the repeating unit.

Conversion of the monomers to mixtures of their epimeric 2-butyl-glycosides confirmed that all the rhamnose monomers were of L-absolute configuration whilst both the galactose and N-acetylgalactosamine were of D-absolute configuration.

NMR Analysis of the EPS from L. paracasei

Nuclear magnetic resonance (NMR) spectra were recorded for EPS samples that were dissolved (10-20 mg ml-1) directly in D20 (Goss Scientific Instruments Ltd., Essex, UK). NMR spectra were recorded at a probe temperature of 70° C. NMR spectra were recorded on a Bruker Avance 500.13 MHz 1H (125.75 MHz 13C) spectrometer (Bruker-Biospin, Coventry, UK) operating with Z-field gradients where appropriate and using Bruker's pulse programs. Chemical shifts are expressed in ppm relative to internal acetone ($\delta$ 2.225 for 1H and $\delta$ 31.55 for 13C). Spectra recorded included: a 2D gradient-selected double quantum filtered correlation spectrum (gs-DQF-COSY) recorded in magnitude mode at 70° C.; total correlation spectroscopy (TOCSY) experiments recorded with variable mixing times (60, 90, 120 ms); 1H-13C heteronuclear single quantum coherence (HSQC) spectra (decoupled and coupled); a heteronuclear multiple bond correlation (HMBC) spectrum; and finally, a rotating frame nuclear Overhauser effect spectrum (ROESY). The 2D spectra were recorded with 256 experiments of 1024 data points. The ROESY spectrum was recorded using a Bruker pulse sequence and 256 experiments of 1024 data points using a mixing time of 200 ms. For the majority of spectra, time-domain data were multiplied by phase-shifted (squared-) sine-bell functions. After applying zero-filling and Fourier transformation, data sets of 1024-1024 points were obtained.

The chemical shifts of each of the protons and carbons in the repeat unit were determined through the inspection of a series of 1D & 2D NMR spectra (Table II).

TABLE II

| Position | A | B | C | D | E | F |
|---|---|---|---|---|---|---|
| H1 | 5.30 | 5.21 | 5.15 | 4.87 | 4.72 | 4.53 |
| (C1) | (102.6) | (102.2) | (102.4) | (102.5) | (103.5) | (106.0) |
| H2 | 4.21 | 4.07 | 4.13 | 3.90 | 3.82 | 3.59 |
| (C2) | (79.8) | (79.6) | (80.3) | (71.6) | (57.1) | (72.5) |
| H3 | 4.01 | 3.91 | 3.86 | 3.79 | 3.65 | 3.63 |
| (C3) | (78.2) | (72.0) | (71.3) | (79.5) | (83.1) | (76.5) |
| H4 | 3.67 | 3.49 | 3.35 | 3.55 | 3.54 | 3.93 |
| (C4) | (70.4) | (73.6) | (73.7) | (72.9) | (72.6) | (70.1) |
| H5 | 3.82 | 3.77 | 3.66 | 4.02 | 3.45 | 3.53 |
| (C5) | (70.6) | (70.6) | (73.8) | (70.5) | (77.3) | (70.0) |
| H6 | 1.32 | 1.32 | 1.25 | 1.25 | 3.91/3.75 | 3.75 |
| (C6) | (18.6) | (18.1) | (18.0) | (17.9) | (62.4) | (62.3) |
| Acetyl (CH$_3$CO) | | | | | CH$_3$ $\delta$ 2.05 CH$_3$ $\delta$ 23.5 CO $\delta$ 175.6 | |

Figure 3:
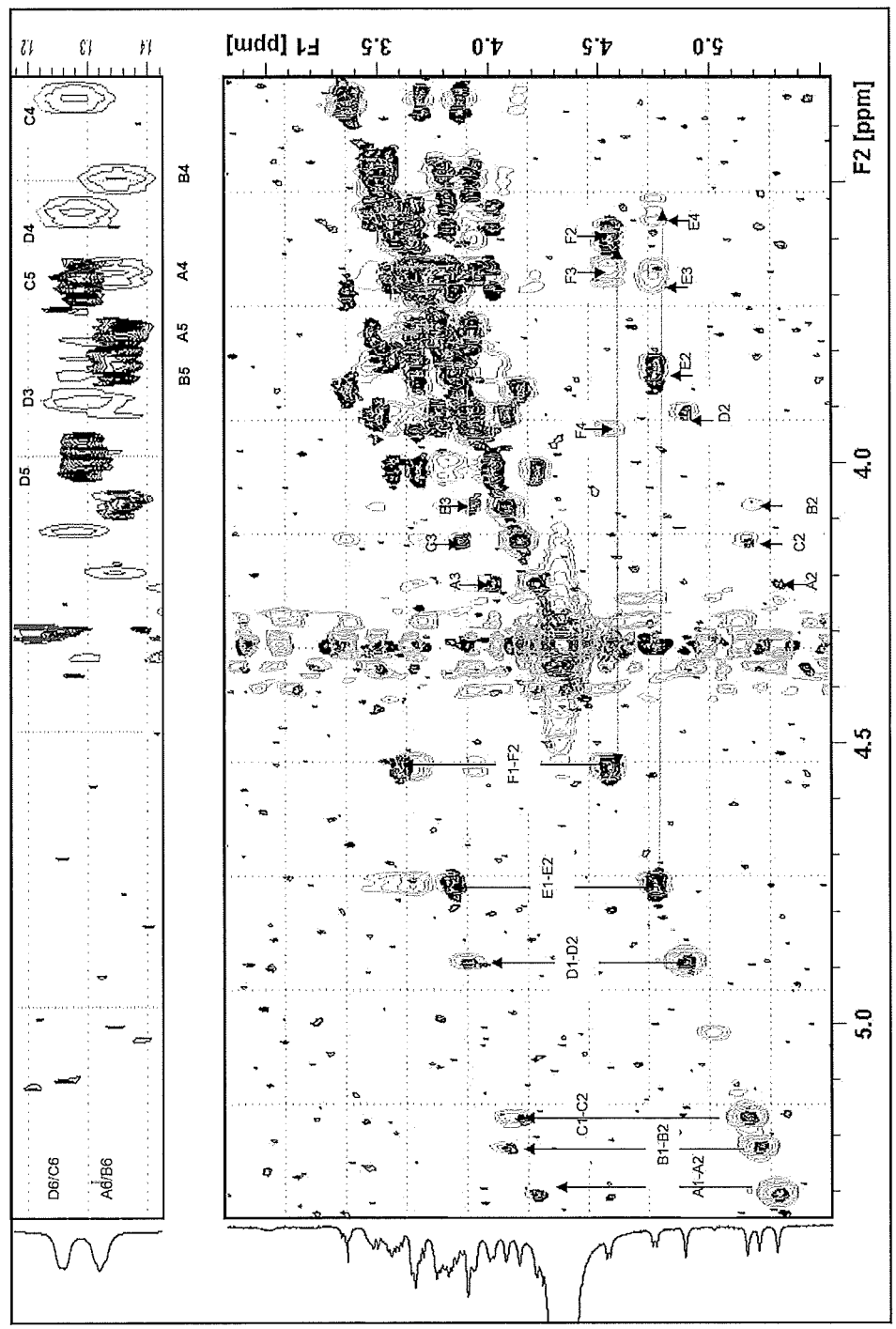
FIG. 3 shows the NMR analysis of the exopolysaccharide (EPS) isolated from *Lactobacillus paracasei* DG. In particular.

Analysis of the 1H-1H COSY spectrum (FIG. 3, black contours) in combination with the 1H-1H TOCSY spectrum (FIG. 3, grey contours) allowed the scalar coupling within the individual sugars to be tracked from the anomeric protons (labelled A to F in order of decreasing chemical shift-see FIG. 2) from H1 to H6 in the rhamnose sugars (A, B, C, and D) and from H1 to H4 in the galactose and N-acetylgalactosamine monomers (FIG. 3).

Figure 4:
FIG. 4 shows the NMR analysis of the exopolysaccharide (EPS) isolated from *Lactobacillus paracasei* DG. In particular.

A HSQC spectrum was used to correlate ring carbons with their attached protons (FIG. 4) and the distinctive position of C2 and identification of H2 of the N-acetylgalactosamine confirmed, by observation of scalar coupling to H1 resonance at 4.72 on the COSY spectrum, that the anomeric resonance at 4.72 ppm (E in FIG. 2) was that of the N-acetylgalactosamine. The remaining anomeric resonance at 4.53 ppm must therefore belong to the terminal galactose.

Through inspection of the carbon chemical shifts of the rhamnose ring carbons, it was possible to identify points of linkages by locating those carbons whose chemical shifts had moved towards low-field positions (above 78 ppm) compared to the values normally associated with unsubstituted ring positions (less than 74 ppm for rhamnose sugars). This identified A as a 2,3-linked rhamnose (C2, $\delta$ 79.8 ppm; C3, $\delta$ 78.2 ppm), B as a 2-linked rhamnose (C2, $\delta$ 79.6 ppm), C as a 2-linked rhamnose (C2, $\delta$ 80.3 ppm), and D as a 3-linked rhamnose (C3, $\delta$ 79.5 ppm). The results of the linkage analysis already identified that the N-acetylgalactosamine (E) is 1,3-linked, and this was confirmed by the high chemical shift of C-3 in E ($\delta$ 83.1 ppm). Finally, the chemical shifts of the carbons in residue F are in agreement with this being a terminal galactose monomer.

Figure 5:
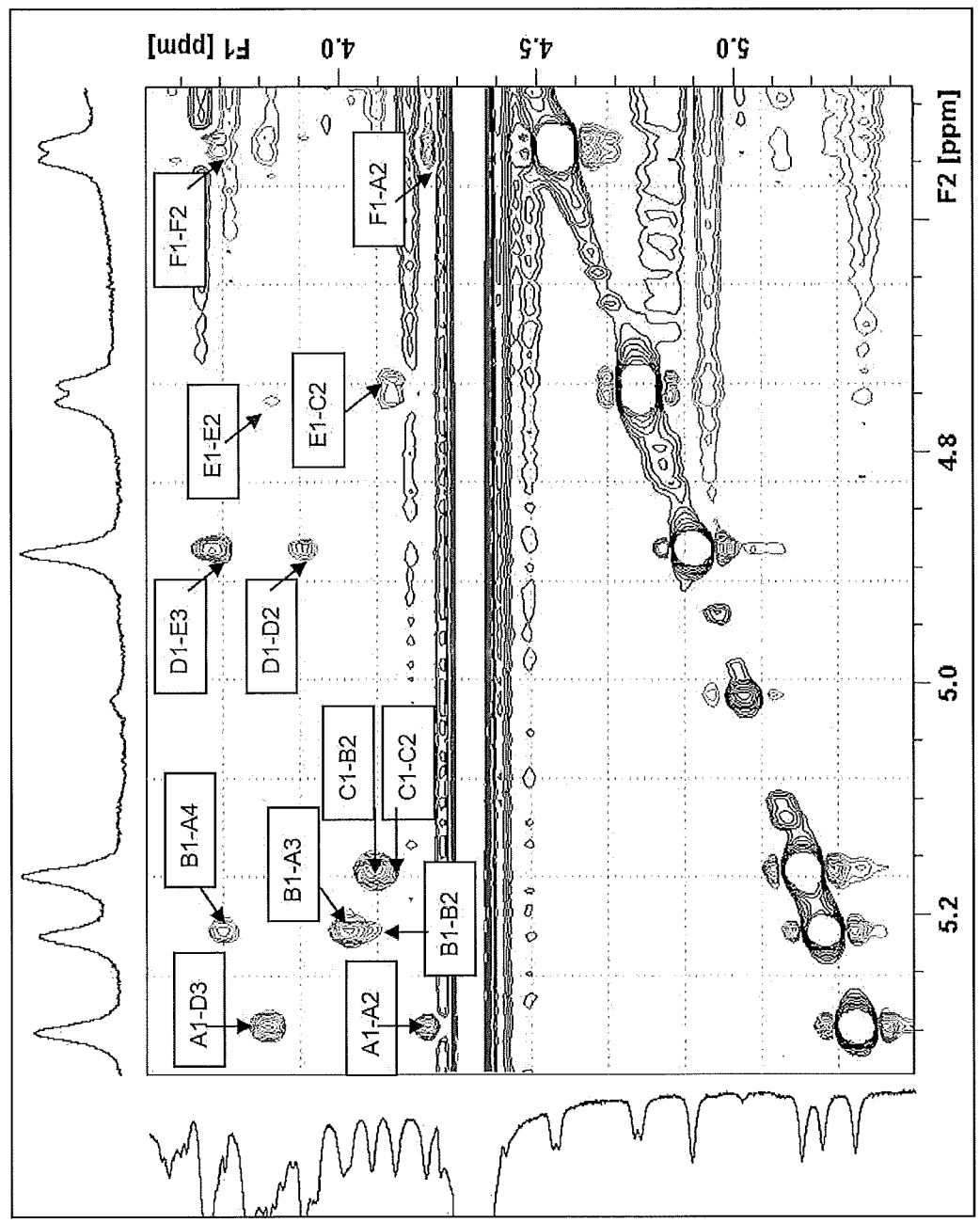
FIG. 5 shows the NMR analysis of the exopolysaccharide (EPS) isolated from *Lactobacillus paracasei* DG. In particular.

The anomeric configuration of the monosaccharides was determined by measuring the 1JC1-H1 coupling constants which were visible on a coupled HSQC spectrum. Residues A to D had 1JC1-H1 coupling constants A (177 Hz), B (172 Hz), C (175 Hz), and D (174 Hz) which are more than 170 Hz, which indicates that the rhamnose residues are alpha-linked, whilst the size of the 1JC1-H1 coupling constants in E (164 Hz) and F (157 Hz) identifies these two resonances as beta-linked monomers. Finally, the sequence of the sugars in the repeating unit was established through inspection of both a 1H-13C-HMBC spectrum and a 1H-1H-ROESY spectrum (FIG. 5). Inter-residue scalar coupling observed on the HMBC spectrum included: coupling between A-H1 & D-C3, indicating A is linked to the 3-position of D; coupling between C-H1 & B-C2, indicating C is linked to the 2-position of B; coupling between D-H1 & E-C3, indicating D is linked to the 3-position of E; coupling between F-H1 & A-C2, indicating F is linked to the 2-position of A. On the ROESY spectrum, inter-residue NOEs were observed: between A-H1 & D-H3, confirming the A(1-3)D linkage; between B-H1 and A-H3 (strong) and A-H4 (moderate), identifying that B is linked to the 3-position of A; between C-H1 & B-H2, confirming the C(1-2)B linkage; between D-H1 & E-H3, identifying a D(1-3)E linkage; between E-H1 & C-H2, identifying the E(1-2)C linkage; and also between F-H1 & A-H2, confirming the F(1-2)A linkage.

Figure 6:
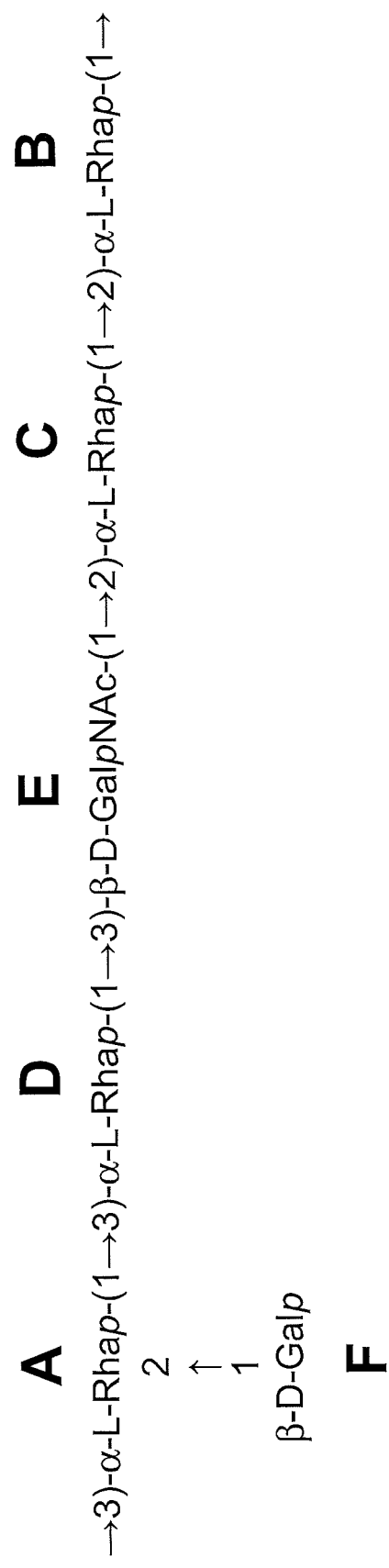
FIG. 6 shows the repeating unit structure of DG-EPS, i.e. the heteropolysaccharide isolated from *Lactobacillus paracasei* DG.

The combined results of the chemical and NMR analysis of the EPS isolated from *L. paracasei* DG indicates that the DG-EPS is a novel heteropolysaccharide having the repeating unit structure reported in FIG. 6.

Bacterial Adhesion to Caco-2 Cell Line

In order to investigate the potential ability of the DG-EPS to mediate the bacterium's interaction with the host, we first used the Caco-2 cell line, which is considered a valuable in vitro tool for studying the mechanisms underlying the interaction between bacterial cells and the human gut.

The adhesion of *L. paracasei* strains to Caco-2 (ATCC HTB-37) cell layer was assessed as previously described in Balzaretti et al, 2015. In brief, for adhesion experiments, fully differentiated Caco-2 cells were used (i.e., 15 days after confluence). 100 µg ml-1 EPS was incubated with a monolayer of Caco-2 cells for 1 h at 37° C. Finally, monolayers were examined microscopically (magnification, 400×) under oil immersion after Giemsa staining. All experiments were performed in duplicate.

The potential involvement of DG-EPS was assessed by testing also the adhesion ability of strain DG after removal of the EPS molecule ("naked" DG cells, nDG, prepared through PBS washes and mild sonication) and upon pre-incubation of Caco-2 cells with purified EPS.

The results demonstrate that purified EPS was unable to affect the adhesion properties of strain DG. In fact, the adhesion of *L. paracasei* DG was not significantly different from that of nDG and was quite modest (about 300 bacteria per 100 Caco-2 cells); in addition, the adhesion ability was unaffected by the co-incubation of the bacterial cells with purified EPS.

Nuclear Factor kB (NF-kB) Activation by Exopolysaccharides

The activation of nuclear factor KB (NF-kB) was studied by means of a recombinant Caco-2 cell line stably transfected with vector pNiFty2-Luc (InvivoGen, Labogen, Rho, Italy). Recombinant Caco-2 monolayers (approximately $3\times10^5$ cells/well), cultivated in the presence of 50 μg ml-1 zeocin, were washed with 0.1 M Tris-HCl buffer (pH 8.0) and then suspended in fresh Dulbecco's Modified Eagle Medium (DMEM) containing 100 mM HEPES (pH 7.4) and with 0.1 ml of *L. paracasei* DG-EPS, corresponding to a final concentration of 100 μg ml-1. The stimulation was conducted by adding 10 ng ml-1 of interleukin (IL)-1β. After incubation at 37° C. for 4 h, the samples were treated, and the bioluminescence was measured as described by Stuknyte et al., 2011. Two independent experiments were conducted in triplicate for each condition.

Recently it has been showed that *L. paracasei* DG possesses an evident ability to reduce NF-kB activation in Caco-2 cells at baseline and upon stimulation with the pro-inflammatory cytokine IL-1 (Balzaretti, 2015), as determined through a reporter system obtained by transfecting Caco-2 cells with a luciferase reporter vector. Here, the same immunological model has been used to test the EPS macromolecule isolated from strain DG. The results show that the purified EPS molecule, differently from the whole bacterial cells and their exhausted broth, was unable to affect NF-kB activation both at baseline and in the presence of the pro-inflammatory stimulus IL-1β (data not shown. Other *L. paracasei* strains under study (namely, strains LPC-S01 and Shirota) displayed the same ability of strain DG in reducing NF-kB activation in Caco-2 cells (13), further suggesting that DG-EPS does not contribute to this specific immunomodulatory effect.

Activation of THP-1 Human Macrophage Cell Line: Cell Culture, Growth Conditions, and Stimulation Protocol The monocytic THP-1 cell line was purchased from the American Type Culture Collection (Manassas, Va., USA). THP-1 cells were originally cultured from the peripheral blood of 1-year child with acute monocytic leukemia. They are non-adherent cells, which can be differentiated into macrophage-like cells through a protein kinase C-mediated reactive oxygen species (ROS)-dependent signaling pathway by treatment with phorbol myristate acetate (PMA). The normal growth medium for THP-1 cells consisted of RPMI 1640 medium (Lonza, Basel, Switzerland) supplemented with 10% (v/v) fetal bovine serum (FBS) (Gibco-BRL, Life Technologies, Milan. Italy), 2 mM L-glutamine, 100 units ml-1 penicillin and 100 μg ml-1 streptomycin (Sigma-Aldrich). Cells were seeded at a density of $5\times10^5$ cells/well in 24-well plates and incubated at 37° C. in a humidified atmosphere of 95% air and 5% $CO_2$. Differentiation was induced by the addition of PMA (Sigma-Aldrich) into the cellular medium at a final concentration of 100 nM and was allowed to proceed for 24 h. Afterwards, cells were washed once with sterile PBS buffer to remove all non-adherent cells, and fresh complete medium was added. Bacteria were used at the multiplicity of infection (MOI) of 50, EPS at final concentrations of 0.1, 1, and 10 μg ml-1; lipopolysaccharide (LPS) from *Salmonella enterica* (Sigma-Aldrich) was used at a final concentration of 1 μg ml-1. An untreated sample, i.e., only RPMI 1640 medium with 10% (v/v) FBS, was used as control.

Preparation of RNA and Real-Time Quantitative PCR (qRT-PCR)

After incubating THP-1 cells at 37° C. for 4 h, the supernatant was carefully removed from each well, and the total cellular RNA was isolated from the adhered cells with the Total RNA Blood and Cultured Cells Kit (GeneAid, New Taipei City, Taiwan). Afterwards, traces of DNA were removed by treatment with DNAse enzyme (Sigma-Aldrich), following the manufacturer's instructions. RNA concentration and purity was determined with a Take3 Multi-volume Plate Reader (Biotek, Luzern, Switzerland), and reverse transcription to cDNA was performed with the iScript™ Select cDNA Synthesis Kit (Bio-Rad Laboratories, Hercules, Calif.), using the following thermal cycle: 5 min at 25° C., 30 min at 42° C., and 5 min at 85° C. Real-time Quantitative PCR (qRT-PCR) was carried out in order to measure the mRNA expression levels of cytokines by means of the SYBR Green technology using the SsoFast EvaGreen Supermix (Bio-Rad) on a Bio-Rad CFX96 system according to the manufacturer's instructions. The primers were as follows (5'13'):

```
                                         SEQ ID NO: 2
GAPDH forward, 5'-GGGAAGGTGAAGGTCGGAGT-3';
                                         SEQ ID NO: 3
GAPDH reverse, 5'-TCAGCCTTGACGGTGCCATG-3';

SEQ ID NO: 4
IL-6 forward, 5'-CGGTACATCCTCGACGGCAT;
                                         SEQ ID NO: 5
IL-6 reverse, 5'-TCACCAGGCAAGTCTCCTCAT-3';

SEQ ID NO: 6
IL-8 forward, 5'-TGTGGTATCCAAGAATCAGTGAA-3';
                                         SEQ ID NO: 7
IL-8 reverse, 5'-TATGTTCTGGATATTTCATGGTACA-3';

SEQ ID NO: 8
CCL20 forward, 5'-CTGCTTGATGTCAGTGCTG;
                                         SEQ ID NO: 9
CCL20 reverse, 5'-CACCCAAGTCTGTTTTGG-3';

SEQ ID NO: 10
TNF-α forward, 5'-TCAGCTCCACGCCATT-3';
                                         SEQ ID NO: 11
TNF-α reverse, 5'-CCCAGGCAGTCAGATCAT-3';

SEQ ID NO: 12
COX-2 forward, 5'-CCCTTGGGTGTCAAAGGTAA;
                                         SEQ ID NO: 13
COX-2 reverse, 5'-TGAAAAGGCGCAGTTTACG-3'.
```

All primers were designed previously, and their specificity was assessed with melting curves during amplification and by 1% agarose gels. Quantitative PCR was carried out according to the following cycle: initial hold at 95° C. for 30 s and then 39 cycles at 95° C. for 2 s and 60° C. (for TNF-α and cyclooxygenase COX-2) or 58.2° C. (for IL-6, IL-8 and CCL20) for 5 s. Gene expression was normalized to the reference glyceraldehyde-3-phosphate dehydrogenase (gapdh) gene. The amount of template cDNA used for each sample was 15 ng. All results regarding cytokine mRNA expression levels are reported as the fold of induction (FOI) relative to the control (namely unstimulated THP-1), to which we attributed a FOI of 1. Statistically significant differences have been determined through unpaired Student's t test with a two-tailed distribution.

The gene expression of the tumor necrosis factor (TNF)-α, the interleukin (IL)-6, the chemokine (C—C motif) ligand 20 (CCL20), the chemokine IL-8, and the cyclooxygenase (COX)-2 were quantified through qRT-PCR. Three concentrations of the purified DG-EPS molecule (0.1, 1, and 10 μg ml-1) were tested. The same experiments were performed in the presence of 1 µg ml-1 of the pro-inflammatory stimulus LPS.

Figure 7:
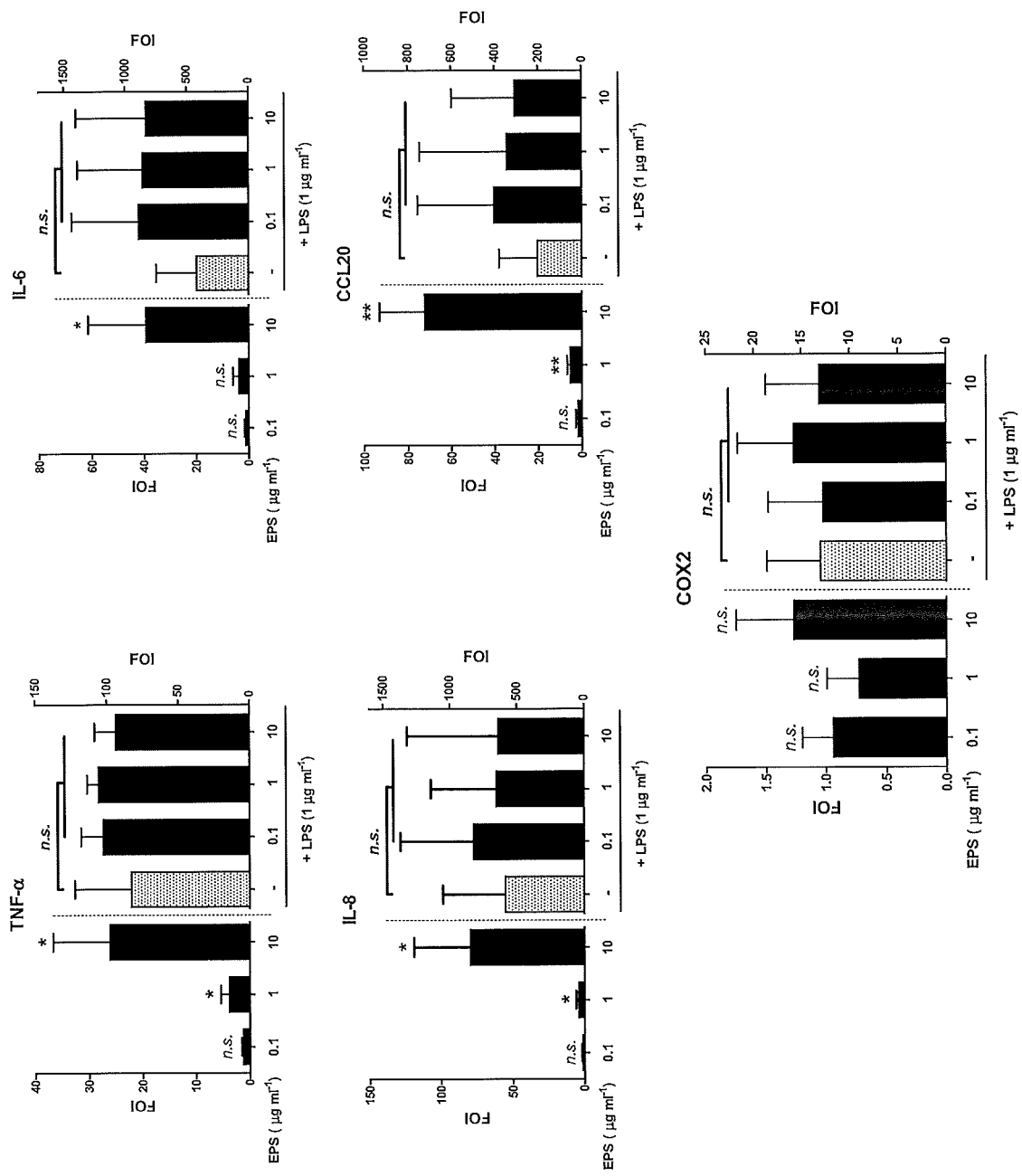
FIG. 7 shows the gene expression analysis by qRT-PCR in human macrophages THP-1 after 4 h stimulation with purified DG-EPS molecule (0.1, 1, and 10 μg ml-1), with or without the addition of LPS (1 μg ml-1). Expression levels of TNF-α, IL-6, IL-8, CCL20, and COX-2 are shown as the fold change of induction (FOI) relative to the control (unstimulated macrophages), which was set at a value of 1. Data are presented as mean of three independent experiments ±standard deviation. Asterisks indicate statistically significant differences (according to two-tailed unpaired Student's t test) compared to unstimulated (samples under the left Y axis) or LPS-stimulated (samples under the right Y axis) THP-1 cells: *, P<0.05; **, P<0.01.

The results show that the purified DG-EPS can stimulate the expression of all genes under study in a concentration-dependent manner, with the exception of COX-2 (FIG. 7). In particular, the chemokines IL-8 and CCL20 were induced approximately 70-fold by 10 µg ml-1 DG-EPS, whereas the pro-inflammatory cytokines TNF-α and IL-6 26- and 39-fold, respectively. A similar stimulatory profile was observed with bacterial cells of strain DG (MOI 50), even if to a lower extent (FIG. 8). In addition, when EPS was removed by PBS washes and mild sonication, the bacterial cells of strain DG lost their ability to stimulate the gene expression of TNF-α, IL-8 and CCL20; the addition of 1 µg ml-1 purified EPS partially reconstituted the stimulatory capacity of the cells (FIG. 8).

As expected, the stimulation of THP-1 cells with LPS determined a marked overexpression of all tested genes, particularly IL-6, IL-8, and CCL20. However, the addition of DG-EPS did not significantly affect the LPS-associated inductions of all tested genes (FIG. 7).

In conclusion, thanks to the genomic analysis on *L. paracasei* strain DG, we could identify two gene clusters putatively coding for EPS biosynthesis. Interestingly, Gen-Bank search revealed that one of these regions, EPS-b, is unprecedented.

After purification of the exopolysaccharidic cell fraction of strain DG, the EPS repeating unit was characterized by means of chromatographic methods and NMR spectroscopy, establishing that it possesses a novel structure.

Effectively, the repeating unit structures of a number of different strains of the *L. casei* group of species (i.e., *L. casei*, *L. paracasei*, and *L. rhamnosus*) have previously been published, and the one reported here is different.

Any EPS molecule with a different monosaccharide sequence may represent a potential novel MAMP.

DG-EPS displays immunostimulating properties in human leukemia monocytic THP-1 cells by enhancing the gene expression of the pro-inflammatory cytokines TNF-α and IL-6 and, particularly, the chemokines IL-8 and CCL20. On the contrary, the expression level of the cyclooxyqenase enzyme COX-2 was not affected.

The purified EPS produced by *L. paracasei* DG displayed an immunostimulatory activity, particularly in terms of chemokines expression. Thus, the EPS from *L. paracasei* DG, rather than an inert molecule, can be considered a bacterial product that can boost the immune system as either a secreted molecule released from the bacterium or also, Plausibly, as a capsular envelope on the bacterial cell wall.

In conclusion, the probiotic strain *L. paracasei* DG produces a unique rhamnose-rich hetero-exopolysaccharide, named DG-EPS, possessing immunostimulatory properties.

DG-EPS may represent a new molecule for potential nutraceutical and pharmaceutical applications.

The invention claimed is:

1. An exopolysaccharide comprising at least one repeating unit of rhamnose, galactose and N-acetygalactosamine, in a ratio of 4:1:1, respectively.

2. The exopolysaccharide according to claim 1, wherein the rhamnose is 1,2,3,4,5-penta-O-acetyl-L-rhamnitol; and/or the galactose is 1,2,3,4,5,6-hexa-O-acetyl-D-galactitol; and/or the N-acetygalactosamine is 2-acetamido-1,3,4,5,6-penta-O-acetyl-2-deoxy-D-galactitol.

3. The exopolysaccharide according to claim 1, wherein the rhamnose has L-configuration and/or the galactose has D-configuration and/or the N-acetygalactosamine has D-configuration.

4. The exopolysaccharide according to claim 3, wherein the repeating unit has Formula I

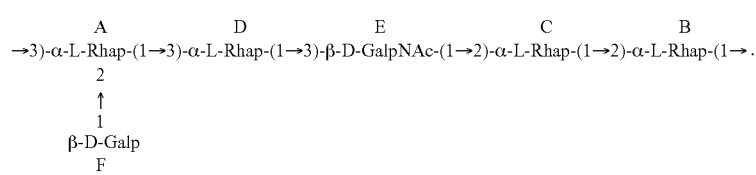

(Formula I)

5. The exopolysaccharide according to claim 1, obtained from the L. Lactobacillus paracasei DG strain deposited on May 5, 1995 at National Collection of Microorganisms Cultures of the Pasteur Institute under the code CNCM I-1572, or a mutant strain thereof.

6. A composition comprising the exopolysaccharide according to claim 1 and one or more excipients.

7. A composition comprising the exopolysaccharide according to claim 1 and one or more probiotics.

8. The exopolysaccharide according to claim 5, wherein said cells are bacteria.

9. The exopolysaccharide according to claim 5, wherein said bacteria cells are genetically engineered bacteria and/or bacteria from the Lactobacillus paracasei DG strain deposited on May 5, 1995 at National Collection of Microorganisms Cultures of the Pasteur Institute under the code CNCM I-1572.

10. The composition according to claim 7, wherein the probiotics comprise any bacteria belonging to the genus Lactobacillus and/or Bifidobacterium.

11. The composition according to claim 10, wherein said *Lactobacillus* is the specie *Lactobacillus paracasei*.

12. The composition according to claim 11, wherein the *Lactobacillus paracasei* is the strain *Lactobacillus paracasei* DG.

* * * * *

SEQUENCE LISTING

```
<160> NUMBER OF SEQ ID NOS: 13

<210> SEQ ID NO 1
<211> LENGTH: 18746
<212> TYPE: DNA
<213> ORGANISM: Artificial Sequence
<220> FEATURE:
<223> OTHER INFORMATION: Lactobacillus paracasei strain DG
      Exopolysaccharide-b region

<400> SEQUENCE: 1
ccatctttag attattaaat aatattatcc tagattgcaa taataaagtt accacctaga      60
aagaggcttg ctcactgctt gaactggggt ttgccaacgg agacattttc taggtttgtt    120
attgataaac gctgtggctc gttgaatatt ggcctctgaa acctgatcaa actgtgttcc    180
cttcgggaaa tagtagcgaa gttctcgatt gaaccgttcg ttcgtgcccc gttcattcgg    240
gtgataggca tggcaaaagt aaatcggtat ccgatgcgc tttgtaagcg cctgatcgca    300
ggaaaactct ttaccgtgat caaccgtcac tgatcgaacc ggacccggaa agtctaccat    360
cagtcttgca aatcctttga gaacagcatt ttgtgataag tttcaagct tagttgtcgc    420 cattaaacgt gtcacccgat cgacaatggt caaaacagca gcctttgacc cgcgaccacc    480
gcgaactgta tccatctcta aatgtcctt ttcggttcgc cgattagctg actcactgcg    540
aatctcaatt gaggtgccta ctgcttggtt atagcgcgac cgaaggtctt gtcttctttt    600
atgacgttta ccgtgatcaa agagttggct tggctgaaaa tcgacttgtc tttgataaat    660
ccagtggtaa atcgtgtgtg gcgcacagtg aacgacataa ccgaccattt caggggacca    720
acctaggttt agcttctcag ttaccatccg cttcaactta ggcgttaaaa tcgagtgccg    780
accacaacga tgccgacaag tatcggcatg atcctgagct ataatggcgc agtaatcacc    840
ttcagggcaa cggtgaagct catgcctaat agaaatacga gagcggccta aggtcgcggc    900
```

```
gatgtattga atcgtgtggt gttgcatcag ttctatctga gatcgttcaa ttaaggttat    960
aatggccatg ggacctgtcc ttctctctag atggtatgtt atgcaaacac cattttagca   1020
agaacggaca ggtctttttt cacattttct gggtggtaac tttaattatg caatctaggt   1080
tataaaatct tttgatagcc cggcgtttca tctaatgtta aagcataacg ccgcacatta   1140
aaggtggggg aaaccatgtt agacaatatc gggaaattgg tgcaccaaca gcgccgcagt   1200
ttgaacttga cgattgagaa gttggcggag cgatccggcg tctcgatcag tctgatttcg   1260
cgaatggagc gtggagacgt caacaatatc agcataaaaa aattgaccga cattgcgcgg   1320
gctttaaata tgcaggtagg cgacttcttt attgctccgg aaatgagcga tattagcaca   1380
ttagcggtgg tgaaatactt aacccactta ccagagaaag aacgggcgcg tgtttccgag   1440
gtactcatgc aggtgattaa cctgtaagta ccaccttttt agaacagtct gtcacttgag   1500
gctgttcttt tttgatatca aaaatgtcag aatgaccttaaaaggatggc gcaacccgtt   1560 gtcagtcagc tggtaaaacg cgtatactaa atgcactgat tttagacaat gaacgcgaac   1620
ttgcacggtt agcttggttt gacaaagtgg cactgaatag ttgatcaagt atttgttcgg   1680
ctaacaggct tcttcacaa taaccaaccg ccatgtggag aacgcatttt aaaagaagga   1740
gaatgatcga catgacattt gaagcaattt taccgtcctt taaagccggc aagaaggccg   1800
ttcgcaccgg ctgggaaggt actgagttgt atgtgcaact agttccggaa ggcaaattcg   1860
aaggcgacac tttgaatccg tatttttga tcaaaactgc cgacgaagct ttcagtctct   1920
ggtcaccgac tgactgtgac attttggctg aagactggca gcttgtgaac gcatgacgca   1980
tttcgacttc accgacaaga ccgtcatcat caccggcgcg gcttctggca tcggtgcggc   2040
tcaggcggcg gcttttcagg cagctggtgc cactgtggta ggaattgacc tccaaccaat   2100
tagcaacctc acagacgcca ttcaggccga tgtgagcgat cctgccacgg cagcagcgat   2160
tgcggctcaa taccagccag atattgtctg caatacggcg ggcgtgttgg atggttatca   2220
aactgtgacc gatacggcgc tctcggcatg gcagcacatt ctcgatgtcg atcctaccag   2280
tcagttctta atgatcaagg cgctgctgcc ggggatgctg gctcgcggtc acggtatttt   2340
catcaatatg agttccatcg ctggtttagt cggtggtggt ggcggcttgg cgtatactgc   2400
tgctaagcac gccgtcatcg tcctcaccaa gcaattagac cttgattacg ccgccaaggg   2460
cattcgcgcc aacgcgctcg caccaggcgc tatcaacacg cccatgaacg ccgctgattt   2520
tgccggcgac gggaaaatgg ctgcgtgggt agcgcgcgaa accccagcca aacgctgggc   2580
caagcccgag gaagtcgcac aattatcctt gtttctggcc agcgatgctg ctgattatat   2640
tcatggaacc gtgattccca ttgacggcgg ctggctcgaa aagtaaactt aatgcattgc   2700
aacaccaaaa ctgaaaacgg aaggcaatcc ttccacgacg atacttactt tcctttgatc   2760
gtcgttacta ctggcatagc cacaaaggag aacaaacatg caaacaactt caaccaccca   2820
tcgttcaatc gtcagtctcg ccaaaaccgc catgatcacg tccatttacg tcgtgatgac   2880
cctcatgctc agtccactca gcttcggggt cgtacaagtt cggttctccg agatgctcaa   2940
ctacacggca ctcttcaacc gccgttatgt ctggggcgtc acgctgggtg ttttttttggc   3000 caatttaacc tcgtcaaccg cactcctcga tgtcccaatc ggcaccctcg gcacgctcgt   3060
cttcatcatc atcagccgct ggttagccaa actcgtccaa ccaaaatggg ctaaattcac   3120
catcatgggt atccttttcg ccttatccat gttcaccatt gccggcgaac tgaccatcct   3180
cacaaaagtc ccattctggc caacctacgc taccatcgcg cttggcgaag ccatctcgat   3240
ggccgtcggt ggcgttgtga tgatgatttt gacgcgattt gtggatttgg ataagtaggc   3300
```

```
gataaggcta ttgaaagagg ctcctataga aaaaagctta ctggcaggaa aggtttcgct    3360
gaagcttttc gatctggcag aagggcaagc aggtctgatt gctgtgttca aaagttgtcg    3420
caggggttag gcttccgatg cacctgattt tggttaaata ttggttaaat acaaaaaagc    3480
atcaagacaa ttgtctcgat gcttttttta atggaaggga tacgccctaa atctttttta    3540
agcaagatgc taatcctagg taatgatggt cttttcattg ttacttttc aatgtctgca     3600 tgacatcctt agcaatcaac gtgtagtaat gcggccggcc agcgtcgttc ggatggacac    3660
cgtcatcagc aaaccagtcg tcattgccac ctgccagata ataccaatcc accacatgca    3720
gattggcatg ggttttagct gccgcatgaa tcagcttgtt aaccggatca atccacgctt    3780
tccccggagc atacgcggtc acccagaaga cctgacgctc agtcccaagc tgatccagaa    3840
tcccgttaat gtcggcctct gtcataggtc cgttcgtccc caaactgatc acaaccgtgt    3900
tagccaactt accacttgcc ttcagctgac taataatcgc aggtgctgcc tgcacctgcc    3960
gaccaacctc agcatcaatc gacatctccg gaaaaagcac cttcaaatat gccgaactcc    4020
ccagcataat cgaatcgcca atcgccgaca ccggcaatgt tttggccgca ttaatctcgc    4080
tgtcagttaa gccataaagc cgatactgat tcagaaccct tcccttcttc accttcgcct    4140
tagaatcctt ctgaatgcgc tgccgcgtcg attggttaac cgcaatcgcc tgctcagact    4200
gataatgctt gacgtagaag aaccccgcga ccagcagt tgccaatccc aacgcgatac       4260
ttaatagcca gtctcgtaga cgtagcttgt ttttttcat gatttagtga acccccaaaa     4320
tttgcattgc ttatatttta aactaaaaat caggttagtc tgattacaag ttagggtcat    4380
tctgacgggt ttataggaaa ctgtaaatag actgtaataa aatgaaattt gaagttacca    4440
accttagtaa aaggcgtgta tatcggattc aaactaatct gatagtacaa ccaaaaacat    4500
gacattcatt caaaacaggt agacttcgtc acacatgcta ggttattatg gtttggagta    4560
gagttttaaa agtctttttt agaaatgcgg gctgcgctgc ttgtggtccg cattttgagt    4620
gttggatata aattatggga ttaggtgggg aaagagttaa tgaacaagca aatcgacctt    4680
tcgcagttgt ggaatgtatt taaacgcagc tttgttgcaa tgattattct cggaattctt    4740
gggatggcgg ctgcttattt cggtgctaaa acgtttattt cgccaaaata tgagtctgat    4800
acgtcattgc tggtcaatcg caagcaggat aacgatccaa acatgcaatt gaatgctcag    4860
caggctgata ttcagatcat taatacatac aaggacatta tcacacgtcc agtcgtttta    4920
caggctgttg cgagtgaact aacaagtccc cagcgtgtat tgataaaaaa agctacaaag    4980
gcggtttatg gtacgcgtta caatgcaaca acaggtgttc gagaagaata tgttactcaa    5040
aaagctcaac cggcgcaata taagttaaag ccagctcaat actccaatct ttcatctacc    5100
gatcttgcta aggtcgtaac agtatccaca cagcaaaatt ctcaagtgtt taccgttaac    5160
gttaaagata cagatcctgt tcgggcaaga gatattgcaa atgaagttgc taaggttttt    5220
gaaaagaaaa ttgctaaaat catgagcatt tccaatgttt ccgttgtttc aagggcaacg    5280
gctgatccga taccagtatt gcctcggttg aatctaatgg cattaattgg cctagtttta    5340
ggagtgcttg tcgctttcgt ttggggattg attcgagaac tgacagatca gaccattaag    5400
gatattgact ttatcacgga cgaccttggg ttggttaatt tgggaatagt caattatgtt    5460
caacatatgc gtgacatgag tgaagcgatc gatgccacaa agtcaataga agctgaggat    5520
actgaagatt acgatgcgtc ggactttccg caacgtagcc gtcgccgaat ctaaggagga    5580
agaaaacatg aagtggtctt tcaaacaact tttccaccgg caacaagaag atcaagaaac    5640
```

```
tcaaaagaac ggggtcattt tagtcacttt cgctgaacca aaacatgttg tttcagaaca    5700
gtttcgcaca gtgcgaacta atattgagtt tgctggagca gctcttgata agtgtcaagt    5760
tgttatgttt acgtcttcag tgatgtccaa gggcaagtcg actgtttcgg caaacgttgc    5820
ggtaacttgg gctcaggcgg ggaaaaaggt tttactgatt gattgtgacc ttcgacgacc    5880
gactgtacat gcaacttttc gaacgcttaa tctagaggga gtcacaacag tattaacggg    5940
gaaaagttct gctcacaata tagttgagca aacatttgtg agtaatttag atattcttac    6000
ctccgggccg ctacctccca ctccgtctga acttttaaat tcacaacgta tggctaacct    6060
cgtggattgg gcacgcgaca attatgatat tgttgttcta gatgcaccgc cagttttggc    6120
agtatctgat gtacaggtct tagtccccaa aacagatggc gtagtggttg tcgcaaagat    6180
ggggaagact ttaaagggag acttaagacg aactattgaa gttctgaagc ttgcaaaagc    6240
taaacttctt ggatgtgtag agcgtgtgaa tgttaaacgt ggcgatcgcg gctatggcta    6300
cggttatggc tacggttatg ggaatgaagg gactaaataa tccgatatta tcaacctaaa    6360
gaaaaaaggc atagctcaaa tatttataaa ttgatgctta acgcattgtt gtctgttttt    6420
gatgtttggg tggttatctg attatttatg tgatttaata gtggcaagaa aagtttataa    6480
atttaatata cttgcacaaa gattttttaag aatgcaagtt tttattcttg caaagttgaa    6540
aaagtgattt cgactttagc acggggaacg cgacatacta aagtcacttc acgtagtgcg    6600
tttgggggag gaaggatcat gtatcaacac ttcattaaaa gaattttaga tattttggga    6660
gcaataatag cattgctaat cttggcaatc ccgtttatca ttattgcaat acttattagg    6720
atggattcaa cgggtccagc cttttttcgt cagcaaagaa tggggaagga tgggaagccc    6780
tttagaattt acaagtttcg tacaatggac caagaggccc cacacgatct tgcaactgct    6840
aaactagata atgctaataa gcagattaca cgggtcggtc gattgctccg aaagacaagt    6900
attgatgagt tacctcagtt cattaatgtg ttaaagggcg acatgagcat ggtcggacca    6960
cgtccggttg tcttgacaga aactgagcta attgaaatgc gtcacaaaaa tggcgctgaa    7020
agtgctttac cggggataac aggattagcg caggtaaacg gaagagatcg gttatccaat    7080
ttaagtaaat ctaattacga tggtatttat gtttcttcaa tttcattttt tatagattca    7140
aagataatgg tcaaaacttt ctggtatgta gctcttcgat taggtattag agaaggtcgt    7200
ccaaattcta aaaagttaa tgctgctaat atcggagaaa aaaatattag gccgaacgaa    7260
cagcaactat ttttaaaaag gaaagcttag atttaatgaa tgataatact aaagaaatta    7320
gcttttgtac cgttacttat aacagcgcaa aagaagtgac ccagttaata gaaaatatag    7380
agtctctaaa aagcgatttg ttttcctcac gagttttcat tgttgataat gggtcccaag    7440 atgcacagt gaatatagtt ttaaagcttt ctcaggaaca ctctaatctt gttttaatta    7500
ggcctgatgt gaataggga tttggagcag gcaacaatca ggtgttaaat atgattacct    7560
cggattacca tattctgatt aatccagatg tgcgtatacc gtcctccaga acgattgaaa    7620
agatgatcgg gtatatggat actcattctg atgttggact gttatccccc aaaattctta    7680
atgttgacgg ctcagttcaa aaattattta gacataatcc tactgtactt gatatggcgt    7740
tacggttcat ctcacctaat cttatgaaaa aaaggcaaga ttggttcgtc catgaagaga    7800
ccgggtatac tcagagcgga gtgatcgatc aagctagtgg agcatttatg ttttccgta    7860 catctgtatt taaaggtata gcgggttttg atgagagata ctttatgtat ttggaggatg    7920
cagacattac tcgtaaggtc aatgctgtta gcaaagcaat tttttatcct gaagtaagca    7980
tcatgcataa gtggaatcga caaaatcatt caaagttgaa attcattggc tatacaatta    8040
```

```
agagcatggt tcaatatttt aacaaatggg gatggaagtt attctaacca ctggggagat   8100
tgattgaatg atttggctgg gaattgtctg tattagcttt atatctagtt gtttccaaaa   8160
attagagaag tcagcgggtt tgatatcttt tttgggttta ggttatttgg cgggcacacc   8220
aaatatgttg tacgatcccg atgcttttgt ctatttacaa aattataatt cgggcactga   8280
ttatttcgag acaggatata attgggtgac aaagctattt gagcctagtg tagattatca   8340
aacatttaga ttatacagta gtttatttat tttttcctg atgtttttag cagtactttt    8400
gatgacaaag cacgtatcaa gtattgcgtt ggtttatgca atcgcaatgt tccggttga    8460 taaagcacag actagaaatg tcatggcagc cgtcttttgt tcctttttgg agttcstgtt   8520
gttttgctgt aagcttggga aaagaggaat tcttccctca ttactggtca ttttttattag  8580 gatctttttt tcatagtctt gcactctact ttcttttact accattatta tggttgttta   8640
aaggctttat tgaaaagcat ttttctgcaa ttactacatg tctaattgtt gttgcgttta   8700
tttttgaaat cttaggttca acaagcatag cgccactatt agtacaactt tgggaaagt    8760 ttgcaaatcg tgcgaacgtt gcagaaaatg tgtcaacttt atatgctgga ggtcagccat   8820
ttagtcagtg gtttgtttct ttcgcagtta ctatgatgat aatttaaca gttcaatttc    8880 ttagaaggca atacctaac aatatgagat cctattacca aatgatttta tgttcttcga    8940
tattatggtc agcagcgtta atattgatga ctctttcaat tgactacata agaattctga   9000
gaattgttac gtacttctat tttatctata tcgtgaatgt tacttcaaat cagaagagca   9060
cggatcgcct tataggggtg acaatcagta ttggatctgc agtcgttttg atgtttgtcg   9120
ggttatgggt ctacggattt agtggtgacc aaattcgagc aattttggg tttatttaag    9180 gggactgaag aatgttgaaa gttggagtaa ttgttgttac ttacaatccg gatttaatga   9240
ttctacagaa taatctgacg acactaaaaa ggcaaaatgg catcaactgt ctgattgttg   9300
ataacggctc taagaattca aacgatttaa aaaaagtaag tgaaaactta aaagtcaaca   9360
ttatttcact tgatagtaat cgtgggattg cttatgcaca aaatcgaggt tttgaatttt   9420
ttcaaagaga agggttaaag tgggcgctta ctttagacca agacagcata gttcctgata   9480
acttactaga agtgtatgta aagcaaaaag aattgaactc ttccgacaca gcaattttaa   9540
cttgtagcta cgttgatgag gactggactg gaaagcaaaa agaagctatg cttcagcgtg   9600
aaaagattgt gcaaaagcaa tatgtcatt cttcaggtaa tcttgtaaga atttcctctt     9660
ggcaaaaagt gggtggattt gacgaattcc tctttattga catggttgac ttcgactttg   9720
acgctaaact attttagct ggcttaaaa tctggcagac gaatgaagtc gtactaaaac      9780
attctgttgg acaatcctta aagaagccca tcgtgaaaaa aatacttctg attccagaaa   9840 ctgctattt ggccgatcat tcaccaattc gtcagtatta catttataga aatagtatta    9900
ttttcgagaa aagatacacg atgattaccc aacgaaagtt tgttgttctc catactttcg   9960
ttgcaacaag gagaatgttt gcgtatagca ataagttacg caagatgttt gcagcttggc   10020
gcggagttat tgatggtgcc agatacaatg tagacaagga caaacaattt aaaaaaacac   10080
tggcaaaact gaaacgatag ttatttgggg tgaaataatg agaagtgaaa acgtaagtgt   10140
cgcaatttgt ttagccacgt ataacgggga gaagtattta gaaaaacaga ttgactcaat   10200
agtttcccaa tctgtctcta gttggacatt gtttattaga gatgatggtt ccaccgatgg   10260
aacgcaaaaa atcattaaaa agtttgcaaa gaagtatccg caaaaagttt tcaacttatc   10320
aggtcttcat ggaggcggaa attctaaaga aaatttttt actattctgc aatgggtgag   10380
```

```
cgaacacaaa actttttgatt attttatgtt ttctgatcaa gatgacattt ggttacctga   10440
taaaattgca ttaagtgtca aggctattga ttctgatgat tctccatgtt tagttcatac   10500
tgatctaaaa gttgtcgata aaaacttgga tacaataaca gaatctttca ttcggtacag   10560
taacttaaat tctcaagtaa aggatttttc gcatatcctt gtacagaaca atgtaactgg   10620
ctgcacaatg ttgtggaata agagtttaaa cgatttaatc gattttcatc cagattctag   10680
aatccttatg catgattggt ggattgcttt aattgcatca gcgtttggaa atgtcgtctt   10740
tgtaaaaact ccaaccatcc tctatcgaca acatgatgaa aatgtagtgg gggcagaagc   10800
ggctggttct gtggcatata ttatttcaaa attgcgtaat tataagttga ttaaaaaagg   10860
attgcaacgt acctttgggc aagcaaatat ttttaaagag atttattatc atcggttaga   10920
tgccagttct aaaagtatac tagatgagta tttgcagctt cctgccaagt ccaaacttag   10980
aaaaatatat ctttctctca agtatggatt tacaaaacaa agcaccatac aaattattgg   11040
gcagtttctt tttgtctagt ctgttgaggc tgattaattg cgagttttaa aaaattattt   11100
atatagtgtt gggtatcaag ttctaaacat gatattgcca ctcataacag gaccgtatgt   11160
tgcacgagtt cttggaccga agggtgttgg gattaatact tatacaggtg cagtaacaca   11220
atactttgtt ttattcgctg gcctagggat agcgctttat ggaaatcgac agattgctta   11280
tgttaagggt gacccacatc agttaagcat taccttttgg gaaatacagt ttattaaaac   11340
gattacaaca gtttgcgcct ttgtcgcttt ttcaatatat ttaattttcg tcaaagaata   11400 taagtttat ttactgttac aatccgcgta tattttagct acaggatttg atatttcatg   11460
gctttatgag ggcgttgagg atttttaaaaa gaccttttact agaaacacgt tagttcgaat   11520 agtctcccctt gttctaatcc tcacgctggt acacaaacaa agtgacgttt gggtatacat   11580
agtcattctc gcagcttcta acctcggtgg gtatgttgcg ttgtggccaa ctctaaggcg   11640
gctgctcgta cccattaaac tgtctgaatt acatcctagg aaacatttga agggcacact   11700
gattttattt gtgccataca tgacgctgaa catttatcct atcattaata aaacattact   11760
caaacatttt cttggggttg atgcttccgg ttatttttgaa aaaagtgatg tgatgatacg   11820
tatggcgttg acagtagtga cgtcggtaag cgcagtatta ctgccacata catccaaggc   11880
ttttgctgat ggcaaggttt cgttaattaa gaaattgcta aaaacctctt ttggatatgt   11940
gtccatgatg gcattcccaa tcgcattagg aatggcggca atagcaccaa aatttggtgt   12000 tttctttttat ggtgaagggt ttgcaccggt tgggccagca atgatgatag aatctagtgc   12060
cattattttc atggggtggt cgagcatcac aggtaatcag tatttaattc cgacgatgca   12120
gtcaaagcat tacacgcact cagttcttct aggctcggtt ttgaatattg ttcttgacgt   12180
tcctcttatc attattttttg ggcttaatgg tgcagcgttt gctactttga ttgctgaagc   12240
gtttattgct atatatcagt taataatgat cagtggtcag gttgattatt ccacttggct   12300
gatggacatc attaaatatt gtgtagctgc tataatcatg ttctgctttg ttttttttcgc   12360 aagtagcatg ttgacgatga ccatcttgac cttagtgctt gaaatcatgc ttggtgccat   12420
catttactta gtatgtctgt ttcttatgaa acccgcaact aataagcaac tcaaacgggc   12480
agcattctca attattaacc gagttcggtc atgattattt ttgggggaat aatgacaata   12540
agacgaagag tttcttggtt gattcgttca cctgcacgat tacatgttgt gtatcggatt   12600
gacgatttta caaataattt gaaggttcga agactgttac atatactatt gatcccagtc   12660
ggcatgttaa acttaattag gctaaaactg atgactagat cacctgaaaa gtttatgtat   12720
caattatcaa ttgttactac agtcaaaaat gaggctccat acttaagaga gtggctgaga   12780
```

```
tatcacattt cggttggagt acagcacttt tatctttatg ataatgatag tcaagataac    12840
ttagatgaag tgttaaaaga tttttccgac tacgttactt taacaaagat acacggacga    12900
gttagacaat ttgatgcata caatgacgcg ataaatcgat tcaggtatga aacaaagtat    12960
atggcggtga tagacgcgga tgagtttatt tttagaccag gtaaagacaa gctgttacta    13020
cctcttattg attatttact ttcaaataag tcatttggag gattggcggt gaattgggca    13080
atatttggtt cttcgggttt aaaaaagaaa cctttaggat tggttaccga caactttgta    13140
tatcgggcca acgataactt taggaaaaac aggctggtta aaactatctg caatccgaga    13200
aaagtctttt acttttcagt tagccatgct gcaaattact tgccaggttt ttatgcagtt    13260
aatgagaatc aggaaaaagt tgattggaca acaacgcaag ttcccagtat cagtaagatt    13320
agaattaatc actattattc aaaatcacaa gaagagtttt tacgaaagcg agctcgaggc    13380
gctggggatg ttgttggcct tagagactta ggagaattcg cagaacatga tcgaaatgat    13440 gttttgacg actcgcttag agtttataat gaatcaagag gttaaacaa agactgaggg    13500 ggatattgaa agatgaaggg gattatatta gctgggggat ccggaactcg actctatcca    13560
attacgaagg caacaagtaa acagttagtt ccaatttatg acaagcccat gatttattac    13620
ccattctctg cgctaatgtt gtctgggatc aaagagtttc tgattatttc tacgccagaa    13680
tttctgccac agtttgaaga attatttggt gatggacata ctctgggact aaatattcat    13740
tacaaggttc aaacagagcc aaatggattg gctgaggcat ttatccttgg tgcggatttt    13800
atcggtaatg attccgttgc tttagtgctg ggagataatg tttttatgg tgctgggtta    13860 tcaaagctat tacaagatgg ggccgcaaag gaatctggcg ccacaatttt tgggtatcag    13920
gtaactgatc ctgaacgttt tggtgtagta gaatttgata gccatcaaca cgctgtatcg    13980
attgttgaaa agccaaccca tccacgcagt aattatgcag taactggttt gtattttat    14040 gataatgatg tggttaatat tgcaaaaaat gtaaagccat ctgcgcgtgg cgaacttgaa    14100
attaccgatg tgaatgagga atatcttcgt cgcgggcagc tagatgtaaa agttatgggc    14160
agaggttatg cttggttaga tactggaacg catgactcat tgcttgctgc ttcaagtttt    14220
gttgcaacta ttgagaatca acaaaatctt aaagtggcgt gtcttgagga aattgcttat    14280
cgtatggggt atattaatct tgaacagttg gaagaacttg cccagccgct caaaaaaaat    14340
gattatggtc agtatttgtt gcgtttggtc aaggaggaga gtaagtaatg ctttaaaag    14400 taatcccgac aaagttaact gatgtcaagt tggttgagac agatgttttt ggtgataatc    14460
gcggtttctt cacagaaacg tatactcgac ctaagtttca agaggcgggc atcacgaatg    14520
atttcaatca agataatcag tcattgtctg ctgaagcagg tgtgttaaga ggcatgcact    14580
accagatggc tccacatgca caaacaaaat tagttcgtgt ggtaactggt gttgttgaag    14640
atgttttggt tgacatccga aagggttcac caacttatgg tcagtgggaa ggatatattt    14700
taagcgaatt caaccatcgc caattacttg tgccaaaggg gtttgctcat gggtttatta    14760
cattaactcc aaatgttaat tttgcttata aggttgaagg gtattatgct cctgaagctg    14820
atcgtggaat tgcctttgat gatcctgaca ttggcattaa ttggccaatg tcaacagcac    14880
accttattat gtctgagaag gatcaacacc atccacagct gagggatgct gaaaataact    14940
ttgtatacgg ggagatttga taatgaaact tatgatcact ggcggggctg ggtttatcgg    15000
ttcaaatttt gttcattttg tttataataa ccatccagat gttcagatta tggttttgga    15060
caagctaaca tatgccggca ataaggccaa tattgaagat atcttgggcg atcgtgtcaa    15120
```

```
attagaagtc ggggatattg ccgacaagaa tttggtcgat aaattgatga gtgaagtcga   15180
tacagttgtc aactttgcgg cagaaagtca caatgacaat tcgttgatta atccggatcc   15240
gttcctgcac agcaatgtta ttggcaccta tactttactt gaagcagcaa gaaagtacga   15300
tgttcgattc caccatattt ccacagatga ggtgtacgga gatctaccat tacgtgcgga   15360
tcttccagga cacggggaag gccctggcga gaagttcacc gttaacagtc gttataatcc   15420
ttccagccca tattcttcaa ctaaagctgc cagtgacatg ttggtacatg catgggcacg   15480
ttcatttggc gtacgcgcaa caatttctaa ttgctcgaat aactatggtc cataccaaca   15540
cattgagaaa ttcattcctc ggcaaatcac aaacatttta agcggaatca aaccgaagct   15600
ttatggcact ggcaaaaatg ttcgtgattg gattcacaca aacgatcatt caagtgctat   15660
ctgggatatt ttgactaacg ggaaaattgg tgagacttac ttgatcggcg ccaatggcga   15720
aaaagacaat aagacggtac tcgaacttat cttaaaattg atgggcaaac cagctgatta   15780
ctatgaacag gttaaggatc gtccggggca tgatatgcga tatgccattg atgcttccaa   15840
aacccgtgaa gaacttggtt gggaacctca gtatacgaat tttgaagaag gtttagcaga   15900
taccatcaaa tggtacacag atcatcacag ctggtggcaa ggtgaaaaga ctgcggtaga   15960
agaaaagtac caagaaaacg gtcaatgact ttagctcata gtaatggtcg tcactaatta   16020
tgaacctgtt attttctgga atgtcgagga gaagatacat gaagactttg attactggtg   16080
cgcaaggtca gcttggtaca gaattgcgcc gcctattaga tgcgcagggc gttgcttatc   16140
gagcaacaga tgcccatgat ttagacatta ctgatgagac tgcggttaat cagtatttta   16200
aagattatca acccgagtta gtttatcact gtgctgccta tacggctgtc gataaggctg   16260
aaggtgaagc taaggcaatt aatcaaaaag ttaatgttga cggaacacgt aatttggcaa   16320
aagcggccgc tgaagtagat gcgacacttg tttacatcag tacagattat gtatttgatg   16380
gtgacagcaa agaaatttat accgtcgatg atcaacctgc tccacgtaat gagtatggcc   16440
gggcaaaata tgaaggtgag caacaagtcc aaaaatatct taagaagttc tatattatta   16500
gaacctcatg ggtattcggt gaatttggtc ataactttgt ttatacaatg ttggacttag   16560
ccaagacaca caaagaactc agcgttgtcg acgatcaata cggtcgtccg tcatggacca   16620
agacactcgc agaattcatg acgttcgcag tgaatcaaca tttggattat ggcatttacc   16680
acttgtctaa tgataacagt tgtaactggt acgaatttgc tagcgctatt ttggctgaca   16740
aagatgttga tgttaagcca gtatcgtcat cagagtatcc gcagaaggca tggcgtccgc   16800
gacattcgat tttggactta agtaagacga aggttacagg ctttaagata gacacttggc   16860
aagaagcttt gacaaacttt ttacaagtta tcgataaata agtgaaacta gatcaagtgt   16920
atcaaaaaga acgtaaaaac caatctggcg attggtttcg gcgcccttt gatacacgta   16980 acaataacgg gtctacactt tctggtgttg agaaataatc agcactgaac gtgtaggccc   17040
tttttggata acgcaaaaag acacctattc agtgaccatg ctatgcttgt tagcgtcgaa   17100
accaaaagca agcgaggtta tgagtaaatg tcccaatacg attctacact gtccgtcctt   17160
ggaataccag accataatat caaagtagcc tttgttcgtc atgaatatcg cggcaacggg   17220
gtacgtcgcc gccagtatca tgtgattgat gctgagctga cttaccggtt acactgtgtg   17280
gctttgaggc cttgcaccct aacgggtttt acacggccca tgtgcgcgtc ctcaacgggg   17340
```

```
ttgaaatgcc gacagtcatt gacttgcaca agcaacgatg gcgctgtcat aactgttacc   17400
acacagtcag tgccaagacg ccactcgtgc aacccaacca cacgatcgcc gctcacatga   17460
cagagcgaat catgaagtta gcgcatgaac ggttgccagt caaaaccatc gcccgtatta   17520
tcggaatctc agcctcctcg gttcaacgga tcattgacca aaatctcaaa ctccgaccgg   17580
ctcgccggct acccacgcga ctctgctttg atgagttccg ttccactcat ggcatgatgt   17640
cgtttatctg tcttgatgcc gattcacatc atctgattgc cttgcttggt gatcgatgca   17700
accgcacgat taaaaacttc ttcctcgctc attattcact cgctgaacgc actcgggtcc   17760
agacggtcac catggacatg aatgcagctt atcagacgat tattcatgag gttttcccca   17820
aggcccaagt cgtcattgat cggttccata tcattcaact tgcggctcgt gcccttgatc   17880
aggtacgcgt ccaagcgctc aaacagcttg atgacaaaca cagccgtcct tataagatca   17940
tgaagacaaa ctggcggctt tttcatcaaa ctgcgcctga cgctaaacac aaacagttcc   18000
tgtttggttt gaatgaagac gtcacgcaac aggaggccat cgatattgca cttgatactg   18060
agcccaagct caagcaaacc tacgagacct acttagcgct tcatgatgct tgatggtgta   18120
agaaacatcc cgcggaactg gcaaacctgt tagctactta cgagccaaac ggtacggcaa   18180
tggacatgac gatcgcgacg cttaagcgac acaaagtcgc tgttctcgcc gctgtcacca   18240
gcccttattc caacggtccg atcgaagggt taaccgcctc atcaagtcac tcaaacgatc   18300
ctgttttggc ttcaagaatc agctgaactt cttcaaacga atcataccaa atcacggcat   18360
aacatgacaa agacggcggc atgatcctga agctataata ggcgcagtaa tcaccttcag   18420
ggcaacgtga agctcatgcc taatagaaat acgagagcgg cctaaggtcg cggcgatgta   18480
ttgaatcgtg tggtgttgca tcagttctat ctgagatcgt tcaattaagg ttataatggc   18540
catgggacct gtccttctct ctagatggta tgttatgcaa acaccatttt agcaagaacg   18600
gacaggtctt tttttcacatt ttctgggtgg taactttaat tatgcaatct aggcattaag   18660
ggtcaaatta ccagatgata atatgcctga ttcattaata atcgcgtgtg aaaaaggaac   18720
attaatctta ggagaattga tgatcg                                        18746

<210> SEQ ID NO 2
<211> LENGTH: 20
<212> TYPE: DNA
<213> ORGANISM: Artificial Sequence
<220> FEATURE:
<223> OTHER INFORMATION: GAPDH forward

<400> SEQUENCE: 2
gggaaggtga aggtcggagt                                                  20

<210> SEQ ID NO 3
<211> LENGTH: 20
<212> TYPE: DNA
<213> ORGANISM: Artificial Sequence
<220> FEATURE:
<223> OTHER INFORMATION: GAPDH reverse

<400> SEQUENCE: 3
tcagccttga cggtgccatg                                                  20
```

<210> SEQ ID NO 4
<211> LENGTH: 20
<212> TYPE: DNA
<213> ORGANISM: Artificial Sequence
<220> FEATURE:
<223> OTHER INFORMATION: IL-6 forward

<400> SEQUENCE: 4
cggtacatcc tcgacggcat                                               20

<210> SEQ ID NO 5
<211> LENGTH: 21
<212> TYPE: DNA
<213> ORGANISM: Artificial Sequence
<220> FEATURE:
<223> OTHER INFORMATION: IL-6 reverse

<400> SEQUENCE: 5
tcaccaggca agtctcctca t                                             21

<210> SEQ ID NO 6
<211> LENGTH: 23
<212> TYPE: DNA
<213> ORGANISM: Artificial Sequence
<220> FEATURE:
<223> OTHER INFORMATION: IL-8 forward

<400> SEQUENCE: 6
tgtggtatcc aagaatcagt gaa                                           23

<210> SEQ ID NO 7
<211> LENGTH: 25
<212> TYPE: DNA
<213> ORGANISM: Artificial Sequence
<220> FEATURE:
<223> OTHER INFORMATION: IL-8 reverse

<400> SEQUENCE: 7
tatgttctgg atatttcatg gtaca                                         25

<210> SEQ ID NO 8
<211> LENGTH: 19
<212> TYPE: DNA
<213> ORGANISM: Artificial Sequence
<220> FEATURE:
<223> OTHER INFORMATION: CCL20 forward

<400> SEQUENCE: 8
ctgcttgatg tcagtgctg                                                19

<210> SEQ ID NO 9
<211> LENGTH: 18
<212> TYPE: DNA
<213> ORGANISM: Artificial Sequence
<220> FEATURE:
<223> OTHER INFORMATION: CCL20 reverse

<400> SEQUENCE: 9
cacccaagtc tgttttgg                                                 18

<210> SEQ ID NO 10
<211> LENGTH: 16
<212> TYPE: DNA
<213> ORGANISM: Artificial Sequence
<220> FEATURE:

```
<223> OTHER INFORMATION: TNF-alfa forward

<400> SEQUENCE: 10
tcagctccac gccatt                                                          16

<210> SEQ ID NO 11
<211> LENGTH: 18
<212> TYPE: DNA
<213> ORGANISM: Artificial Sequence
<220> FEATURE:
<223> OTHER INFORMATION: TNF-alfa reverse

<400> SEQUENCE: 11
cccaggcagt cagatcat                                                        18

<210> SEQ ID NO 12
<211> LENGTH: 20
<212> TYPE: DNA
<213> ORGANISM: Artificial Sequence
<220> FEATURE:
<223> OTHER INFORMATION: COX-2 forward

<400> SEQUENCE: 12
cccttgggtg tcaaaggtaa                                                      20

<210> SEQ ID NO 13
<211> LENGTH: 19
<212> TYPE: DNA
<213> ORGANISM: Artificial Sequence
<220> FEATURE:
<223> OTHER INFORMATION: COX-2 reverse

<400> SEQUENCE: 13
tgaaaaggcg cagtttacg                                                       19
```